US007364566B2

(12) United States Patent
Elkins et al.

(10) Patent No.: US 7,364,566 B2
(45) Date of Patent: Apr. 29, 2008

(54) METHOD AND APPARATUS FOR INTRA-AORTIC SUBSTANCE DELIVERY TO A BRANCH VESSEL

(75) Inventors: Jeffrey M. Elkins, Novato, CA (US); Aurelio Valencia, East Palo Alto, CA (US); Samir R. Patel, Mountain View, CA (US); Ricardo Aboytes, East Palo Alto, CA (US); Harry B. Goodson, Fremont, CA (US); Craig A. Ball, San Carlos, CA (US)

(73) Assignee: FlowMedica, Inc., Fremont, CA (US)

( * ) Notice: Subject to any disclaimer, the term of this patent is extended or adjusted under 35 U.S.C. 154(b) by 326 days.

(21) Appl. No.: 11/084,434

(22) Filed: Mar. 18, 2005

(65) Prior Publication Data

US 2005/0245882 A1 Nov. 3, 2005

Related U.S. Application Data

(63) Continuation of application No. PCT/US03/299995, filed on Sep. 22, 2003.

(60) Provisional application No. 60/502,389, filed on Sep. 13, 2003, provisional application No. 60/479,329, filed on Jun. 17, 2003, provisional application No. 60/412,343, filed on Sep. 20, 2002, provisional application No. 60/412,476, filed on Sep. 20, 2002.

(51) Int. Cl.
*A61M 29/00* (2006.01)
*A61M 25/00* (2006.01)

(52) U.S. Cl. ........................ 604/104; 604/523

(58) Field of Classification Search ............. 604/264, 604/164.01, 164.13, 284, 523, 532, 535, 604/537, 104–106
See application file for complete search history.

(56) References Cited

U.S. PATENT DOCUMENTS 1,696,018 A 12/1928 Schellberg (Continued)

FOREIGN PATENT DOCUMENTS

DE 43 24 637 A1 3/1995

(Continued)

OTHER PUBLICATIONS

"FDA Form 510(K) on related correspondence for Advanced Equipment Development, Inc."

(Continued)

*Primary Examiner*—Kevin C. Sirmons
*Assistant Examiner*—Elizabeth MacNeil
(74) *Attorney, Agent, or Firm*—Townsend and Townsend and Crew LLP

(57) ABSTRACT

A renal flow system injects a volume of fluid agent into a location within an abdominal aorta in a manner that flows bi-laterally into each of two renal arteries via their respectively spaced ostia along the abdominal aorta wall. A local injection assembly includes two injection members, each having an injection port that couples to a source of fluid agent externally of the patient. The injection ports may be positioned with an outer region of blood flow along the abdominal aorta wall perfusing the two renal arteries. A flow isolation assembly may isolate flow of the injected agent within the outer region and into the renals. The injection members are delivered to the location in a first radially collapsed condition, and bifurcate across the aorta to inject into the spaced renal ostia. A delivery catheter for upstream interventions is used as a chassis to deliver a bilateral local renal injection assembly to the location within the abdominal aorta.

11 Claims, 41 Drawing Sheets

U.S. PATENT DOCUMENTS

| | | |
|---|---|---|
| 2,499,045 A | 2/1950 | Walker et al. |
| 3,455,298 A | 7/1969 | Anstadt |
| 3,516,408 A | 6/1970 | Montanti |
| 3,667,069 A | 6/1972 | Blackshear et al. |
| 3,730,186 A | 5/1973 | Edmunds, Jr. et al. |
| 3,791,374 A | 2/1974 | Guarino |
| 3,995,623 A | 12/1976 | Blake et al. |
| 4,248,224 A | 2/1981 | Jones |
| 4,309,994 A | 1/1982 | Grunwald |
| 4,345,602 A | 8/1982 | Yoshimura et al. |
| 4,407,271 A | 10/1983 | Schiff |
| 4,423,725 A | 1/1984 | Baran et al. |
| 4,459,977 A | 7/1984 | Pizon et al. |
| 4,490,374 A | 12/1984 | Bandurco et al. |
| 4,493,697 A | 1/1985 | Krause et al. |
| 4,536,893 A | 8/1985 | Parravicini |
| 4,546,759 A | 10/1985 | Solar |
| 4,554,284 A | 11/1985 | Stringer et al. |
| 4,685,446 A | 8/1987 | Choy |
| 4,705,502 A | 11/1987 | Patel |
| 4,705,507 A | 11/1987 | Boyles |
| 4,712,551 A | 12/1987 | Rayhanabad |
| 4,714,460 A | 12/1987 | Calderon |
| 4,723,939 A | 2/1988 | Anaise |
| 4,753,221 A | 6/1988 | Kensey et al. |
| 4,781,716 A | 11/1988 | Richelsoph |
| 4,817,586 A | 4/1989 | Wampler |
| 4,834,707 A | 5/1989 | Evans |
| 4,846,831 A | 7/1989 | Skillin |
| 4,861,330 A | 8/1989 | Voss |
| 4,863,461 A | 9/1989 | Jarvik |
| 4,888,011 A | 12/1989 | Kung et al. |
| 4,902,272 A | 2/1990 | Milder et al. |
| 4,902,291 A | 2/1990 | Kolff |
| 4,906,229 A | 3/1990 | Wampler |
| 4,909,252 A | 3/1990 | Goldberger |
| 4,911,163 A | 3/1990 | Fina |
| 4,919,647 A | 4/1990 | Nash |
| 4,925,377 A | 5/1990 | Inacio et al. |
| 4,925,443 A | 5/1990 | Heilman et al. |
| 4,927,407 A | 5/1990 | Dorman |
| 4,927,412 A | 5/1990 | Menasche |
| 4,938,766 A | 7/1990 | Jarvik |
| 4,950,226 A | 8/1990 | Barron |
| 4,957,477 A | 9/1990 | Lundback |
| 4,964,864 A | 10/1990 | Summers et al. |
| 4,976,691 A | 12/1990 | Sahota |
| 4,976,692 A | 12/1990 | Atad |
| 4,990,139 A | 2/1991 | Jang |
| 4,995,864 A | 2/1991 | Bartholomew et al. |
| 5,002,531 A | 3/1991 | Bonzel |
| 5,002,532 A | 3/1991 | Gaiser et al. |
| 5,053,023 A | 10/1991 | Martin |
| 5,059,178 A | 10/1991 | Ya |
| 5,067,960 A | 11/1991 | Grandjean |
| 5,069,662 A | 12/1991 | Bodden |
| 5,069,680 A | 12/1991 | Grandjean |
| 5,073,094 A | 12/1991 | Dorman et al. |
| 5,089,019 A | 2/1992 | Grandjean |
| 5,098,370 A | 3/1992 | Rahat et al. |
| 5,098,442 A | 3/1992 | Grandjean |
| 5,112,301 A | 5/1992 | Fenton, Jr. et al. |
| 5,112,349 A | 5/1992 | Summers et al. |
| 5,119,804 A | 6/1992 | Anstadt |
| 5,129,883 A | 7/1992 | Black |
| 5,131,905 A | 7/1992 | Grooters |
| 5,135,474 A | 8/1992 | Swan et al. |
| 5,158,540 A | 10/1992 | Wijay et al. |
| 5,163,910 A | 11/1992 | Schwartz et al. |
| 5,167,628 A | 12/1992 | Boyles |
| 5,180,364 A | 1/1993 | Ginsburg |
| 5,205,810 A | 4/1993 | Guiraudon et al. |
| 5,226,888 A | 7/1993 | Arney |
| 5,256,141 A | 10/1993 | Gencheff et al. |
| 5,257,974 A | 11/1993 | Cox |
| 5,282,784 A | 2/1994 | Willard |
| 5,290,227 A | 3/1994 | Pasque |
| 5,308,319 A | 5/1994 | Ide et al. |
| 5,308,320 A | 5/1994 | Safar et al. |
| 5,312,343 A | 5/1994 | Krog et al. |
| 5,320,604 A | 6/1994 | Walker et al. |
| 5,326,374 A | 7/1994 | Ilbawi et al. |
| 5,328,470 A | 7/1994 | Nabel et al. |
| 5,332,403 A | 7/1994 | Kolff |
| 5,345,927 A | 9/1994 | Bonutti |
| 5,358,519 A | 10/1994 | Grandjean |
| 5,364,337 A | 11/1994 | Guiraudon et al. |
| 5,370,617 A | 12/1994 | Sahota |
| 5,383,840 A | 1/1995 | Heilman et al. |
| 5,397,307 A | 3/1995 | Goodin |
| 5,411,479 A | 5/1995 | Bodden |
| 5,419,777 A * | 5/1995 | Hofling .................... 604/264 |
| 5,421,826 A | 6/1995 | Crocker et al. |
| 5,429,584 A | 7/1995 | Chiu |
| 5,453,084 A | 9/1995 | Moses |
| 5,464,449 A | 11/1995 | Ryan et al. |
| 5,476,453 A | 12/1995 | Mehta |
| 5,478,331 A | 12/1995 | Heflin et al. |
| 5,484,385 A | 1/1996 | Rishton |
| 5,505,701 A * | 4/1996 | Anaya Fernandez de Lomana ............ 604/101.03 |
| 5,509,428 A | 4/1996 | Dunlop |
| 5,536,250 A | 7/1996 | Klein et al. |
| 5,558,617 A | 9/1996 | Heilman et al. |
| 5,599,306 A | 2/1997 | Klein et al. |
| 5,609,628 A | 3/1997 | Keranen |
| 5,613,949 A | 3/1997 | Miraki |
| 5,613,980 A | 3/1997 | Chauhan |
| 5,617,878 A | 4/1997 | Taheri |
| 5,643,171 A | 7/1997 | Bradshaw et al. |
| 5,643,215 A | 7/1997 | Fuhrman et al. |
| 5,702,343 A | 12/1997 | Alferness |
| 5,713,860 A | 2/1998 | Kaplan et al. |
| 5,720,735 A | 2/1998 | Dorros |
| 5,755,779 A | 5/1998 | Horiguchi |
| 5,762,599 A | 6/1998 | Sohn |
| 5,766,151 A | 6/1998 | Valley et al. |
| 5,776,190 A | 7/1998 | Jarvik |
| 5,797,876 A | 8/1998 | Spears et al. |
| 5,807,895 A | 9/1998 | Stratton et al. |
| 5,817,046 A | 10/1998 | Glickman |
| 5,902,229 A | 5/1999 | Tsitlik et al. |
| 5,902,336 A | 5/1999 | Mishkin |
| 5,913,852 A | 6/1999 | Magram |
| 5,928,132 A | 7/1999 | Leschinsky |
| 5,935,924 A | 8/1999 | Bunting et al. |
| 5,968,013 A | 10/1999 | Smith et al. |
| 5,971,910 A | 10/1999 | Tsitlik et al. |
| 5,984,955 A | 11/1999 | Wisselink |
| 6,039,721 A | 3/2000 | Johnson et al. |
| 6,068,629 A | 5/2000 | Haissaguerre et al. |
| 6,077,256 A | 6/2000 | Mann |
| 6,086,527 A | 7/2000 | Talpade |
| 6,086,557 A * | 7/2000 | Morejohn et al. .......... 604/532 |
| 6,117,117 A | 9/2000 | Mauch |
| 6,165,120 A | 12/2000 | Schweich et al. |
| 6,287,608 B1 | 9/2001 | Levin et al. |
| 6,387,037 B1 | 5/2002 | Bolling et al. |
| 6,390,969 B1 | 5/2002 | Bolling et al. |
| 6,468,241 B1 | 10/2002 | Gelfand et al. |
| 6,508,787 B2 | 1/2003 | Erbel et al. |
| 6,514,226 B1 | 2/2003 | Levin et al. |
| 6,533,747 B1 | 3/2003 | Polaschegg et al. |
| 6,592,567 B1 | 7/2003 | Levin et al. |

| | | | |
|---|---|---|---|
| 6,595,959 | B1 | 7/2003 | Statienko et al. |
| 6,699,231 | B1 | 3/2004 | Sterman et al. |
| 2001/0031907 | A1 | 10/2001 | Downey et al. |
| 2002/0090388 | A1 | 7/2002 | Humes et al. |
| 2002/0091355 | A1 | 7/2002 | Hayden |
| 2002/0169413 | A1 | 11/2002 | Keren et al. |
| 2003/0069468 | A1 | 4/2003 | Bolling et al. |
| 2003/0100919 | A1 | 5/2003 | Hopkins et al. |
| 2003/0144636 | A1 | 7/2003 | Liu |
| 2003/0153898 | A1 | 8/2003 | Schon et al. |
| 2003/0181856 | A1 | 9/2003 | Goldman |
| 2004/0044302 | A1 | 3/2004 | Bernard et al. |
| 2004/0064089 | A1 | 4/2004 | Kesten et al. |

FOREIGN PATENT DOCUMENTS

| | | |
|---|---|---|
| EP | 0 654 283 A1 | 5/1995 |
| EP | 0 884 064 A2 | 12/1998 |
| GB | 2 239 675 A | 7/1997 |
| WO | WO 97/11737 A1 | 4/1997 |
| WO | WO 98/03213 A1 | 1/1998 |
| WO | WO 98/17347 A1 | 4/1998 |
| WO | WO 98/52639 A1 | 11/1998 |
| WO | WO 99/22784 A1 | 5/1999 |
| WO | WO 99/33407 A1 | 7/1999 |
| WO | WO 99/51286 A1 | 10/1999 |
| WO | WO 00/41612 A1 | 7/2000 |
| WO | WO 01/41861 A1 | 6/2001 |
| WO | WO 01/83016 A3 | 11/2001 |
| WO | WO 01/97687 A1 | 12/2001 |
| WO | WO 01/97717 A1 | 12/2001 |
| WO | WO 01/97878 A1 | 12/2001 |
| WO | WO 01/97879 A1 | 12/2001 |

OTHER PUBLICATIONS

Agostoni et al. "Sustained Benefit from Ultrafiltration in Moderate Congestive Heart Failure", *Cardiology* 2001:96 183-189.

Akaba et al., "A Cylinder-Shaped Balloon Catheter for the Management of Dissecting Aneurysms in Acute Stage," *Herz*, vol. 17, No. 6, pp. 390-393, Dec. 1992. Abstract Only.

Aspelin, et al., "Nephrotoxic Effects in High-Risk Patients Undergoing Angiography," *N Engl J Med*, Feb. 2003, vol. 348, No. 6, pp. 491-499.

Bakris et al., "Renal Hemodynamics in Radiocontrast Medium-Induced Renal Dysfunction: A Role for Dopamine-1 Receptors," *Kidney International*, vol. 56 pp. 206-210 (1999).

Beregi, et al., "Doppler Flow Wire Evaluation of Renal Blood Flow Reserve in Hyertenstive Patient With Normal Renal Arteries," *CardioVascular and Interventional Radiology*, vol. 23, pp. 340-346 (2000).

Bergey et al., "Transhepatic Insertion of Vascular Dialysis Catheters in Children: A Safe, Life-Prolonging Procedure," *Pediatr. Radiol.*, vol. 29, No. 1, pp. 42-50, Jan. 1999. Abstract Only.

Bischoff et al., "Modified in Situ Perfusion of the Kidney Using Balloon Catheters," *Fortschr Med* vol. 94, No. 30, pp. 1695-1697, Oct. 21, 1976. Abstract Only.

Canaud et al., "Temporary Vascular Access for Extracorporeal Renal Replacement Therapies in Acute Renal Failure Patients," *Kidney Int. Suppl.*, vol. 66, pp. S142-S150, May 1998. Abstract Only.

Chatterjee, "Refractory heart failure-drugs and devices", *European Heart Journal*, 2001, 22:2227-2230.

Chu, et al. "Fenoldopam in the Prevention of Contrast Media-Induced Acute Renal Failure," *The Annals of Pharmacotherapy*, 35:1278-1282 (2001).

Cohn, "The Management of Chronic Heart Failure," *The New England Journal of Medicine*, pp. 490-498, Aug. 15, 1996.

Darves, "ASHP: Perioperative Fenoldopam Improves Renal Function During Major Surgery," Retrieved from the Internet [Online]: www.pslgroup.com/dg/225C72.htm, Dec. 19, 2002.

Del Greco, "The Kidney in Congestive Heart Failure," *Modern Concepts of Cardiovascular Disease*, Sep. 1975, vol. 44, No. 9, pp. 47-52.

D'Elia et al., "Nephrotoxicity from Angiographic Contrast Material, A Prosepctive Study," *Am J Med*, May 1982, vol. 72, pp. 719-725.

Diaz-Sandoval, et al., "Acetylcysteine to Prevent Angiography-Related Renal Tissue Injury," *The American Journal of Cardiology*, Feb. 1, 2002: vol. 89, pp. 356-358.

Drescher et al., "Prevention of Contrast Medium-Induced Renal Vasospasm by Phosphodiesterase Inhibition," *Invest Radiol* 1998;33:858-862.

Eisenberg et al., "Renal Failure after Major Angiography Can be Avoided with Hydration", *AJR*, May 1981; 136:859-861.

Eisenberg et al., "Renal Failure after Major Angiography," *Am J Med*, Jan. 1980, vol. 68, pp. 43-46.

Eisenberger et al., "Transfemoral Cannulation of the Renal Vessels. Diagnostic and Therapeutic use in Urology," *Urologe* [A], vol. 16, No. 1, pp. 1-5, Jan. 1977. Abstract Only.

Elkayam et al., "Renal Hemodynamic Effects of Vasodilation with Nifedipine and Hydralazine in Patients With Heart Failure," *JACC*, vol. 4, No. 6 (Dec. 1984), pp. 1261-1267.

Elkayam et al., "Renal Vasodilatory Effect of Endothelial Stimulation in Patients with Chronic Congestive Heart Failure," *J Am Coll Cardiol* 1996;28: 176-182.

Fox, "Mechanisms of Contraction," *Human Physiology*, Fourth Edition, Chapter 12, pp. 300-323.

Freeman, et al., "Nephopathy Requiring Dialysis After Percutaneous Coronary Intervention and the Critical role of an Adjusted Contrast Dose," *Am J Cardiol*, vol. 90, (Nov. 15, 2002) pp. 1068-1073.

Garwood et al., "Renal Preservation Strategies for High Risk Patients," *University of Chico School of Medicine*, Cover Page, Table of Contents Page, pp. 1-19, (1998).

Gerlach, et al., "Contrast Medium-Induced Nephrotoxicity: Pathophysiology and Prevention," *Pharmacotherapy*, 2000, 20(5):540-548.

Greco et al., "Atherosclerotic Ischemic Renal Disease," *Am. J. Kidney Dis.*, vol. 29, No. 2, pp. 167-187, Feb. 1997. Abstract Only.

Gruberg, et al., "The Prognostic Implications of Further Renal Function Deterioration Within 48 h of Interventional Coronary in Patients With Pre-existent Chronic Renal Insufficiency," *J Am Coli Cardiol* , 2000, vol. 36 No. 5, pp. 1542-1548.

Halpenny, et al., "The effects of fenoldopam on fenal blood flow and tubular function during aortic cross-clamping in anaesthetized dogs," *Eur J Anaesthesiol*, Aug. 2000;17(8);491-8 Abstract Only.

Heyman et al., "Pathophysiology of Radiocontrast Nephropathy, A Role for Medullary Hypoxia," *Invest Radiol*, 1999:34:685-691.

Hobbs, et al., "An Update on Nesiritide for Treatment of Decompensated Heart Failure," *Exp. Opin. Invest. Drugs*, 2001, 10(5):935-942.

Houghton, et al., "Basal and Reserve Renal Artery Blood Flow: Effect of Endothelium-Dependent and Independent Vasoactive Agonists and Radiographci Contrast Medium in Two Patients", *J invas Cardiol* 2000, 12:211-215.

Iannone et al., "Effect of Primary Balloon Expandable Renal Artery Stents on Long-Term Patency, Renal Function, and Blood Pressure in Hypertensive and Renal Insufficient Patients with Renal Artery Stenosis," *Cathet. Cardiovasc. Diagn.*, vol. 37, No. 3, pp. 243-250, Mar. 1996. Abstract Only.

Jacobs et al., "Reduced Renal Failure Following Thoracoabdominal Aortic Aneurysm Repair by Selective Perfusion," *Eur. J. Cardiothorac. Surg.*, vol. 14, No. 2, pp. 201-205, Aug. 1998. Abstract Only.

Katsumata et al., "Newly-Developed Catheter for Cardio-Renal Assist During Intraaortic Balloon Counterpulsation," *Kyobu Geka*, vol. 46, No. 9, pp. 767-770, Aug. 1993. Abstract Only.

Kay, et al., Acetylcyteine for Prevention of Acute Deterioration of Renal Function Following Elective Coronary Angiography and Intervention, *JAMA*, vol. 289 No. 5, (Feb. 5, 2003).

Kehrer et al., "Construction and Experimental Application of a Catheter for Selective Arterial Kidney Perfusion in Situ", *Urological Research*, 1985, 13:85-89.

Kim et al., "Fluoroscopic Landmarks for Optimal Visualization of the Proximal Renal Arteries," *JVIR*, 10:37-39 (1999).

Kini et al., "A Protocol for Prevention of Radiographic Contrast Nephropathy During Pecutanous Coronary Intervention," *Catheterization and Cardiovascular Interventions*, 2002, 55:169-173.

Kini, et al., "Managing the High-Risk Patient: Experience with Fenoldopam, a Selective Dopamine Receptor Agonist in Prevention of Radiocontrast Nephropathy During Precutaneous Coronary Intervention," *Rev Cardiovasc Med*.2001, 2(suppl 1):S19-S25.

Kobayashi et al., "Experimental Study on the Usefulness of the Autoperfusion Balloon Catheter in Maintaining the Blood Supply to the Distal Organs," *Nippon Igaku Hoshasen Gakkai Zasshi*, vol. 52, No. 5, pp. 682-684, May 25, 1992. Abstract Only.

Lass et al., "Cardiovascular and Renal Hemodynamic Effects of Intravenous Infusions of the Selective $DA_1$ Agonist, Fenoldopam, Used Alone or in Combination With Dopamine and Dobutamine", *Circulation* 1988;78:1310-1315.

Levin, Howard et al., "Reversal of Chronic Ventricular Dilation in Patients with End-Stage Cardiomyopathy by Prolonged Mechanical Unloading," *Circulation* vol. 91, No. 11, pp. 2717-2718, Jun. 1, 1995.

Linden et al., "The Nature of the Atrial Receptors Responsible for a Reflex Decrease in Activity in Renal Nerves in the Dog," *The Physiological Society*, pp. 31-40, (1980).

Madyoon, "Clinical Experience with the Use of Fenoldopam for Prevention of Radiocontrast Hephropathy etc," *Rev. Cardiovasc Med*. 2001, 2(suppl 1):S26-S30.

Madyoon, "Use of Fenoldopam tp Prevent Radiocontrast Nephropathy in High-Risk Patients," *Catheterization and Cardiovascular Interventions*, 2001;53:341-345.

Margulies et al., "Intra-Arterial Atrial Natriuretic Factor (ANF) Attenuates Radiocontrast-Induced Nephropathy in Humans.," *Renal Pathology*, unknown date, pp. 666, Abstract only.

Margulies et al., "Induction and Prevention of Radiocontrast-Induced Nephropathy in Dogs with Heart Failure", *Kidney Int*. 1990; vol. 38:1101-1108.

Masaki et al., "In Situ Perfusion by Retrograde Cannulation of a Tumor Artery for Nephron-Sparing Surgery," *Int. J. Urol*, vol. 2, No. 3, pp. 161-165, Jul. 1995. Abstract Only.

Mason et al., "Renal Dysfunction After Arteriography," *JAMA*, 1985;253:1001-1004.

Mathis et al., "Use of a Guide Catheter as a Temporary Stent During, Microcatheter Intervention," *AJNR Am. J. Neuroradiol*, vol. 19 No. 5, pp. 932-933, May 1998. Abstract Only.

Mathur, "The Role of the $DA_1$ Receptor Agonist Fenoldopam in the Management of Critically Ill, Transplant, and Hypertensive Patients," *Reviews in Cardiovascular Medicine*, 2003;4(Supp 1):S35-S40.

Mathur, et al., "The Effects of Fenoldopam, a Selective Dopamine Receptor Agonist, On Renal Hemodynamics in Normotensive Subjects," *Crit Cre Med* Sep. 1999;27(9):1832-1837, Abstract only.

McCarthy, "Animal Models in Medical Device Development and Qualification," *Charles River Laboratories*, vol. 10(2) 1997.

McCullough et al., "Acute Renal Failure After Coronary Intervention: Incidence, Risk Factors, and Relationship to Mortality," *Am J Med*. 1997;103:368-375.

Mehran, et al., "A Risk Score for Prediction of Contrast Induced nephropathy After Percutaneous Coronary Intervention," Retrieved for the Internet [Online]: www.abstractsonlne.com/viewer, Mar. 31, 2003.

Mehran, et al., "Radiocontrast-Induced Acute Renal Failure: Allocations and Outcomes," *Rev Cardiovasc Med* 2001:2(suppl1):S9-S13.

Middleton, "Ischemic Disease of the Kidney: How and Why to Consider Revascularization," *J. Nephrol.*, vol. 11, No. 3, pp. 123-136, May-Jun. 1998. Abstract Only.

Miller, et al., "Effects of Fenoldopam on Renal Blood Flow and Tubular Function Following Supraerenal Aortic Cross-Clamping," *Ann Vasc Surg*, 2003, Published online Oct. 23, 2003. Abstract Only.

Mintz, et al., "Radiocontrast-Induced Nephropathy and Percutaneous Coronary Intervention," *Expert Opin. Pharmacother.*, 2003; 4(5):639-652.

Mueller, et al., "Prevention of Contrast Media-Associated Nephropathy," *Arch Intern med*, Feb. 2002, vol. 162, pp. 329-336.

Nohria, et al., Medical Management of Advanced Heart Failure, *JAMA*, Feb. 6, 2002; vol. 287, No. 5, pp. 628-640.

Novick, "Atherosclerotic Ischemic Nephropathy. Epidemiology and Clinical Considerations," *Urol. Clin. North Am.*, vol. 21, No. 2, pp. 195-200, May 1994. Abstract Only.

Paganini, et al., "Severity Scores and Outcomes With Acute Renal Failure in the ICU Setting," *Contrib Nephrol*, 2001; 132: 181-195.

Parfrey et al., "Contrast Material-Induced Renal Failure in Patients with Diabetes Mellitus, Renal Insufficiency, or Both," *N Engl J Med* 1989; 320:143-149.

Patel et al., "Intravenous Fenoldopam Infusion in Severe Heart Failure," *Cardiovasc Drugs Ther* , 1993;7:97-101.

Postma et al., "Treatment of Renal Artery Stenosis with Intra-Arterial Stents," *Ned Tijdschr Geneeskd*, vol. 142, No. 39, pp. 2132-2137, Sep. 26, 1998. Abstract Only.

Ramanathan, et al., Amerliorating Contrast-Induced Nephropathy, Journal of Invasive Cardiology, Nov. 2001, Retrieved from the Internet [Online]: www.invasivecardiology.comlfic_20011/jic_200111f6.html.

Rebeiz, et al., "Radiocontrast Nephropathy: a Time for Affirmative Action, *J Invasive Cardiology*," Jan. 2003; vol. 15, No. 1, pp. 23-24.

Rihal, et al., "Incidence and Prognostic Importance of Acute Renal Failure After Percutaneous Coronary Intervention," *Circulation*, (May 14, 2002),105:2259-2264.

Ritchie, et al., "Use of nonionic or Low Osmolar Contrast Agents in Cardiovascular Procedures," Retrieved from the Internet [Online] www.acc.org/clinical/position/72543.htm, Jan. 22, 2003.

Robinson, et al., "Congestive Heart Failure: Targeted Drug Therapy and Invasive Interventions", Retrieved from the Internet [Online] www.speroff.com/articieslTextbook/66_CHF2.htm, printed Sep. 4, 2002.

Rudnick et al., "Nephrotoxicity of Ionic and Noionic Contrast Media in 1196 Patients: A Randomized Trial," *Kidney International*, 1995;47:254-261.

Schwab et al., "Contrast Nephrotoxicity: A Randomized Controlled Trial of a Nonionic and an Ionic Radiographic Contrast Agent," *N Engl J Med*, 1989,320:149-153.

Seiter, H. et al., "Modified T-Catheter and its Use for Transvenous Hypothermic in Situ Perfusion in the Surgical Restoration of the Kidney with Staghorn Calculi," *Z. Urol Nephrol.*, vol. 76, No. 6 pp. 403-406, Jun. 1983. Abstract Only.

Shusterman et al., "Fenoldopam, But Not Nitroprusside, Improves Renal Function in Severely Hypertensive Patients With Impaired Renal Funcion," *Am J of Medicine*, 95:161-168 (1993).

Solomon et al., "Effects of Saline, Mannitol, and Furosemide on Accute Decreases in Renal Function Induced by Radiocontrast Agents.," *N Engl J Med* 1994; vol. 331 No. 21 pp. 1416-1420.

Stevens et al., "A Prospective Randomized Trial of Prevention Measures in Patients at High Risk for Contrast Nephropathy," *J Am Coli Cardiol*, 1999;33:403-411.

Strick et al., "Direct Measurement of Renal Medullary Blood Flow in the Dog," *Am J. Physiol*. 267 (Regulatory Integrative Compo Physiol. 36): R253-R2259, 1994.

Suehiro, et al., "Selective Renal Vasodilation and Active Renal Artery Perfusion Improve Renal Function in Dogs with Acute Heart Failure," *The Journal of Pharmacology and Experimental Therapeutics*, vol. 298, No. 3 pp. 1154-1160 (2001).

Taliercio et al., "Risks for Renal Dysfunction with Cardiac Angiography," *Annals of Internal Medicine*, 1986;104:501-504.

Thomas et al., "Glomerrular Filtration Dynamics During Renal Vasodilation with Acetylcholine in the Dog.," *Am. J. Physiol*. 244:F606-F611 (1983).

Thomas et al., "Influence of Bradykinin and Papaverine on Renal and Glomerular Hemodynamics in Dogs.," *Renal Physiology*, Basel 5:197-205 (1982).

Tumlin, et al., "Fenoldopam Mesylate Blocks Reductions in Renal Plasma Flow After Radiocontrast Dye Infusion," *Am Heart J* 2002;143:894-903.

UIC College of Pharmacy, "Is Fenoldopam (Corlopam) Useful for the Prevention Of Contrast Media Associated Nephrotoxicity?", Retrieved from the Internet [Online] www.uic.edu/pharmacy/services/di/fenoldopam.htm, Jan. 2003.

Umrani, et al., " Beneficial Effects Offenoldopam Treatment on Renal Function in Streptozotocin-Induced Diabetic Rats," *Clin Exp Hypertens*, Apr. 2002;24(3):207-19 Abstract Only.

Vari et al., "Induction, Prevention and Mechanisms of Contrast Media-Induced Acute Renal Failure," *Kidney International*, 1988; 33:669-707.

Walker et al., "Use of a Balloon-Tipped Perfusion Catheter for Renal Preservation During Suprarenal Abdominal Aortic Operations," *J. Vasc. Surg.*, vol. 2, No. 2, pp. 337-339, Mar. 1985. Abstract Only.

White et al., "Renal Artery Stent Placement: Utility in Lesions Difficult to Treat with Balloon Angioplasty," *J. Am. Coll. Cardiol.*, vol. 30, No. 6, pp. 1445-1450, Nov. 15, 1997. Abstract Only.

Williams et al., "Design and Testing of a High-FLO2 Autoperfusion Catheter: An Experimental Study," *J. Vasc. Interv. Radiol.*, vol. 3, No. 2, pp. 285-290, May 1992. Abstract Only.

Zacherl, et al. "Periarterial Papaverine Applications Improves Intraoperative Kidney Function During Laparoscopic Donor Nephrectomy", *Journal of Surgical Research* 103:268-271 (2002).

\* cited by examiner

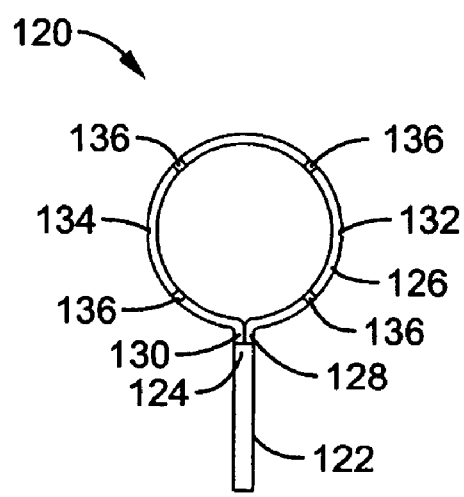 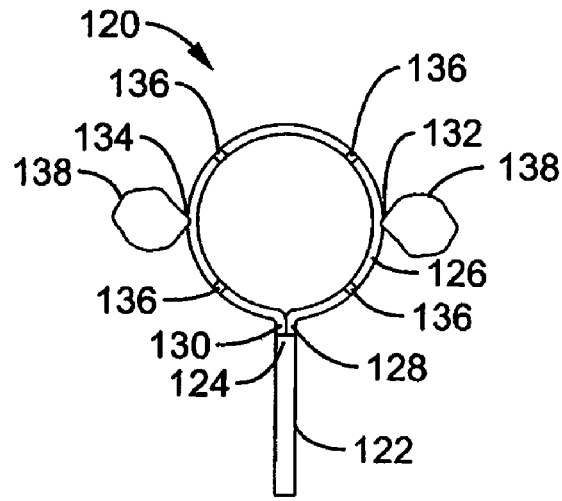
FIG. 10  FIG. 11
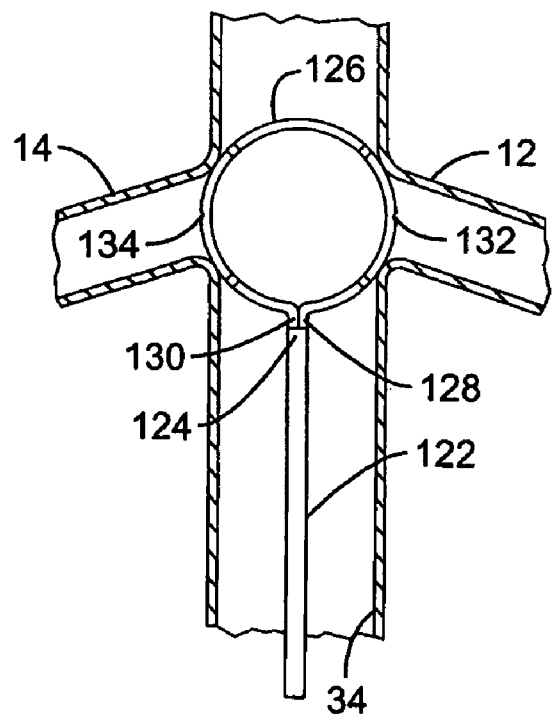
FIG. 12

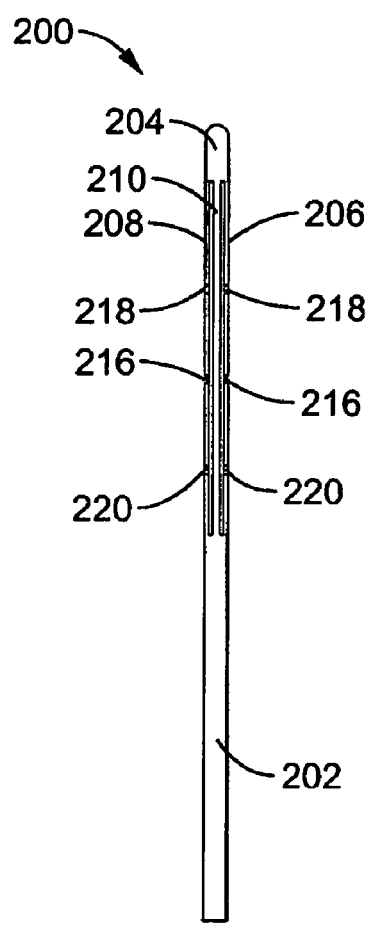 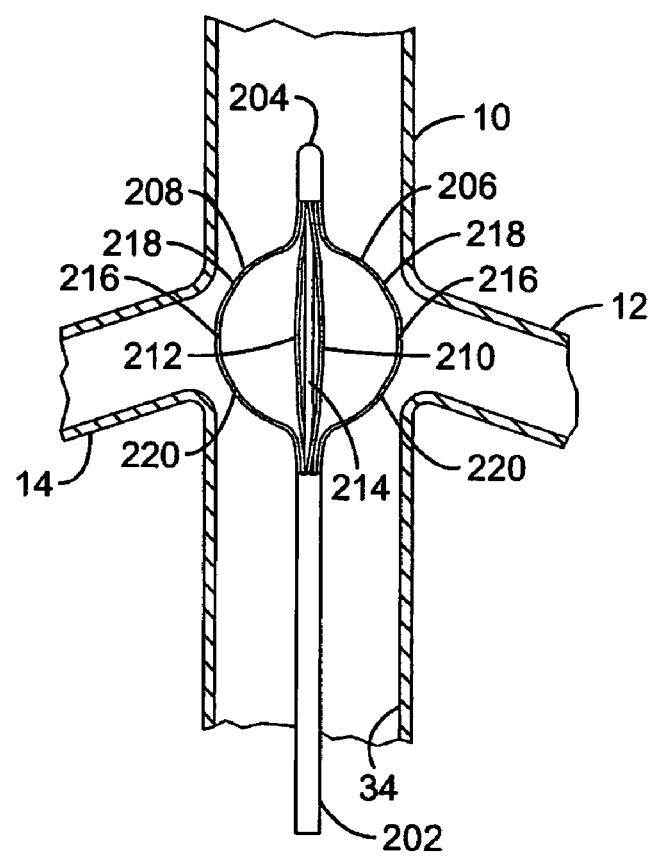
FIG. 19  FIG. 20

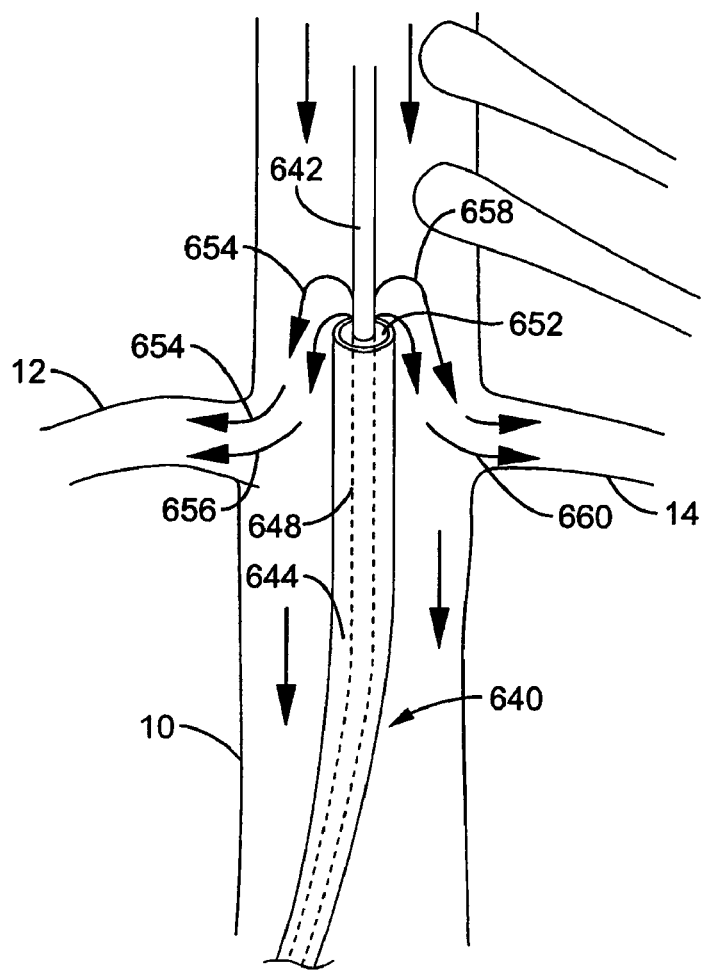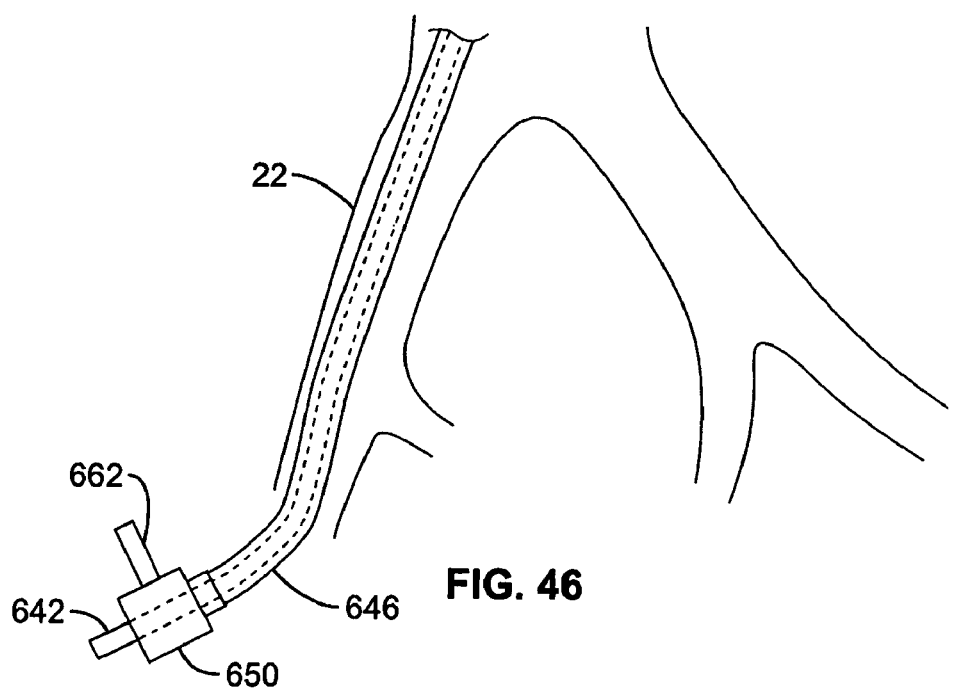
FIG. 46

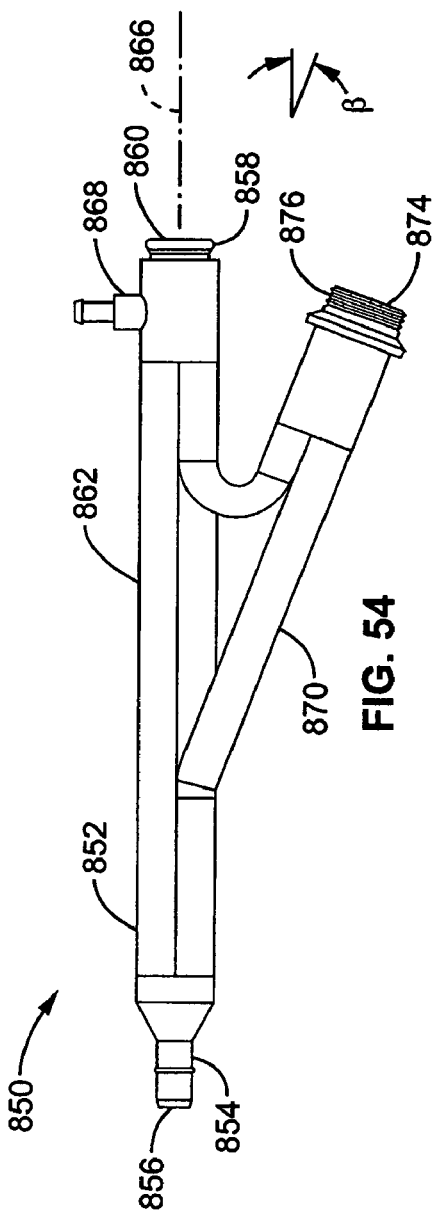
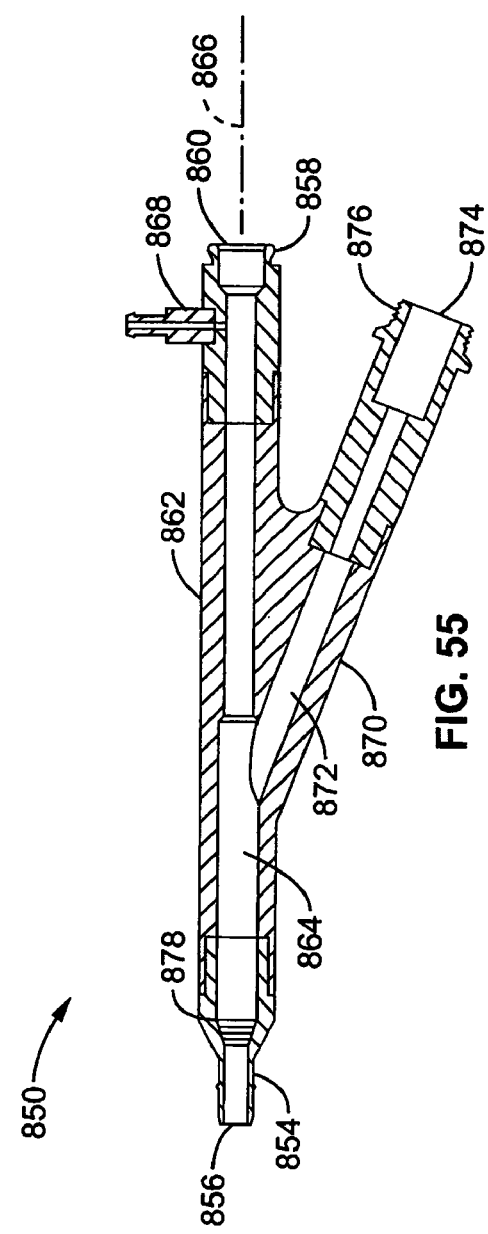
FIG. 54
FIG. 55

METHOD AND APPARATUS FOR INTRA-AORTIC SUBSTANCE DELIVERY TO A BRANCH VESSEL

CROSS-REFERENCES TO RELATED APPLICATIONS

This application is a continuation of PCT Patent Application No. PCT/US03/299995, filed Sep. 22, 2003, which claims priority from U.S. Provisional Application Ser. Nos.: 60/412,343, filed on Sep. 20, 2002; 60/412,476, filed on Sep. 20, 2002; 60/479,329, filed on Jun. 17, 2003; and 60/502,389, filed on Sep. 13, 2003. The full disclosure of each of the foregoing applications is hereby incorporated by reference.

BACKGROUND OF THE INVENTION

1. Field of the Invention

This invention pertains generally to medical device systems and methods for intra aortic fluid delivery into regions of the body. More specifically, it is related to intra aortic renal fluid delivery systems and methods.

2. Description of Related Art

Many different medical device systems and methods have been previously disclosed for locally delivering fluids or other agents into various body regions, including body lumens such as vessels, or other body spaces such as organs or heart chambers. Local "fluid" delivery systems may include drugs or other agents, or may even include locally delivering the body's own fluids, such as artificially enhanced blood transport (e.g. either entirely within the body such as directing or shunting blood from one place to another, or in extracorporeal modes such as via external blood pumps etc.). Local "agent" delivery systems are herein generally intended to relate to introduction of a foreign composition as an agent into the body, which may include drug or other useful or active agent, and may be in a fluid form or other form such as gels, solids, powders, gases, etc. It is to be understood that reference to only one of the terms fluid, drug, or agent with respect to local delivery descriptions may be made variously in this disclosure for illustrative purposes, but is not generally intended to be exclusive or omissive of the others; they are to be considered interchangeable where appropriate according to one of ordinary skill unless specifically described to be otherwise.

In general, local agent delivery systems and methods are often used for the benefit of achieving relatively high, localized concentrations of agent where injected within the body in order to maximize the intended effects there and while minimizing unintended peripheral effects of the agent elsewhere in the body. Where a particular dose of a locally delivered agent may be efficacious for an intended local effect, the same dose systemically delivered would be substantially diluted throughout the body before reaching the same location. The agent's intended local effect is equally diluted and efficacy is compromised. Thus systemic agent delivery requires higher dosing to achieve the required localized dose for efficacy, often resulting in compromised safety due to for example systemic reactions or side effects of the agent as it is delivered and processed elsewhere throughout the body other than at the intended target.

Various diagnostic systems and procedures have been developed using local delivery of dye (e.g. radiopaque "contrast" agent) or other diagnostic agents, wherein an external monitoring system is able to gather important physiological information based upon the diagnostic agent's movement or assimilation in the body at the location of delivery and/or at other locations affected by the delivery site. Angiography is one such practice using a hollow, tubular angiography catheter for locally injecting radiopaque dye into a blood chamber or vessel, such as for example coronary arteries in the case of coronary angiography, or in a ventricle in the case of cardiac ventriculography.

Other systems and methods have been disclosed for locally delivering therapeutic agent into a particular body tissue within a patient via a body lumen. For example, angiographic catheters of the type just described above, and other similar tubular delivery catheters, have also been disclosed for use in locally injecting treatment agents through their delivery lumens into such body spaces within the body. More detailed examples of this type include local delivery of thrombolytic drugs such as TPA™, heparin, cumadin, or urokinase into areas of existing clot or thrombogenic implants or vascular injury. In addition, various balloon catheter systems have also been disclosed for local administration of therapeutic agents into target body lumens or spaces, and in particular associated with blood vessels. More specific previously disclosed of this type include balloons with porous or perforated walls that elute drug agents through the balloon wall and into surrounding tissue such as blood vessel walls. Yet further examples for localized delivery of therapeutic agents include various multiple balloon catheters that have spaced balloons that are inflated to engage a lumen or vessel wall in order to isolate the intermediate catheter region from in-flow or out-flow across the balloons. According to these examples, a fluid agent delivery system is often coupled to this intermediate region in order to fill the region with agent such as drug that provides an intended effect at the isolated region between the balloons.

The diagnosis or treatment of many different types of medical conditions associated with various different systems, organs, and tissues, may also benefit from the ability to locally deliver fluids or agents in a controlled manner. In particular, various conditions related to the renal system would benefit a great deal from an ability to locally deliver of therapeutic, prophylactic, or diagnostic agents into the renal arteries.

Acute renal failure ("ARF") is an abrupt decrease in the kidney's ability to excrete waste from a patient's blood. This change in kidney function may be attributable to many causes. A traumatic event, such as hemorrhage, gastrointestinal fluid loss, or renal fluid loss without proper fluid replacement may cause the patient to go into ARF. Patients may also become vulnerable to ARF after receiving anesthesia, surgery, or a-adrenergic agonists because of related systemic or renal vasoconstriction. Additionally, systemic vasodilation caused by anaphylaxis, and anti-hypertensive drugs, sepsis or drug overdose may also cause ARF because the body's natural defense is to shut down, i.e., vasoconstrict, non-essential organs such as the kidneys. Reduced cardiac output caused by cardiogenic shock, congestive heart failure, pericardial tamponade or massive pulmonary embolism creates an excess of fluid in the body, which can exacerbate congestive heart failure. For example, a reduction in blood flow and blood pressure in the kidneys due to reduced cardiac output can in turn result in the retention of excess fluid in the patient's body, leading, for example, to pulmonary and systemic edema.

Previously known methods of treating ARF, or of treating acute renal insufficiency associated with congestive heart failure ("CHF"), involve administering drugs. Examples of such drugs that have been used for this purpose include, without limitation: vasodilators, including for example papavarine, fenoldopam mesylate, calcium-channel blockers, atrial natriuretic peptide (ANP), acetylcholine, nifedipine, nitroglycerine, nitroprusside, adenosine, dopamine, and theophylline; antioxidants, such as for example acetylcysteine; and diuretics, such as for example mannitol, or furosemide. However, many of these drugs, when administered in systemic doses, have undesirable side effects. Additionally, many of these drugs would not be helpful in treating other causes of ARF. While a septic shock patient with profound systemic vasodilation often has concomitant severe renal vasoconstriction, administering vasodilators to dilate the renal artery to a patient suffering from systemic vasodilation would compound the vasodilation system wide. In addition, for patients with severe CHF (e.g., those awaiting heart transplant), mechanical methods, such as hemodialysis or left ventricular assist devices, may be implemented. Surgical device interventions, such as hemodialysis, however, generally have not been observed to be highly efficacious for long-term management of CHF. Such interventions would also not be appropriate for many patients with strong hearts suffering from ARF.

The renal system in many patients may also suffer from a particular fragility, or otherwise general exposure, to potentially harmful effects of other medical device interventions. For example, the kidneys as one of the body's main blood filtering tools may suffer damage from exposed to high density radiopaque contrast dye, such as during coronary, cardiac, or neuro angiography procedures. One particularly harmful condition known as "radiocontrast nephropathy" or "RCN" is often observed during such procedures, wherein an acute impairment of renal function follows exposure to such radiographic contrast materials, typically resulting in a rise in serum creatinine levels of more than 25% above baseline, or an absolute rise of 0.5 mg/dl within 48 hours. Therefore, in addition to CHF, renal damage associated with RCN is also a frequently observed cause of ARF. In addition, the kidneys' function is directly related to cardiac output and related blood pressure into the renal system. These physiological parameters, as in the case of CHF, may also be significantly compromised during a surgical intervention such as an angioplasty, coronary artery bypass, valve repair or replacement, or other cardiac interventional procedure. Therefore, the various drugs used to treat patients experiencing ARF associated with other conditions such as CHF have also been used to treat patients afflicted with ARF as a result of RCN. Such drugs would also provide substantial benefit for treating or preventing ARF associated with acutely compromised hemodynamics to the renal system, such as during surgical interventions.

There would be great advantage therefore from an ability to locally deliver such drugs into the renal arteries, in particular when delivered contemporaneous with surgical interventions, and in particular contemporaneous with radiocontrast dye delivery. However, many such procedures are done with medical device systems, such as using guiding catheters or angiography catheters having outer dimensions typically ranging between about 4 French to about 12 French, and ranging generally between about 6 French to about 8 French in the case of guide catheter systems for delivering angioplasty or stent devices into the coronary or neurovascular arteries (e.g. carotid arteries). These devices also are most typically delivered to their respective locations for use (e.g. coronary ostia) via a percutaneous, translumenal access in the femoral arteries and retrograde delivery upstream along the aorta past the region of the renal artery ostia. A Seldinger access technique to the femoral artery involves relatively controlled dilation of a puncture hole to minimize the size of the intruding window through the artery wall, and is a preferred method where the profiles of such delivery systems are sufficiently small. Otherwise, for larger systems a "cut-down" technique is used involving a larger, surgically made access window through the artery wall.

Accordingly, an intra aortic renal agent delivery system for contemporaneous use with other retrogradedly delivered medical device systems, such as of the types just described above, would preferably be adapted to allow for such interventional device systems, in particular of the types and dimensions just described, to pass upstream across the renal artery ostia (a) while the agent is being delivered into the renal arteries, and (b) while allowing blood to flow downstream across the renal artery ostia, and (c) in an overall cooperating system that allows for Seldinger femoral artery access. Each one of these features (a), (b), or (c), or any sub-combination thereof, would provide significant value to patient treatment; an intra aortic renal delivery system providing for the combination of all three features is so much the more valuable.

Notwithstanding the clear needs for and benefits that would be gained from such intra aortic drug delivery into the renal system, the ability to do so presents unique challenges as follows.

In one regard, the renal arteries extend from respective ostia along the abdominal aorta that are significantly spaced apart from each other circumferentially around the relatively very large aorta. Often, these renal artery ostia are also spaced from each other longitudinally along the aorta with relative superior and inferior locations. This presents a unique challenge to deliver drugs or other agents into the renal system on the whole, which requires both kidneys to be fed through these separate respective arteries via their uniquely positioned and substantially spaced apart ostia. This becomes particularly important where both kidneys may be equally at risk, or are equally compromised, during an invasive upstream procedure—or, of course, for any other indication where both kidneys require renal drug delivery. Thus, an appropriate intra aortic delivery system for such indications would preferably be adapted to feed multiple renal arteries perfusing both kidneys.

In another regard, mere delivery of an agent into the natural, physiologic blood flow path of the aorta upstream of the kidneys may provide some beneficial, localized renal delivery versus other systemic delivery methods, but various undesirable results still arise. In particular, the high flow aorta immediately washes much of the delivered agent beyond the intended renal artery ostia. This reduces the amount of agent actually perfusing the renal arteries with reduced efficacy, and thus also produces unwanted loss of the agent into other organs and tissues in the systemic circulation (with highest concentrations directly flowing into downstream circulation).

In still a further regard, various known types of tubular local delivery catheters, such as angiographic catheters, other "end-hole" catheters, or otherwise, may be positioned with their distal agent perfusion ports located within the renal arteries themselves for delivering agents there, such as via a percutaneous translumenal procedure via the femoral arteries (or from other access points such as brachial arteries, etc.). However, such a technique may also provide less than completely desirable results.

For example, such seating of the delivery catheter distal tip within a renal artery may be difficult to achieve from within the large diameter/high flow aorta, and may produce harmful intimal injury within the artery. Also, where multiple kidneys must be infused with agent, multiple renal arteries must be cannulated, either sequentially with a single delivery device, or simultaneously with multiple devices. This can become unnecessarily complicated and time consuming and further compound the risk of unwanted injury from the required catheter manipulation. Moreover, multiple dye injections may be required in order to locate the renal ostia for such catheter positioning, increasing the risks associated with contrast agents on kidney function (e.g. RCN)—the very organ system to be protected by the agent delivery system in the first place. Still further, the renal arteries themselves, possibly including their ostia, may have pre-existing conditions that either prevent the ability to provide the required catheter seating, or that increase the risks associated with such mechanical intrusion. For example, the artery wall may be diseased or stenotic, such as due to atherosclerotic plaque, clot, dissection, or other injury or condition. Finally, among other additional considerations, previous disclosures have yet to describe an efficacious and safe system and method for positioning these types of local agent delivery devices at the renal arteries through a common introducer or guide sheath shared with additional medical devices used for upstream interventions, such as angiography or guide catheters. In particular, to do so concurrently with multiple delivery catheters for simultaneous infusion of multiple renal arteries would further require a guide sheath of such significant dimensions that the preferred Seldinger vascular access technique would likely not be available, instead requiring the less desirable "cut-down" technique.

In addition to the various needs for delivering agents into branch arteries described above, much benefit may also be gained from simply enhancing blood perfusion into such branches, such as by increasing the blood pressure at their ostia. In particular, such enhancement would improve a number of medical conditions related to insufficient physiological perfusion into branch vessels, and in particular from an aorta and into its branch vessels such as the renal arteries.

Certain prior disclosures have provided surgical device assemblies and methods intended to enhance blood delivery into branch arteries extending from an aorta. For example, intra-aortic balloon pumps (IABPs) have been disclosed for use in diverting blood flow into certain branch arteries. One such technique involves placing an IABP in the abdominal aorta so that the balloon is situated slightly below (proximal to) the branch arteries. The balloon is selectively inflated and deflated in a counterpulsation mode (by reference to the physiologic pressure cycle) so that increased pressure distal to the balloon directs a greater portion of blood flow into principally the branch arteries in the region of their ostia. However, the flow to lower extremities downstream from such balloon system can be severely occluded during portions of this counterpulsing cycle. Moreover, such previously disclosed systems generally lack the ability to deliver drug or agent to the branch arteries while allowing continuous and substantial downstream perfusion sufficient to prevent unwanted ischemia.

It is further noted that, despite the renal risks described in relation to radiocontrast dye delivery, and in particular RCN, in certain circumstances delivery of such dye or other diagnostic agents is indicated specifically for diagnosing the renal arteries themselves. For example, diagnosis and treatment of renal stenosis, such as due to atherosclerosis or dissection, may require dye injection into a subject renal artery. In such circumstances, enhancing the localization of the dye into the renal arteries may also be desirable. In one regard, without such localization larger volumes of dye may be required, and the dye lost into the downstream aortic flow may still be additive to impacting the kidney(s) as it circulates back there through the system. In another regard, an ability to locally deliver such dye into the renal artery from within the artery itself, such as by seating an angiography catheter there, may also be hindered by the same stenotic condition requiring the dye injection in the first place (as introduced above). Still further, patients may have stent-grafts that may prevent delivery catheter seating.

Notwithstanding the interest and advances toward delivering agents for treatment or diagnosis of organs or tissues, the previously disclosed systems and methods summarized immediately above generally lack the ability to effectively deliver agents from within a main artery and locally into substantially only branch arteries extending therefrom while allowing the passage of substantial blood flow and/or other medical devices through the main artery past the branches. This is in particular the case with previously disclosed renal treatment and diagnostic devices and methods, which do not adequately provide for local delivery of agents into the renal system from a location within the aorta while allowing substantial blood flow continuously downstream past the renal ostia and/or while allowing distal medical device assemblies to be passed retrogradedly across the renal ostia for upstream use. Much benefit would be gained if agents, such as protective or therapeutic drugs or radiopaque contrast dye, could be delivered to one or both of the renal arteries in such a manner.

Several more recently disclosed advances have included local flow assemblies using tubular members of varied diameters that divide flow within an aorta adjacent to renal artery ostia into outer and inner flow paths substantially perfusing the renal artery ostia and downstream circulation, respectively. Such disclosures further include delivering fluid agent primarily into the outer flow path for substantially localized delivery into the renal artery ostia. These disclosed systems and methods represent exciting new developments toward localized diagnosis and treatment of pre-existing conditions associated with branch vessels from main vessels in general, and with respect to renal arteries extending from abdominal aortas in particular.

However, such previously disclosed designs would still benefit from further modifications and improvements in order to: maximize mixing of a fluid agent within the entire circumference of the exterior flow path surrounding the tubular flow divider and perfusing multiple renal artery ostia; use the systems and methods for prophylaxis and protection of the renal system from harm, in particular during upstream interventional procedures; maximize the range of useful sizing for specific devices to accommodate a wide range of anatomic dimensions between patients; and optimize the construction, design, and inter-cooperation between system components for efficient, atraumatic use.

A need still exists for improved devices and methods for delivering agents principally into the renal arteries of a patient from a location within the patient's aorta adjacent the renal artery ostia along the aorta wall while at least a portion of aortic blood flow is allowed to perfuse downstream across the location of the renal artery ostia and into the patient's lower extremities.

A need still exists for improved devices and methods for substantially isolating first and second portions of aortic blood flow at a location within the aorta of a patient adjacent the renal artery ostia along the aorta wall, and directing the first portion into the renal arteries from the location within the aorta while allowing the second portion to flow across the location and downstream of the renal artery ostia into the patient's lower extremities. There is a further benefit and need for providing passive blood flow along the isolated paths and without providing active in-situ mechanical flow support to either or both of the first or second portions of aortic blood flow.

A need still exists for improved devices and methods for locally delivering agents such as radiopaque dye or drugs into a renal artery from a location within the aorta of a patient adjacent the renal artery's ostium along the aorta wall, and without requiring translumenal positioning of an agent delivery device within the renal artery itself or its ostium.

A need still exists for improved devices and methods for bilateral delivery of fluids or agents such as radiopaque dye or drugs simultaneously into multiple renal arteries feeding both kidneys of a patient using a single delivery device and without requiring translumenal positioning of multiple agent delivery devices respectively within the multiple renal arteries themselves.

A need still exists for improved devices and methods for delivery of fluids or agents into the renal arteries of a patient from a location within the patient's aorta adjacent the renal artery ostia along the aorta wall, and while allowing other treatment or diagnostic devices and systems, such as angiographic or guiding catheter devices and related systems, to be delivered across the location.

A need still exists for improved devices and methods for delivering fluids or agents into the renal arteries from a location within the aorta of a patient adjacent to the renal artery ostia along the aorta wall, and other than as a remedial measure to treat pre-existing renal conditions, and in particular for prophylaxis or diagnostic procedures related to the kidneys.

A need still exists for improved devices and methods for delivery of fluids or agents into the renal arteries of a patient in order to treat, protect, or diagnose the renal system adjunctive to performing other contemporaneous medical procedures such as angiograms other translumenal procedures upstream of the renal artery ostia.

A need still exists for improved devices and methods for delivering both an intra aortic drug delivery system and at least one adjunctive distal interventional device, such as an angiographic or guiding catheter, through a common delivery sheath.

A need also still exists for improved devices and methods for delivering both an intra aortic drug delivery system and at least one adjunctive distal interventional device, such as an angiographic or guiding catheter, through a single access site, such as a single femoral arterial puncture.

A need also still exists for improved devices and methods for treating, and in particular preventing, ARF, and in particular relation to RCN or CHF, by locally delivering renal protective or ameliorative drugs into the renal arteries, such as contemporaneous with radiocontrast injections such as during angiography procedures.

A need still exists for improved devices to deliver fluid agents bilaterally to both sides of the renal system from within the aorta system.

A need still exists for improved devices to deliver fluid agents bilaterally to both sides of the renal system without requiring cannulation of the renal arteries themselves.

A need also exists for improved devices to deliver fluid agents bilaterally to both sides of the renal system without substantially occluding, isolating, or diverting blood flow within the abdominal aorta.

In addition to these particular needs for selective fluid delivery into a patient's renal arteries via their ostia along the aorta, other similar needs also exist for fluid delivery into other branch vessels or lumens extending from other main vessels or lumens, respectively, in a patient.

BRIEF SUMMARY OF THE INVENTION

These present embodiments therefore generally relate to intra aortic renal drug delivery systems generally from a position proximal to the renal arteries themselves; however, it is contemplated that these systems and methods may be suitably modified for use in other anatomical regions and for other medical conditions without departing from the broad scope of various of the aspects illustrated by the embodiments. For example, intra aortic fluid delivery according to various of these embodiments benefits from particular dimensions, shapes, and constructions for the subject devices herein described. However, suitable modifications may be made to deliver fluids to other multi-lateral branch structures from main body spaces or lumens, such as for example in other locations within the vasculature (e.g. right and left coronary artery ostia, fallopian tubes stemming from a uterus, or gastrointestinal tract.

One aspect of the invention is a local renal infusion system for treating a renal system in a patient from a location within the abdominal aorta associated with first and second flow paths within an outer region of abdominal aortic blood flow generally along the abdominal aorta wall and into first and second renal arteries, respectively, via their corresponding first and second renal ostia along an abdominal aorta wall in the patient. This system includes a local injection assembly with first and second injection ports. The local injection assembly is adapted to be positioned at the location with the first and second injection ports at first and second respective positions, respectively, corresponding with the first and second flow paths. The local injection assembly is also adapted to be fluidly coupled to a source of fluid agent externally of the patient when the local injection assembly is positioned at the location. Accordingly, the local injection assembly is adapted to inject a volume of fluid agent from the source, through the first and second injection ports at the first and second positions, respectively, and bi-laterally into the first and second renal arteries, also respectively. This assembly is in particular adapted to accomplish such localized bilateral renal delivery via the respective corresponding first and second renal ostia and without substantially altering abdominal aorta flow along the location.

According to certain further modes of this aspect, the local injection assembly is adapted to inject the volume of fluid agent into the first and second flow paths such that the injected volume flows substantially only into the first and second renal arteries without substantially diverting, occluding, or isolating one region of aortic blood flow with respect to the first or second regions of aortic blood flow.

Another further mode also includes a delivery member with a proximal end portion and a distal end portion with a longitudinal axis. The local injection assembly comprises first and second injection members with first and second injection ports, respectively, and is adapted to extend from the distal end portion of the delivery member and is adjustable between a first configuration and a second configuration as follows. The local injection assembly in the first configuration is adapted to be delivered by the delivery member to the location. The local injection assembly at the location is adjustable from the first configuration to the second configuration such that the first and second first injection members are radially extended from the longitudinal axis with the first and second injection ports located at the first and second positions, respectively, at the first and second flow paths.

According to another mode, the local injection assembly includes an elongate body that is adapted to be positioned within the outer region. The first and second injection ports are spaced at different locations around the circumference of the elongate body such that the first and second injection ports are adapted to inject the volume of fluid agent in first and second different respective directions laterally from the elongate body and generally into the first and second flow paths, respectively.

According to one embodiment of this mode, a positioner cooperates with the elongate body and is adapted to position the elongate body within the outer region at the location. In one variation of this embodiment, the positioner is coupled to the elongate body and is adjustable from a first configuration to a second configuration. The positioner in the first configuration is adapted to be delivered to the location with the elongate body. The positioner at the location is adapted to be adjusted from the first configuration to the second configuration that is biased to radially extend from the elongate body relative to the first configuration and against the abdominal aorta wall with sufficient force so as to deflect the orientation of the elongate body into the outer region. Further to this variation the positioner may also beneficially be a partial loop-shaped member that extends with first and second legs from the elongate body. In the first configuration at the location the partial loop-shaped member has a first orientation with respect to the elongate body and is adapted to be delivered to the location. In the second configuration at the location the partial loop-shaped member has a second orientation that is radially extended from the elongate body relative to the first orientation. In still further features according to this variation, the partial loop-shaped member is adjusted to the first configuration when subject to deformation force away from a memory shape, and is self-adjustable from the first configuration to the second configuration by material recovery of the partial loop-shaped member from the first configuration toward the memory shape. The first and second legs may be extendable from the elongate body through first and second extension ports, such that in the first configuration the first and second legs are withdrawn into the elongate body, and in the second configuration the first and second legs are extended from the elongate body through the first and second extension ports, respectively.

In another embodiment, a control member is coupled to the partial loop-shaped member and also to the elongate body, and is adapted to adjust the looped-shape member between the first and second configurations by manipulating the position of the control member.

In still a further embodiment, the positioner comprises a plurality of partial loop-shaped members such as described above.

In another mode of this aspect of the invention, the local injection assembly further includes an elongate body with a longitudinal axis and that is adapted to be positioned at the location. The first and second injection members in the first configuration have first radial positions relative to the longitudinal axis, and in the second configuration have second radial positions. The second radial positions are radially extended from the longitudinal axis relative to the first radial position.

In one embodiment of this mode, the first and second injection members are located on opposite respective sides of the elongate body around a circumference of the elongate body. In one variation of this embodiment, each of the first and second injection members extends between proximal and distal respective locations on each of the opposite respective sides of the elongate body, and in the second configuration the first and second injection members are biased outward from the elongate body between the respective proximal and distal respective locations.

In another embodiment, the local injection assembly is in the form of a generally loop-shaped member, such that the first and second injection members comprise first and second regions along the loop-shaped member, and whereas the first and second injection ports are located on each of the first and second regions. The loop-shaped member in the first configuration has a first diameter between the first and second injection ports such that the loop-shaped member is adapted to be delivered to the location. The loop-shaped member in the second configuration has a second diameter between the first and second injection ports that is greater than the first diameter and is sufficient such that the first and second positions generally correspond with first and second flow paths within the outer region, respectively. According to one variation of this embodiment, the local injection assembly in the second configuration for the loop-shaped member includes a memory shape. The loop-shaped member is adjustable from the second configuration to the first configuration within a radially confining outer delivery sheath. The loop-shaped member is adjustable from the first configuration to the second configuration by removing it from radial confinement outside of the outer delivery sheath.

In another mode, the local injection assembly comprises a plurality of n injection members, wherein n is an integer that is greater than two. Further to this mode, n injection ports are located on the n injection members, respectively. Each of the n injection members is adapted to be positioned at the location such that the n injection ports are located at n unique respective positions within the outer region. The local injection assembly is adapted to be oriented at the location such that n minus two of the plurality of injection members are oriented with the corresponding n minus two injection ports against the abdominal aorta wall, and such that the remaining two injection members of the plurality are oriented such that the two corresponding injection ports are at the first and second positions. Accordingly, the remaining two injection members are the first and second injection members, and the remaining two injection ports on the two remaining injection members are the first and second injection ports.

In one embodiment of this mode, each of the plurality of injection ports at its respectively unique position within the outer region is adapted to be fluidly coupled simultaneously with the source of fluid agent externally of the body. The n minus two injection ports are adapted to be substantially prevented by the abdominal wall from injecting a substantial volume of fluid agent from the source and into the outer region. The remaining two injection ports are adapted to inject a substantial volume of fluid agent from the source and into the first and second renal ostia, respectively, such that local injection of fluid agent from the source is substantially isolated to the two injection ports.

In another embodiment, in the first configuration at the location the n injection members are positioned at n generally unique radially collapsed positions around a circumference having a first diameter around a longitudinal axis of the abdominal aorta at the location. In the second configuration at the location the n injection members are positioned at n generally unique radially expanded positions around a circumference having a second diameter around the longitudinal axis that is greater than the first outer diameter and that is sufficient to position the respective n injection ports at the n respective positions, respectively.

According to another mode, each of the first and second injection members includes an infusion passageway with an array of n injection regions, wherein n is an integer. Each array of n injection regions is adapted to be coupled to the source of fluid agent outside the body. The first and second injection members are adapted to be oriented at the location such that x of the n respective injection regions of each array are positioned within the outer region and in fluid communication with the respective renal ostium, and such that y of the respective injection regions of each array are against the abdominal aorta wall such that they are substantially prevented by the abdominal aorta wall from injecting a volume of fluid agent into the outer region. Accordingly, the first injection port includes at least one of the x injection regions along the first injection member. The second injection port includes at least one of the x injection regions along the second injection member. Further to this description, in general x is a positive number that is not greater than n, and n is equal to x plus y.

In a further mode of the present aspect, first and second markers located along first and second injection members, respectively, at locations generally corresponding with the first and second injection ports. Each of the first and second markers is adapted to indicate to an operator externally of the patient the locations of the first and second injection ports to assist their delivery to the first and second positions, respectively. In particular beneficial embodiments, the first and second markers are radiopaque and provide guidance under fluoroscopy. In a further embodiment, the first and second injection members extend distally from the delivery member from a bifurcation location, and a proximal marker is located at the bifurcation location.

In another mode, a the delivery member is provided that is an introducer sheath with a proximal end portion and a distal end portion that is adapted to be positioned at the location with the proximal end portion of the introducer sheath extending externally from the patient. The delivery member includes a delivery passageway extending between a proximal port assembly along the proximal end portion of the introducer sheath and a distal port assembly along the distal end portion of the introducer sheath. The injection assembly is adapted to be slideably engaged within the introducer sheath, and is adjustable between first and second longitudinal positions. The first and second injection members are located within the delivery passageway in the first longitudinal position and are extended distally through the distal port and from the distal end portion in the second longitudinal position. In a further embodiment of this mode, the distal end portion of the introducer sheath includes a distal tip and a delivery marker at a location corresponding with the distal tip such that the delivery marker is adapted to indicate the relative position of the distal tip within the abdominal aorta at the location. In one further embodiment, the distal port assembly has first and second ports through which the first and second delivery members are extended during adjustment to the second configuration.

In another further embodiment, a catheter body is provided with a proximal end portion and a distal end portion that is adapted to be positioned at the location when the proximal end portion of the catheter body extends externally from the patient. The first and second injection members are coupled to and extend distally from the distal end portion of the catheter body. The proximal port assembly of the introducer sheath comprises a single proximal port, and the first and second injection members and distal end portion of the catheter body are adapted to be inserted into the delivery passageway through the single proximal port.

According to another mode, the system further includes a proximal coupler assembly that is adapted to be fluidly coupled to a source of fluid agent externally of the patient, and also to the first and second injection ports at the first and second positions, respectively.

In one embodiment, the proximal coupler assembly comprises first and second proximal couplers. The first proximal coupler is fluidly coupled to the first injection port, and the second proximal coupler is fluidly coupled to the second injection port. In one variation of this embodiment, a first elongate body extends between the first proximal coupler and the first injection member, and with a first fluid passageway coupled to the first proximal coupler and the first injection port; a second elongate body extends between the second proximal coupler and the second injection member, and with a second fluid passageway coupled to the second coupler and the second injection port. In another variation, the proximal coupler assembly includes a single common coupler that is fluidly coupled to each of the first and second injection ports via a common fluid passageway. According to one feature that may be employed per this variation, an elongate body extends between the single common coupler and the first and second injection members. The elongate body has at least one delivery passageway fluidly coupled to the single common coupler and also to the first and second injection ports.

According to still a further mode of this aspect of the invention, the system further includes a source of fluid agent that is adapted to be coupled to the local injection assembly. The fluid agent may comprises one, or combinations of, the following: saline; a diuretic, such as Furosemide or Thiazide; a vasopressor, such as Dopamine; a vasodilator; another vasoactive agent; Papaverine; a Calcium-channel blocker; Nifedipine; Verapamil; fenoldapam mesylate; a dopamine DA1 agonist; or analogs or derivatives, or combinations or blends, thereof.

Another mode includes a vascular access system with an elongate tubular body with at least one lumen extending between a proximal port assembly and a distal port that is adapted to be positioned within a vessel having translumenal access to the location. The system per this mode also includes a percutaneous translumenal interventional device that is adapted to be delivered to an intervention location across the location while the local injection assembly is at the location. The local injection assembly and percutaneous translumenal interventional device are adapted to be delivered percutaneously to the location and intervention location, respectively, through the vascular access device, and are also adapted to be simultaneously engaged within the vascular access device.

In one embodiment, the percutaneous translumenal interventional device comprises an angiographic catheter. In another, the percutaneous translumenal interventional device is a guiding catheter. In another regard, the interventional device may be between about 4 French and about 8 French.

In another embodiment, the proximal port assembly includes first and second proximal ports. The percutaneous translumenal interventional device is adapted to be inserted into the elongate body through the first proximal port. The first and second ports of the injection assembly are adapted to be inserted into the elongate body through the second proximal port.

According to another mode, the local injection assembly includes a fluid reservoir and the first injection port is fluidly coupled to the fluid reservoir. The fluid reservoir is adjustable between a first condition, a second condition, and a third condition. In the first condition the fluid reservoir is adapted to be delivered to the location with the first injection port at the first position at the location. The fluid reservoir at the location is adapted to be fluidly coupled to a source of fluid agent located externally of the patient. The fluid reservoir at the location is adjustable from the first condition to the second condition such that the first volume from the source is delivered into the fluid reservoir. The local injection assembly at the location is further adjustable from the second condition to the third condition wherein the fluid reservoir discharges the first volume of fluid agent through the injection port at the position. The injected first volume of fluid agent is adapted to flow principally into the first flow path.

Another aspect is a local infusion system for locally delivering a volume of fluid agent from a source located externally of a patient and into a location within a body space of a patient. This system includes a delivery member with a proximal end portion and a distal end portion with a longitudinal axis, and a local injection assembly comprising first and second injection members with first and second injection ports, respectively. The local injection assembly extends from the distal end portion of the delivery member and is adjustable between a first configuration and a second configuration as follows. The local injection assembly in the first configuration is adapted to be delivered by the delivery member to the location. The local injection assembly at the location is adjustable from the first configuration to the second configuration such that the first and second first injection members are radially extended from the longitudinal axis with the first and second injection ports located at first and second relatively unique positions, respectively, at the location. The first and second injection ports at the first and second respective positions are adapted to be fluidly coupled to a source of fluid agent externally of the patient and to inject a volume of fluid agent into the patient at the first and second positions, also respectively, at the location.

Another aspect of the invention is a local infusion system with a local injection assembly comprising an injection member with an injection port and a fluid reservoir fluidly coupled to the injection port. The local injection assembly is adjustable between a first condition, a second condition, and a third condition as follows. In the first condition the local injection assembly is adapted to be delivered to a location within a body space of a patient with the injection port and fluid reservoir at a position within the location. The injection port at the position is adapted to be fluidly coupled to a source of fluid agent located externally of the patient. The local injection assembly at the location is adjustable from the first condition to the second condition such that a volume of fluid agent from the source is delivered via the injection port into the fluid reservoir. The local injection assembly at the location is further adjustable from the second condition to the third condition wherein the fluid reservoir discharges the volume of fluid agent into the location at the position.

Another aspect of the invention is a local infusion system for delivering a volume of fluid agent from a source located externally of a patient and into a portion of an outer region within and generally along a wall of a body space at a location along the body space in the patient. The system includes a local injection assembly with an injection port, and a flow isolation assembly that cooperates with the local injection assembly as follows. The local injection assembly is adapted to be delivered to the location with the injection port at a position within the portion of the outer region. The injection port at the position is adapted to be fluidly coupled to a source of fluid agent located externally of the patient and to inject a volume of fluid agent from the source into the portion of the outer region of the body space. The flow isolation assembly is adjustable between a first condition and a second condition as follows. The flow isolation assembly in the first condition is adapted to be delivered to the location. The flow isolation assembly at the location is adjustable from the first condition to a second condition that is adapted to isolate the injected volume of fluid agent to flow substantially within the portion of the outer region along the location. The portion is located along only a part of the circumference of the outer region that is less than all of the circumference.

Another aspect of the invention is a local renal infusion system for treating a renal system in a patient from a location within the abdominal aorta associated with abdominal aortic blood flow into first and second renal arteries via respective first and second renal ostia having unique relative locations along the abdominal aorta wall. This system includes in one regard a delivery catheter with an elongate body having a proximal end portion, a distal end portion with a distal tip that is adapted to be delivered across the location and to a delivery location that is upstream of the location while the proximal end portion is located externally of the patient, and a delivery lumen extending between a proximal port along the proximal end portion and a distal port along the distal end portion. A local injection assembly is also provided with an injection port. The local injection assembly is adapted to be delivered at least in part by the elongate body to the location such that the injection port is at a position within the location while the distal tip of the delivery catheter is at the delivery position. The injection port at the location is adapted to be fluidly coupled to a source of fluid agent located externally of the patient and to inject a volume of fluid agent from the source into abdominal aorta at the location such that the injected volume flows substantially into the first and second arteries via the first and second renal ostia, respectively.

Another aspect of the invention is a method for treating a renal system in a patient from a location within the abdominal aorta associated with abdominal aortic blood flow into first and second renal arteries via respective first and second renal ostia having unique relative locations along the abdominal aorta wall. This method includes in one regard delivering a delivery catheter with an elongate body having a proximal end portion and a distal end portion with a distal tip across the location and to a delivery location that is upstream of the location while the proximal end portion is located externally of the patient. The method further includes delivering a local injection assembly that includes an injection port at least in part by the elongate body to the location such that the injection port is at a position within the location while the distal tip of the delivery catheter is at the delivery position. The injection port at the location is fluidly coupled to a source of fluid agent located externally of the patient. A volume of fluid agent from the source is injected through the injection port and into abdominal aorta at the location such that the injected volume flows substantially into the first and second arteries via the first and second renal ostia, respectively.

Another aspect of the invention is a method for treating a renal system in a patient from a location within the abdominal aorta associated with abdominal aortic blood flow into first and second renal arteries via their respective first and second renal ostia, respectively, at unique respective locations along the abdominal aorta wall. This method includes: positioning a local injection assembly at the location with first and second injection ports at first and second unique respective positions at the location. Also includes is fluidly coupling the local injection assembly at the location to a source of fluid agent externally of the patient. A further step includes simultaneously injecting a volume of fluid agent from the source through the first and second injection ports at the first and second positions and principally into the first and second renal arteries, respectively.

Another aspect of the invention is a method for treating a renal system in a patient from a location within the abdominal aorta associated with abdominal aortic blood flow into each of first and second renal arteries via first and second renal ostia, respectively, at unique respective locations along the abdominal aorta wall. This method includes positioning a local injection assembly at the location, and fluidly coupling to the local injection assembly at the location to a source of fluid agent externally of the patient. Also included is injecting a volume of fluid agent from the source and into the abdominal aorta at the location in a manner such that the injected fluid flows principally into the first and second renal arteries via the first and second renal ostia, respectively, and without substantially occluding or isolating a substantial portion of an outer region of aortic blood flow along a circumference of the abdominal aorta wall and across the location.

Another aspect of the invention is a method for treating a renal system in a patient from a location within the abdominal aorta associated with abdominal aortic blood flow into each of first and second renal arteries via first and second renal ostia, respectively, at unique respective locations along the abdominal aorta wall. This method aspect includes positioning a delivery member within an abdominal aorta of a patient, and delivering with the delivery member a local injection assembly having first and second injection members with first and second injection ports, respectively, in a first configuration to the location. Also included is adjusting the local injection assembly between the first configuration and a second configuration at the location. Further to this method, in the second configuration the local injection assembly extends from the distal end portion of the delivery member with the first and second first injection members radially extended relative to each other across a portion of the abdominal aorta at the location and with the first and second injection ports located at first and second relatively unique positions, respectively, at the location. A further mode of this aspect is fluidly coupling the first and second injection ports at the first and second respective positions to a source of fluid agent externally of the patient, and injecting a volume of fluid agent into the first and second renal arteries via their respective first and second renal ostia from the first and second positions, respectively.

Another aspect of the invention is a method for treating a renal system in a patient from a location within the abdominal aorta associated with abdominal aortic blood flow into a renal artery via a renal ostium located along the abdominal aorta wall. This method includes delivering a local injection assembly comprising an injection member with a fluid reservoir and an injection port in a first condition to the location with the injection port at a position at the location. Also included is fluidly coupling the fluid reservoir at the location to a source of fluid agent located externally of the patient. Further steps include adjusting the local injection assembly at the location from the first condition to a second condition such that a volume of fluid agent from the source is delivered into the fluid reservoir, and adjusting the local injection assembly at the location from the second condition to a third condition wherein the fluid reservoir discharges the volume of fluid agent through the injection port at the position. Accordingly, the injected volume of fluid agent is adapted to flow principally into the renal artery via the renal ostium.

Another method aspect of the invention is a method for treating a renal system in a patient from a location within the abdominal aorta associated with abdominal aortic blood flow into a renal artery via a renal ostium located along the abdominal aorta wall. This method includes delivering a local injection assembly with an injection port to the location with the injection port at a position within a portion of an outer region of the abdominal aortic blood flow generally along the abdominal aorta wall at the location. Further included is fluidly coupling the injection port at the position to a source of fluid agent located externally of the patient and to inject a volume of fluid agent from the source into the portion of the outer region. Further steps are delivering a flow isolation assembly in a first condition to the location, adjusting the flow isolation assembly at the location from the first condition to a second condition, and isolating the injected volume of fluid agent to flow substantially within the portion of the outer region along the location with the flow isolation assembly in the second condition. According to this method, the portion is located along only a part of the circumference of the outer region that is less than all of the circumference.

Another aspect of the invention is a method for providing local therapy to a renal system in a patient from a location within the abdominal aorta associated with first and second flow paths within an outer region of abdominal aortic blood flow generally along the abdominal aorta wall and into first and second renal arteries, respectively, via their corresponding first and second renal ostia along an abdominal aorta wall in the patient. This method includes positioning a local injection assembly at the location with first and second injection ports at first and second respective positions, respectively, corresponding with the first and second flow paths. Also included is fluidly coupling the local injection assembly to a source of fluid agent externally of the patient when the local injection assembly is positioned at the location, and injecting a volume of fluid agent from the source, through the first and second injection ports at the first and second positions, respectively, and bi-laterally into the first and second renal arteries, also respectively, via the respective corresponding first and second renal ostia without substantially altering abdominal aorta flow along the location.

Further modes of these various method aspects include beneficially enhancing renal function with the injected volume of fluid agent. This may include in particular injecting the volume of fluid agent into the location while performing an interventional procedure at an intervention location within a vasculature of the patient. In one embodiment, this further includes injecting the volume of fluid agent during a period when a volume of radiocontrast dye injection is within the patient's vasculature, and such that the fluid agent is adapted to substantially prevent RCN in response to the radiocontrast dye injection. According to a further beneficial variation, the method includes treating acute renal failure with the injected volume of fluid agent.

Whereas each of these aspects, modes, embodiments, variations, and features is considered independently beneficial and are not to be required in combination with the others, nevertheless the various combinations and sub-combinations thereof as would be apparent to one of ordinary skill are further considered within the intended scope as further independently beneficial aspects of the invention.

Further aspects of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only:

FIG. 10 is an anterior view of another bifurcated drug infusion catheter embodiment with an infusion ring shown in an expanded configuration.

FIG. 11 is an anterior view of the bifurcated fluid infusion catheter embodiment shown in FIG. 10, shown in one mode of operation discharging medication.

FIG. 12 is an anterior view of the bifurcated drug infusion catheter of FIGS. 10 and 11, and shows it disposed within an abdominal aorta adjacent to the renal arteries.

FIG. 19 is a plan view of another fluid infusion catheter with positioning struts shown in a collapsed configuration.

FIG. 20 is an anterior view of the fluid infusion catheter of FIG. 19, and shows the struts disposed within an abdominal aorta adjacent to the renal arteries in an expanded configuration.

FIG. 46 is a perspective view of another catheter assembly with a drug infusion introducer sheath disposed within an abdominal aorta adjacent to the renal arteries.

FIG. 54 illustrates a proximal coupler system for positioning aortic fluid delivery systems adjunctively with other medical devices.

FIG. 55 illustrates a section view of the proximal coupler system as shown in FIG. 54.

DETAILED DESCRIPTION OF THE INVENTION

Figure 3:
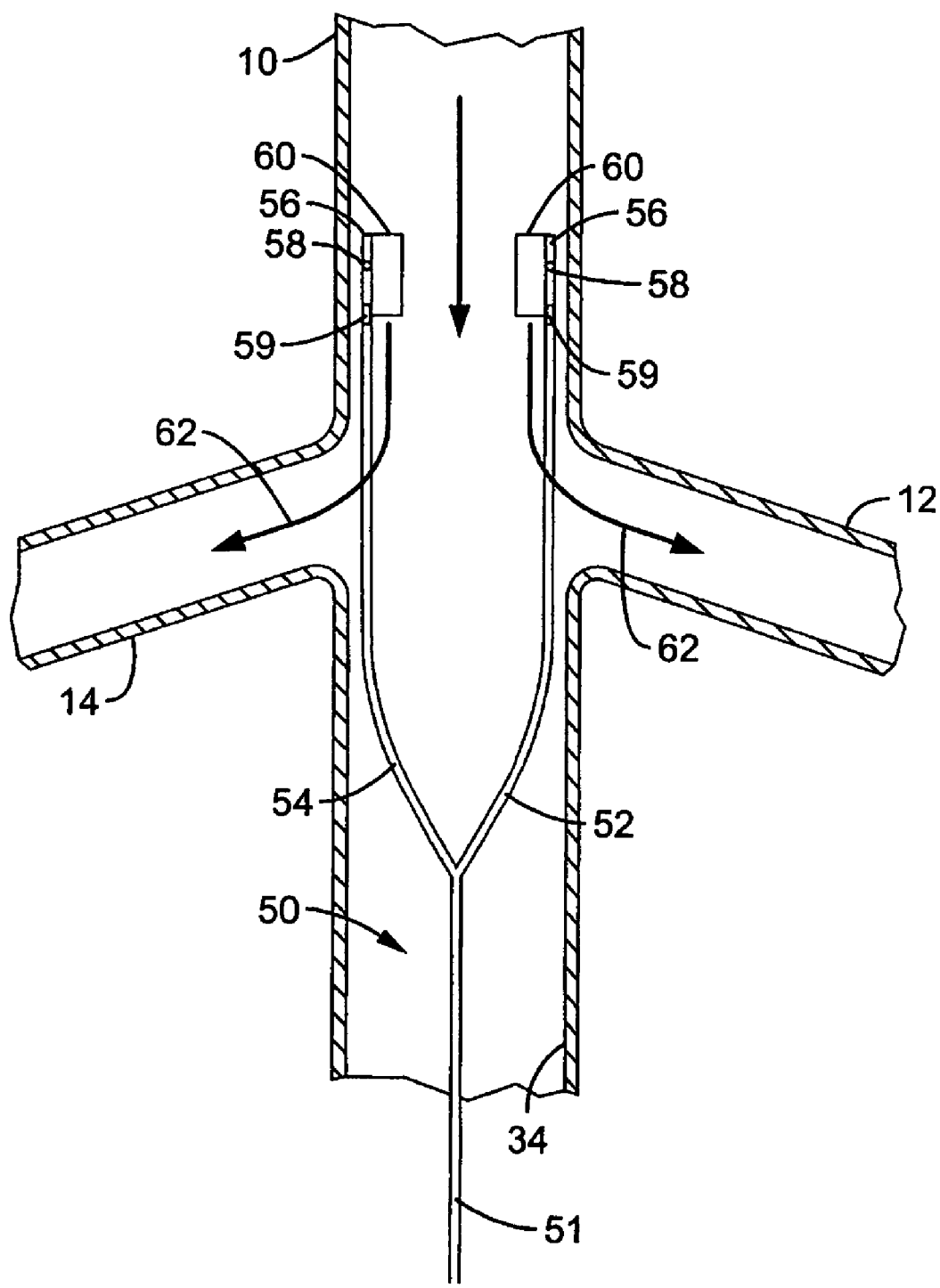
FIG. 3 is an anterior view of an embodiment of a bifurcated fluid infusion catheter disposed within an abdominal aorta in the vicinity of the renal arteries.
Figure 59:
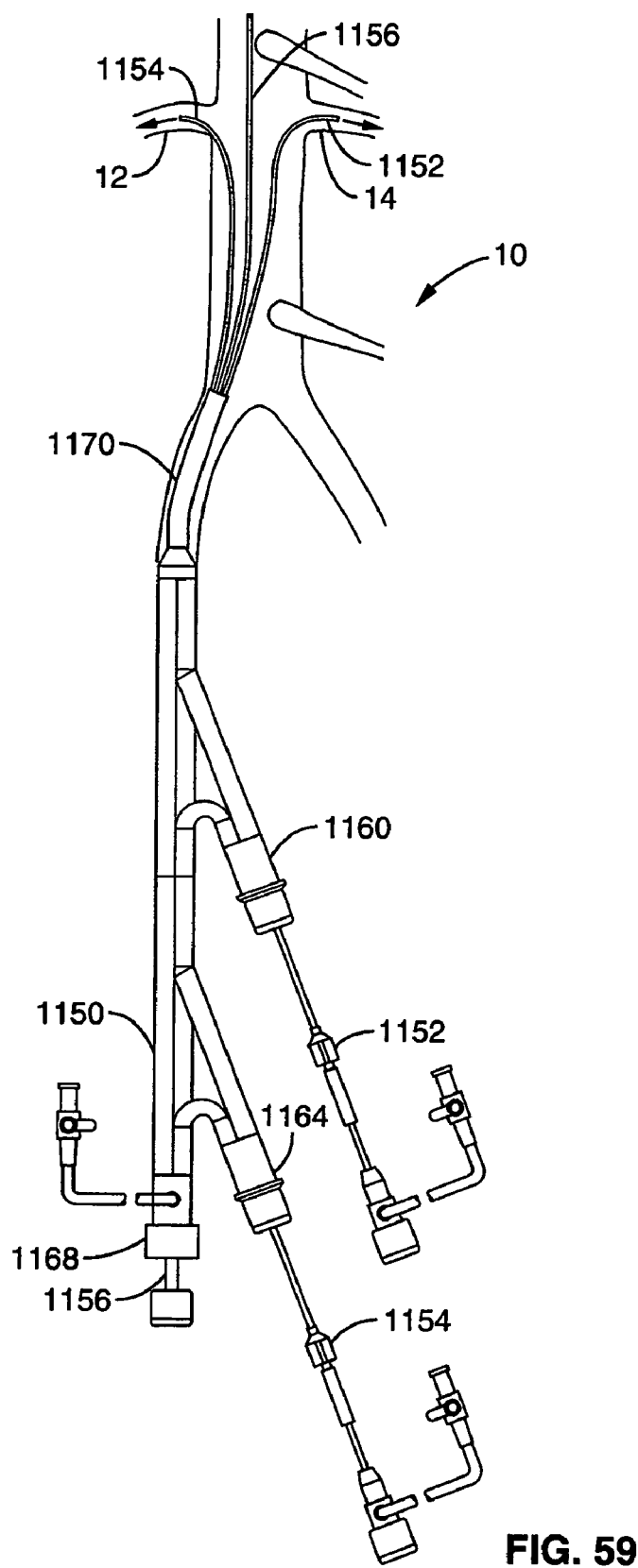
FIG. 59 is a stylized illustration of a double Y assembly with two local fluid delivery systems and an intervention catheter in an aorta system.

Referring more specifically to the drawings, for illustrative purposes the present invention is embodied in the apparatus generally shown in FIG. 3 through FIG. 59. It will be appreciated that the apparatus may vary as to configuration and as to details of the parts, and that the method may vary as to the specific steps and sequence, without departing from the basic concepts as disclosed herein.

The description herein provided relates to medical material delivery systems and methods in the context of their relationship in use within a patient's anatomy. Accordingly, for the purpose of providing a clear understanding, the term proximal should be understood to mean locations on a system or device relatively closer to the operator during use, and the term distal should be understood to mean locations relatively further away from the operator during use of a system or device. These present embodiments below therefore generally relate to local renal drug delivery generally from the aorta; however, it is contemplated that these systems and methods may be suitably modified for use in other anatomical regions and for other medical conditions without departing from the broad scope of various of the aspects illustrated by the embodiments.

In general, the disclosed material delivery systems will include a fluid delivery assembly, a proximal coupler assembly and one or more elongated bodies, such as tubes or catheters. These elongated bodies may contain one or more lumens and generally consist of a proximal region, a mid-distal region, and a distal tip region. The distal tip region will typically have means for delivering a material such as a fluid agent. Radiopaque markers or other devices may be coupled to the specific regions of the elongated body to assist introduction and positioning.

The material delivery system is intended to be placed into position by a physician, typically either an interventionalist (cardiologist or radiologist) or an intensivist, a physician who specializes in the treatment of intensive-care patients. The physician will gain access to a femoral artery in the patient's groin, typically using a Seldinger technique of percutaneous vessel access or other conventional method.

For additional understanding, further more detailed examples of other systems and methods for providing local renal drug delivery are variously disclosed in the following published references: WO 00/41612 to Keren et al.; and WO 01/083016 to Keren et al. The disclosures of these references are herein incorporated in their entirety by reference thereto. Moreover, various combinations with, or modifications according to, various aspects of the present embodiments as would be apparent to one of ordinary skill upon review of this disclosure together with these references are also considered within the scope of invention as described by the various independently beneficial embodiments described below.

The invention is also related to subject matter disclosed in other Published International Patent Applications as follows: WO 00/41612 to Libra Medical Systems, published Jul. 20, 2000; and WO 01/83016 to Libra Medical Systems, published Nov. 8, 2001. The disclosures of these Published International Patent Applications are also herein incorporated in their entirety by reference thereto.

Figure 1:
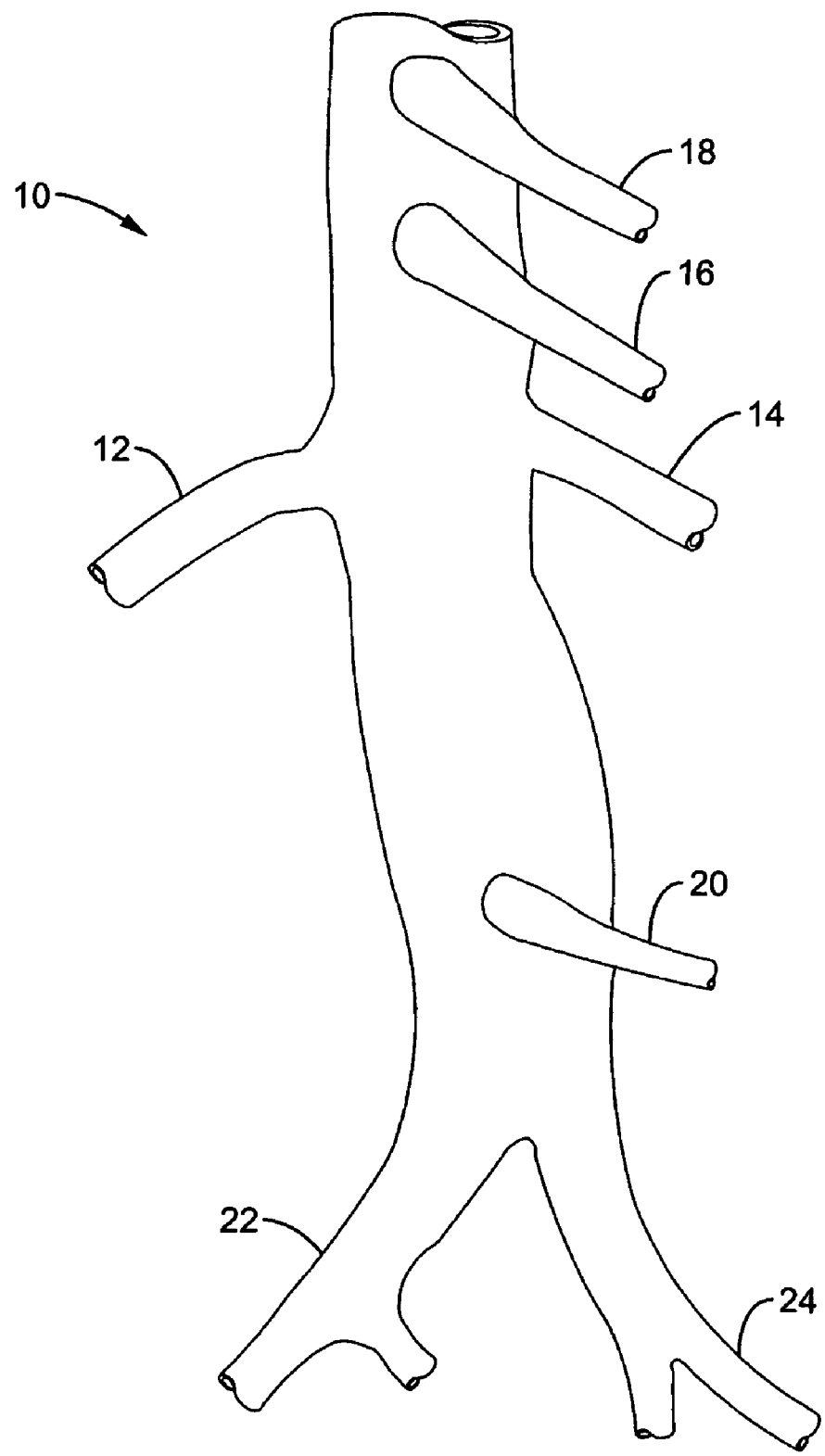
FIG. 1 is an anterior perspective view of an abdominal aorta in the generally vicinity of the renal arteries.

Referring initially to FIG. 1, an abdominal aorta is shown and is generally designated 10. As shown, a right renal artery 12 and a left renal artery 14 extend from the abdominal aorta 10. A superior mesenteric artery 16 extends from the abdominal aorta 10 above the renal arteries 12, 14. Moreover, a celiac artery 18 extends from the abdominal aorta 10 above the superior mesenteric artery 16. FIG. 1 also shows that an inferior mesenteric artery 20 extends from the abdominal aorta 10 below the renal arteries 12, 14. Further, as shown in FIG. 1, the abdominal aorta 10 branches into a right iliac artery 22 and a left iliac artery 24. It is to understood that each embodiments of the present invention described in detail below can be used to deliver a drug or other fluid solution locally into the renal arteries 12, 14. Each of the below-described embodiments can be advanced through one of the iliac arteries 22, 24 and into the abdominal aorta 10 until the general vicinity of the renal arteries 12, 14 is reached.

Figure 2:
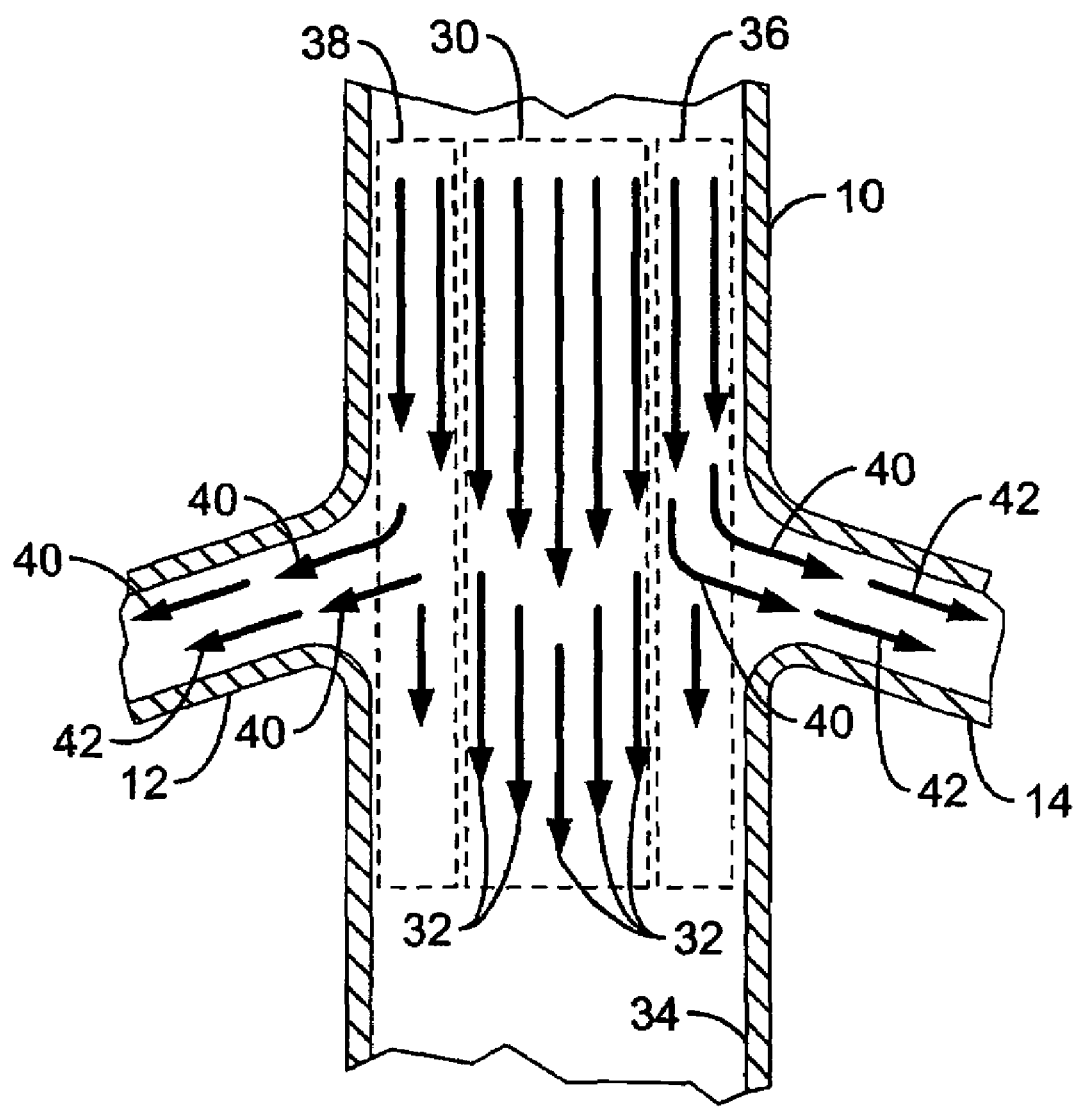
FIG. 2 is a cross-section view of an abdominal aorta taken in the vicinity of the renal arteries showing the general blood flow patterns through the abdominal aorta and the renal arteries.

FIG. 2 shows a schematic cross-section of the abdominal aorta 10 taken in the immediate vicinity of the renal arteries 12, 14. FIG. 2 shows the natural flow patterns through the abdominal aorta 10 and the natural flow patterns from the abdominal aorta 10 into the renal arteries 12, 14. As shown, the flow down the abdominal aorta 10 maintains a laminar flow pattern. Moreover, the flow stream near the middle of the abdominal aorta 10, as indicated by dashed box 30, continues down the abdominal aorta 10, as indicated by arrows 32, and does not feed into any of the side branches, e.g., the renal arteries 12, 14. As such, a drug solution infusion down the middle of the abdominal aorta flow stream can be ineffective in obtaining isolated drug flow into the renal arteries 12, 14.

Conversely, the flow stream along an inner wall 34 of the abdominal aorta 10, as indicated by dashed box 36 and dashed box 38, contains a natural laminar flow stream into the branching arteries, e.g., the renal arteries 12, 14, as indicated by arrows 40, 42. In general, the flow stream 32 is of a higher velocity than flow stream 40 along wall 34 of aorta 10. It is to be understood that near the boundaries of dashed box 36,38 with dashed box 30 the flow stream can contain flow streams into the branching arteries 12, 14—as well as down the abdominal aorta 10.

Further, the ostia of renal arteries 12, 14 are positioned to receive substantial blood flow from the blood flow near the posterior wall 34 of aorta 10 as well as the side walls. In other words, blood flow 40 in dashed boxes 36, 38 together is greater than blood flow 32 in dashed box 30 when along the posterior wall of aorta 10 relative to blood flow in the center of aorta 10 as shown in FIG. 2. Thus, drug infusion above renal arteries 12, 14 and along the posterior wall of aorta 10 will be effective in reaching renal arteries 12, 14.

Accordingly, in order to maximize the flow of a drug solution into the renal arteries using the natural flow patterns shown in FIG. 2, it is beneficial to provide a device, as described in detail below, that is adapted to selectively infuse a drug solution along the side wall or posterior wall of the abdominal aorta 10 instead of within the middle of the abdominal aorta 10 or along the anterior wall.

As described in much greater detail below, it is beneficial to infuse a drug solution above the renal arteries 12, 14 at two locations along the wall 34 of the abdominal aorta 10 spaced approximately one-hundred and eighty degrees (180) apart from each other.

Referring now to FIG. 3, a first embodiment of a bifurcated drug infusion catheter is shown and is generally designated 50. As shown, the bifurcated drug infusion catheter 50 includes a central catheter body 51 that splits into a first bifurcated portion 52 and a second bifurcated portion 54. Each bifurcated portion 52, 54 includes a free end 56 in which an infusion port 58 is formed. Each free end 56 further includes a radio-opaque marker band 59. Also, an infusion assembly 60 is attached to the free end 56 of each bifurcated portion 52, 54 around the infusion port 58. Details concerning the construction of each infusion assembly 60 are described below.

It can be appreciated that the bifurcated drug infusion catheter 50 shown in FIG. 3, places a bifurcated portion 52, 54 on the inner wall 34 of the abdominal aorta 10 generally immediately upstream from the level of the renal arteries 12, 14. The infusion ports 58 are positioned inside an infusion assembly 60, described below, that releases a drug solution during the systolic phase of blood flow in which the blood flow within the abdominal aorta 10 is more predictable and more closely tracks the wall 34 of the abdominal aorta 10 into the renal arteries 12, 14, as indicated by arrows 62.

It can be further appreciated that the infusion of a drug solution from the bifurcated portions 52, 54 of the bifurcated drug infusion catheter 50, when positioned adjacent to the inner wall 34 of the abdominal aorta 10, results in a greater percentage of the drug solution entering the renal arteries 12, 14 than systemic injection. However, "mixing" into the center of the abdominal aorta 10 can still take place, e.g., during the diastolic phase of blood flow through the abdominal aorta 10. Thus, releasing a drug solution from a properly positioned bifurcated drug infusion catheter 50 during the systolic phase, when a more uniform flow pattern is present, can result in a majority of the drug solution flowing into the renal arteries 12, 14. Further, a "passive" infusion assembly, as described below, allows the bifurcated drug infusion catheter 50 to work in a beneficial manner with improved efficiency and reduced complexity. While it is technically feasible to pulse the injection of a drug with an electro mechanical device driven by an ECG signal it is beyond the scope of the desired level of complexity desired.

Figure 4:
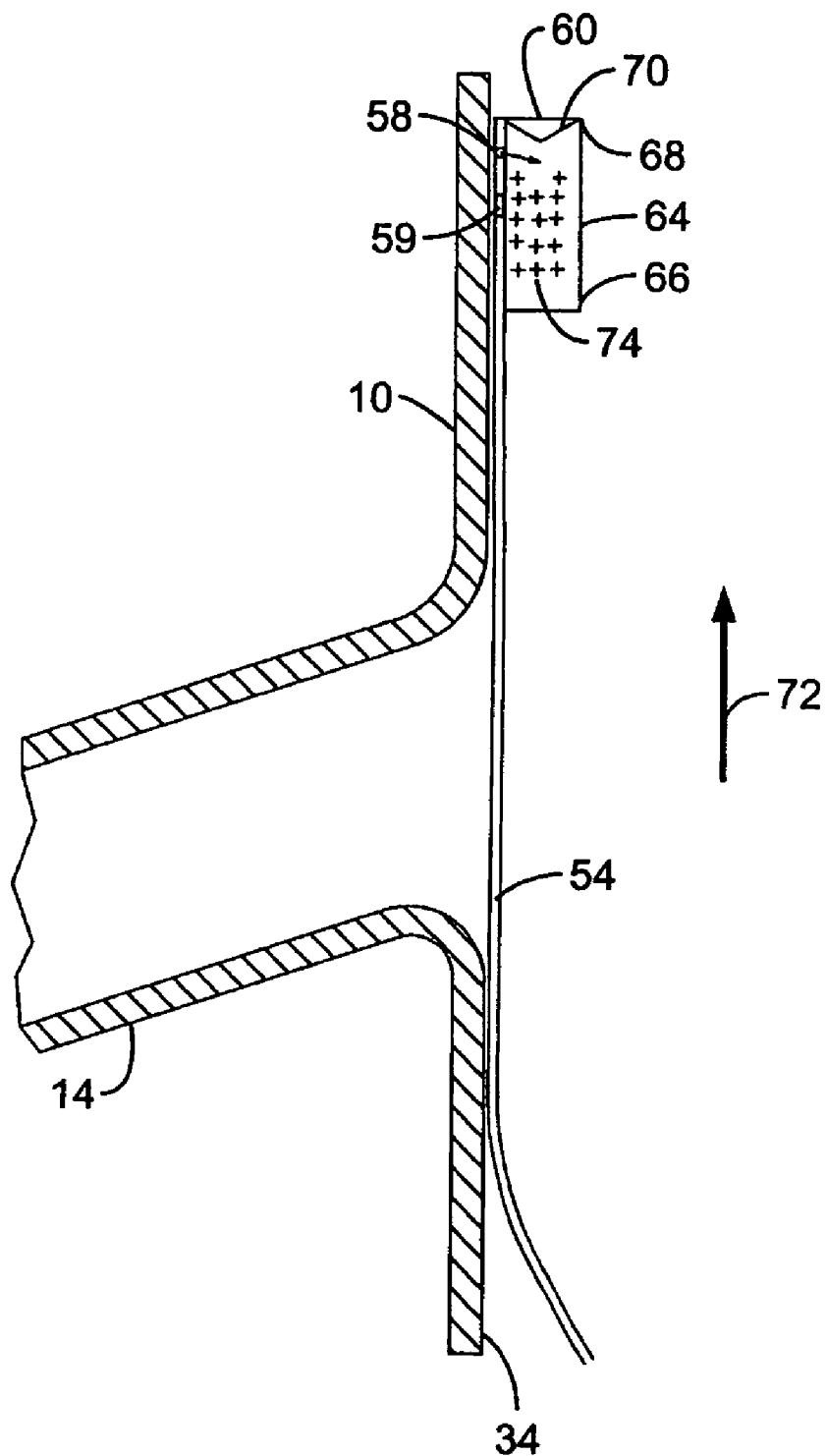
FIG. 4 is a detailed view of one portion of the fluid infusion assembly shown in FIG. 3 in a diastole configuration.
Figure 5:
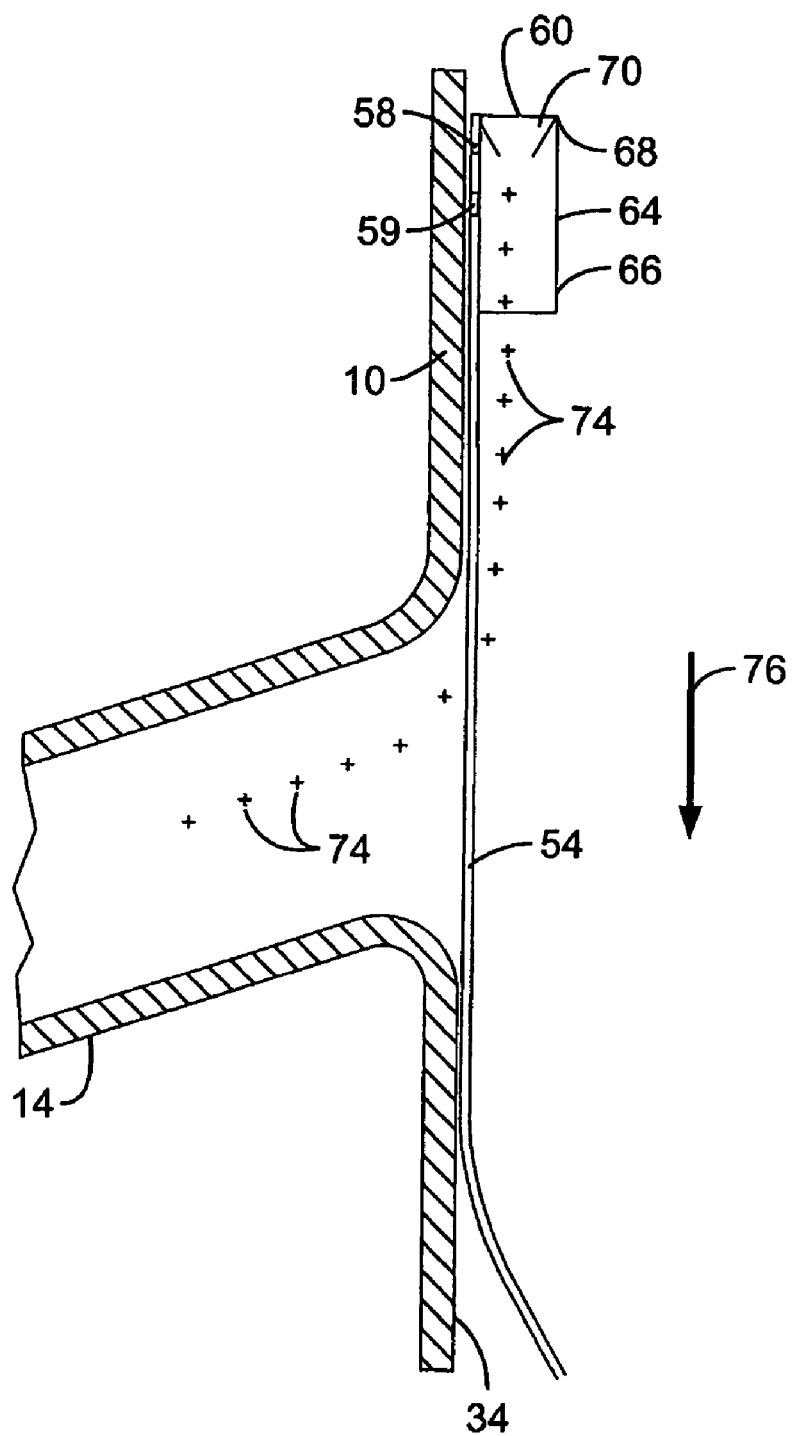
FIG. 5 is a detailed view of the portion of the fluid infusion assembly shown in FIG. 4, except shows it in a systole configuration.

Referring now to FIG. 4 and FIG. 5, details concerning the construction of one embodiment of the infusion assembly 60 attached to each bifurcated portion 52, 54 of the bifurcated drug infusion catheter 50 are shown. As shown, the infusion assembly 60 includes a collapsible tube 64 having a proximal end 66 and a distal end 68. Further, a one way check valve 70 is installed in the distal end 68 of the collapsible tube 64.

FIG. 4 shows the infusion assembly 60 in the diastole configuration in which the one way check valve 70 is closed. It can be appreciated that during diastole, as indicated by arrow 72, a drug solution 74 trickling from the infusion port 58 can collect in the tube 64 where it is prevented from mixing into the middle of the abdominal aorta 10. However, during systole, as indicated by arrow 76 in FIG. 5, the infusion assembly 60 moves to the systole configuration, wherein blood flow opens the one way check valve 70 and the drug solution 74 flows out of the infusion assembly 60, along the wall 34 of the abdominal aorta 10, and into the renal artery 14.

Figure 6:
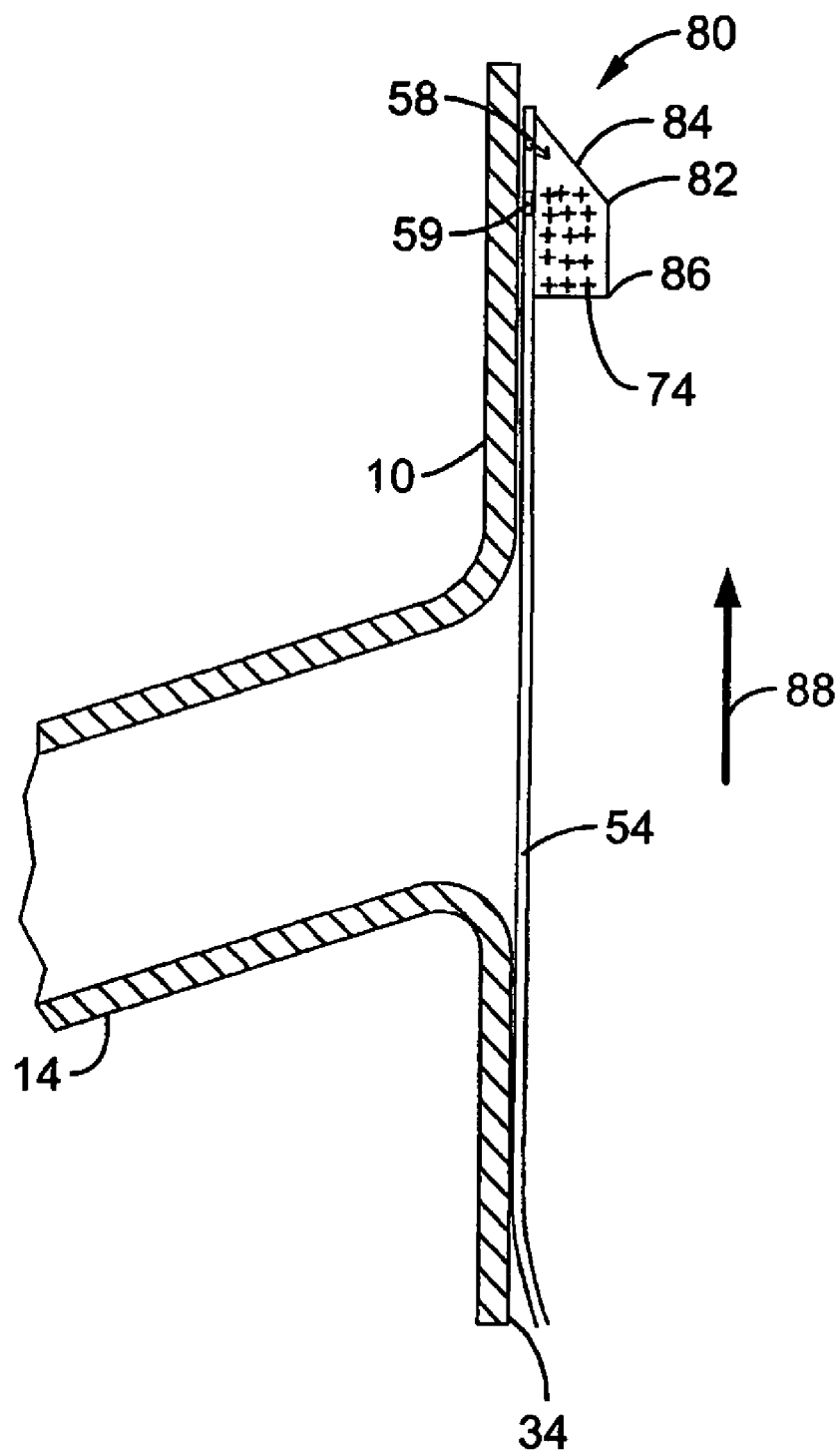
FIG. 6 is a detailed view of another fluid infusion assembly in a diastole configuration.
Figure 7:
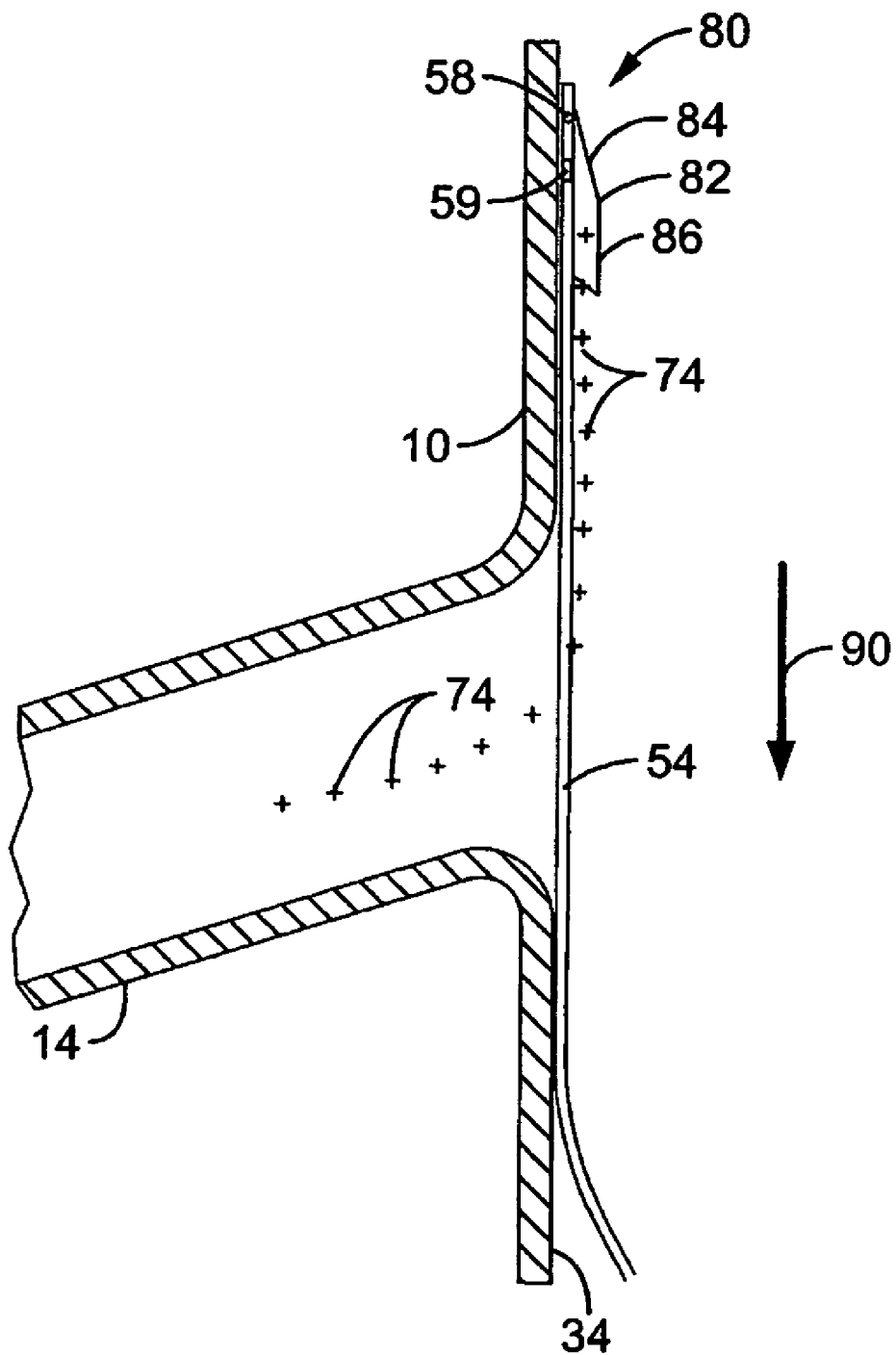
FIG. 7 is a detailed view of the fluid infusion assembly shown in FIG. 6, except shows it in a systole configuration.

FIG. 6 and FIG. 7 show another embodiment of an infusion assembly, designated 80, that can be used in conjunction with the bifurcated drug infusion catheter 50 shown in FIG. 3. As shown in FIG. 6 and FIG. 7, the infusion assembly 80 includes a collapsible sock 82 having a distal end 84 and a proximal end 86.

During diastole, as indicated by arrow 88 in FIG. 6, the infusion assembly 80 is the diastole configuration wherein the drug solution 74 from the infusion port 58 can collect in the collapsible sock 82. Within the collapsible sock 82, during diastole, the drug solution 74 is prevented from mixing into the middle of the abdominal aorta 10. However, during systole, as indicated by arrow 90 in FIG. 7, the infusion assembly 80 moves to the systole configuration, wherein the blood flow causes the collapsible sock 82 to collapse and the drug solution 74 flows out of the infusion assembly 80, along the wall 34 of the abdominal aorta 10, and into the renal artery 14.

It can be appreciated that the bifurcated drug infusion catheter 50, shown in FIG. 3, can be used with either of the above-described infusion assemblies 60, 80. Further, during use, the bifurcated drug infusion catheter 50 can be introduced through a long 8 or 9 French (Fr) diameter introducer sheath positioned near the renal arteries 12, 14. Thereafter, partially withdrawing the introducer sheath can expose the free ends 56 of the bifurcated portions 52, 54 of the bifurcated drug infusion catheter 50 until separation can be detected, e.g., at approximately one-half (½) of the diameter of the abdominal aorta 10. Viewing in an A-P plane the bifurcated drug infusion catheter 50 can be rotated back and forth until the marker bands 59 are in the most lateral position, i.e., when the distance between the marker bands 59 appears to be the greatest. Then, the longitudinal position of the bifurcated drug infusion catheter 50 can be fine tuned. A user, e.g., a physician, can continue to withdraw the introducer sheath until the free ends 56 of the bifurcated drug infusion catheter 50 are in contact with the inner wall 34 of the aorta 10. It can be appreciated that the bifurcated drug infusion catheter 50 can be held in place within the abdominal aorta 10 by a spring force separating the bifurcated portions 52, 54 of the bifurcated drug infusion catheter 50. It can be further appreciated that each of the embodiments shown in FIGS. 3-7 are relatively easy to position, present limited surface area, and minimize flow stagnation. Moreover, upstream interventions may be performed, e.g. PCA.

Figure 8:
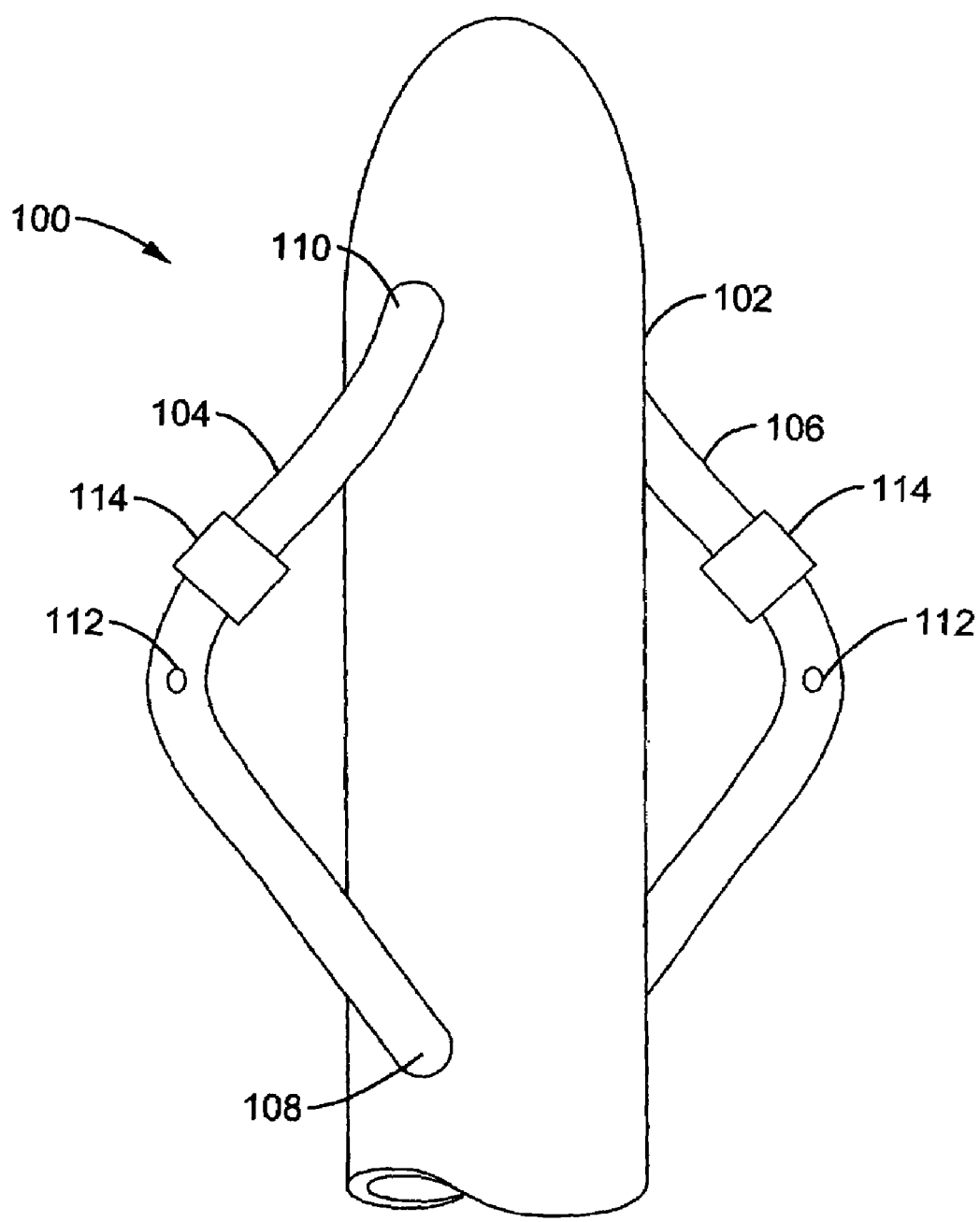
FIG. 8 is a perspective view of another form of bifurcated drug infusion catheter in an expanded configuration.
Figure 9:
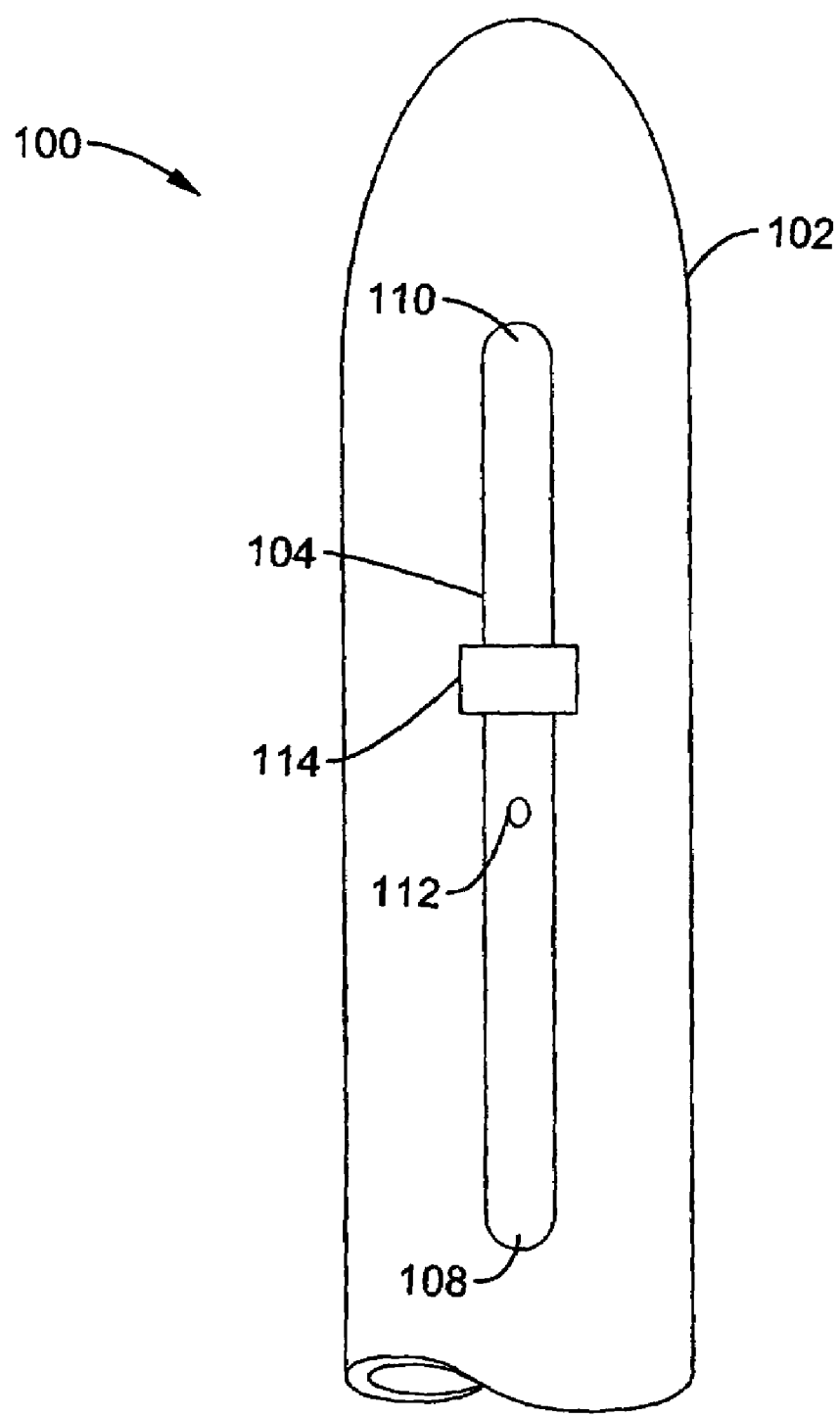
FIG. 9 is a side plan view of the bifurcated drug infusion catheter shown in FIG. 8, except shows the catheter in a collapsed configuration.

Referring now to FIG. 8 and FIG. 9, another embodiment of a bifurcated drug infusion catheter is shown and is designated 100. As shown, the bifurcated drug infusion catheter 100 includes a central catheter tube 102. In one beneficial embodiment, catheter tube 102 is multilumen. A first infusion tube 104 and a second infusion tube 106, made of a flexible material such as nickel-titanium tubing, are coupled to and extend from the central catheter tube 102 at approximately one-hundred and eighty degrees (180°) from each other. Each infusion tube 104, 106 includes a proximal end 108 and a distal end 110. In one beneficial embodiment, the distal ends 110 of each infusion tube 104, 106 are coupled to the central catheter tube 102 and the proximal ends 108 enter catheter tube 102 and continue proximally to a proximal coupler assembly (not shown). It is to be understood that during drug infusion, a drug solution can flow from the central catheter tube 102 and through each infusion tube 104, 106, e.g., from the proximal end 108 to the distal end 110, or from the distal end 110 to the proximal end 108, but drug solution principally exits through ports 112.

FIG. 8 and FIG. 9 show the infusion tubes 104, 106 in an expanded configuration and a retracted configuration respectively. In one embodiment, the infusion tubes 104, 106 are advanced distally from a proximal coupler assembly (not shown) causing each infusion tube 104, 106 to bow outward in the expanded configuration shown in FIG. 8. When infusion tubes 104, 106 are retracted proximally from a proximal coupler assembly (not shown), they straighten in the retracted configuration shown in FIG. 9.

FIG. 8 and FIG. 9 further show that each infusion tube 104, 106 is formed with an infusion port 112 from which a drug solution can flow during drug infusion. Moreover, each infusion tube 104, 106 includes a marker band 114 to assist in properly positioning the bifurcated catheter tube 100 within the abdominal aorta 10 (FIG. 1).

FIG. 8 shows the bifurcated drug infusion catheter 100 in the expanded configuration. When expanded, the infusion tubes 104, 106 can bow away from the central catheter tube 102 in order to provide drug infusion nearer to the inner wall 34 (FIG. 1) of the abdominal aorta 10 (FIG. 1) and maintain positioning within aorta 10. When there is no longer a need for drug infusion, the infusion tubes 104, 106, are retracted against the central catheter tube 102. In the retracted configuration, shown in FIG. 9, the bifurcated drug infusion catheter 100 can be inserted into the abdominal aorta 10, e.g., from the right iliac artery 22 or the left iliac artery 24. Additionally, following drug infusion, the infusion tubes 104, 106 can retract and aid in removal of the bifurcated drug infusion catheter 100 from the abdominal aorta 10 (FIG. 1).

It is to be understood that one or more additional struts or tubes (not shown) may be added to catheter 100 to position or stabilize the infusion tubes 104, 106 near the renal arteries. It is further understood that the additional struts may be made of different materials than the infusion tubes 104, 106.

FIG. 10 through FIG. 14 show various modes according to a further embodiment of a bifurcated fluid infusion catheter, generally configured as an infusion ring, and designated 120. FIGS. 10 through 14 show that the bifurcated drug infusion catheter 120 includes a central catheter tube 122 that defines a proximal end (not shown) and a distal end 124. An infusion ring 126 is attached to the distal end 124 of the central catheter tube 122. More specifically, the infusion ring 126 includes a first end 128 and a second end 130 that are attached to the distal end 124 of the central catheter tube 122. During infusion, a drug solution can flow from the central catheter tube 122 into the infusion ring 126 via the first end 128 and second end 130 thereof.

Still referring to FIG. 10 through FIG. 14, the infusion ring 126 is preferably formed with a first infusion port 132 and a second infusion port 134. In a beneficial embodiment, the infusion ports 132, 134 are located along the infusion ring 126 at approximately one-hundred and eighty degrees (180°) from each other. FIG. 10 through FIG. 14 further show that the infusion ring 126 includes plural radio-opaque marker bands 136. As shown in FIG. 11, during infusion, a drug solution 138 can flow from the infusion ports 132, 134, e.g., at or above the renal arteries 12, 14.

It can be appreciated that the infusion ring 126 can be made of a material having a radial strength sufficient enough to maintain the infusion ring 126 against the inner wall 34 of the abdominal aorta 10, as shown in FIG. 12. However, the infusion ring 126 is sufficiently flexible to allow it to become slightly squashed, i.e., elliptical, during insertion. Further, it can be appreciated that the infusion ring 126 can be radio-opaque in order to aid in locating and positioning the infusion ring 126 within the abdominal aorta 10. The marker bands 138 can aid in positioning the infusion ports 132, 134.

Figure 13:
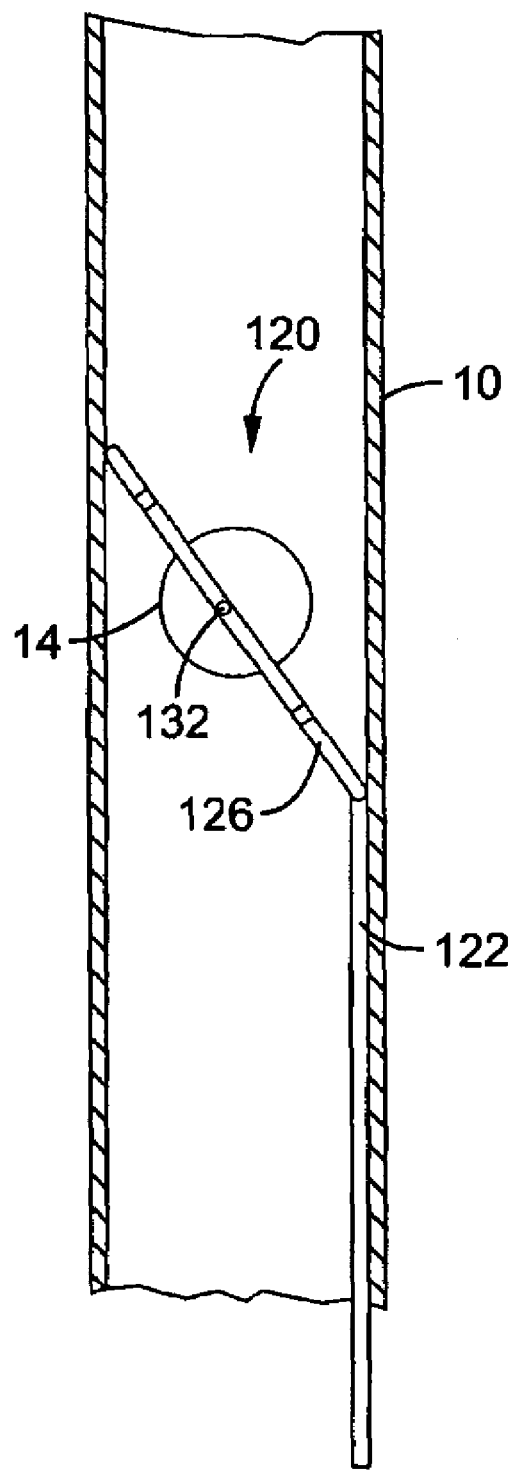
FIG. 13 is a left side plan view of the bifurcated drug infusion catheter shown in FIGS. 10-12, and shows one mode of use disposed within an abdominal aorta adjacent to the renal arteries.

As shown in FIG. 12 and FIG. 13, the location of the infusion ring 126 can be exactly at the renal arteries 12, 14, i.e., with the infusion ports 132, 134 aligned with the renal arteries 12, 14, in order to maximize drug infusion into the renal arteries 12, 14.

One benefit of the infuser ring configuration is it is easy to position, visualize, advance and retract in the aorta. Another benefit is it is low profile. This allows guide catheters and guide wires to pass and reduces thrombus formation due to flow disruption. The low profile low bulk of the infusion ring allows insertion using smaller diameter sheaths. In one beneficial embodiment, the infusion ring is made of a memory shape material such as Nitinol tubing, vertically oriented, and fed through an introducer sheath in a collapsed state to its position near the renal arteries. In another embodiment, the infusion ring is a flexible free form material and a pull wire is extended through the infusion ring to control expansion of the ring and does not require placement by an introducer sheath. This configuration also allows rotational positioning in a contracted state without the risk of vessel trauma. In a further embodiment, additional homodynamic aids (wings, spoilers, flow directors, etc.) can be coupled on the Nitinol loop in areas which cause limited flow disruption (i.e. simply against the aortas' posterior wall).

FIG. 13 shows a configuration where the bifurcated drug infusion catheter 120 is installed within the abdominal aorta 10 and the central catheter tube 122 rests against the back of the abdominal aorta 10 while the infusion ring 126 is at an angle with respect to the abdominal aorta 10. This configuration is beneficial to allow guide catheters and guide wires to pass through the infusion ring 126.

Figure 14:
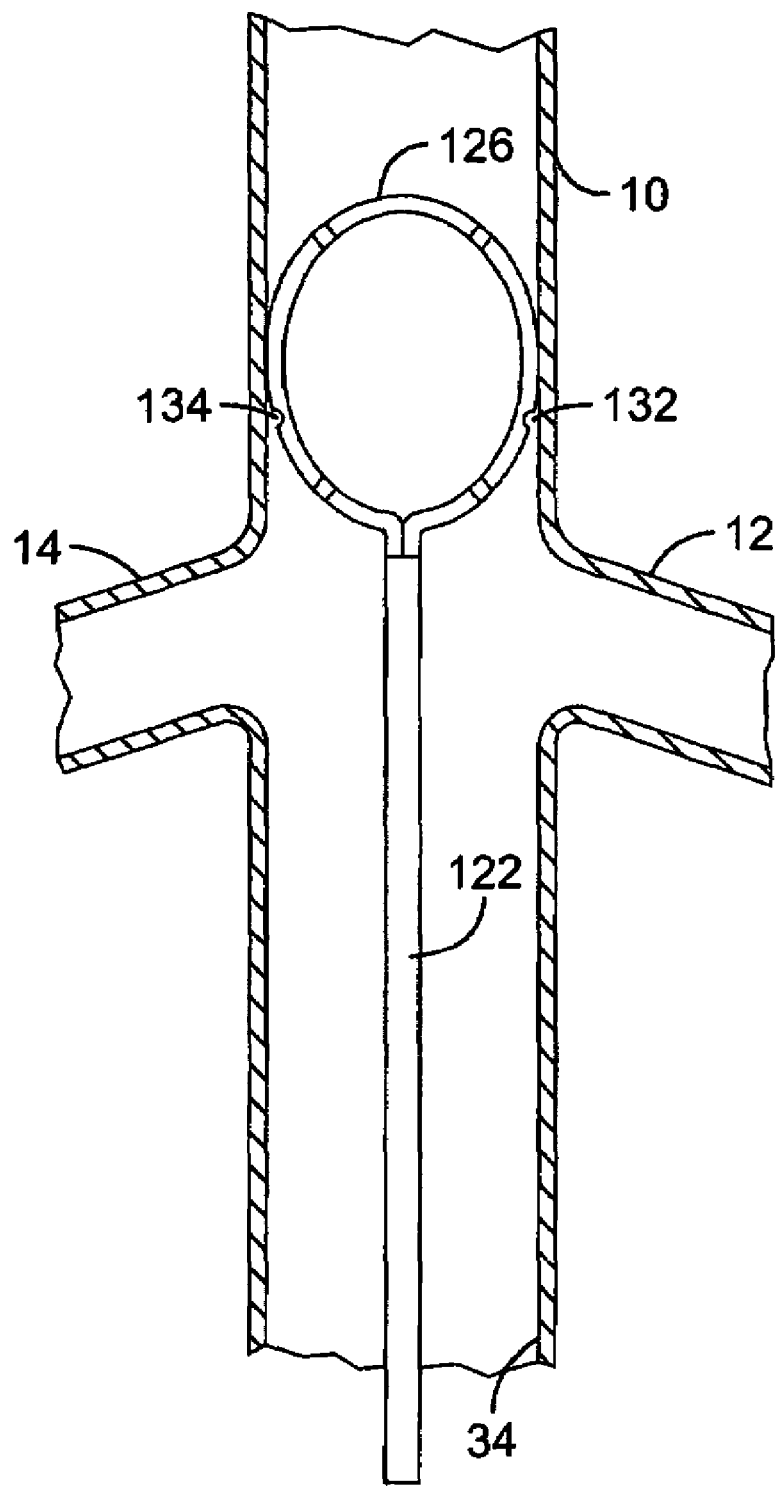
FIG. 14 is an anterior view of the bifurcated drug infusion catheter shown in FIGS. 10-12, and shows another mode of use disposed within an abdominal aorta immediately above the renal arteries.

On the other hand, as shown in FIG. 14, the infusion ring 126 can be placed above the renal arteries 12, 14 with the infusion ports 132, 134 slightly distanced from the renal arteries 12, 14. Due to the flow pattern discussed above in conjunction with FIG. 2, no vessel or side branch can disturb the flow stream above the renal arteries 12, 14. With drug infusion along the wall 34 of the abdominal aorta 10, other branches extending from the abdominal aorta 10 cannot disturb the flow streams into the renal arteries 12, 14.

Figure 15:
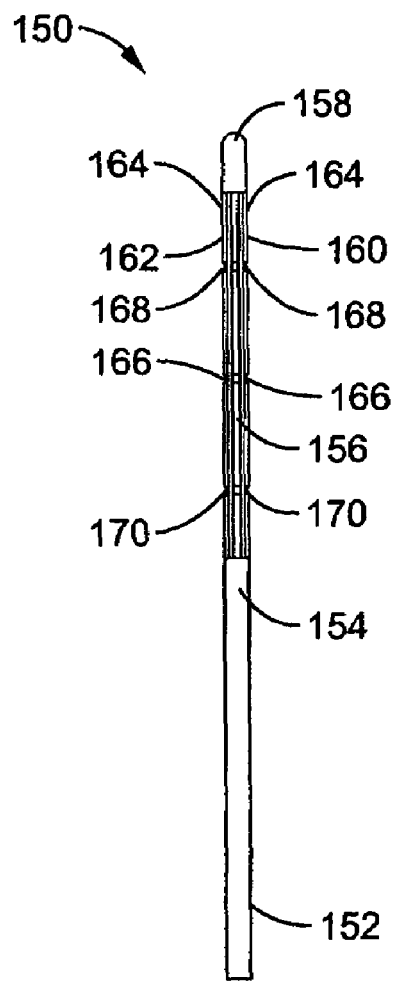
FIG. 15 is a plan view of a fluid infusion catheter with positioning struts according to a further embodiment, and shows the struts in a collapsed configuration.
Figure 16:
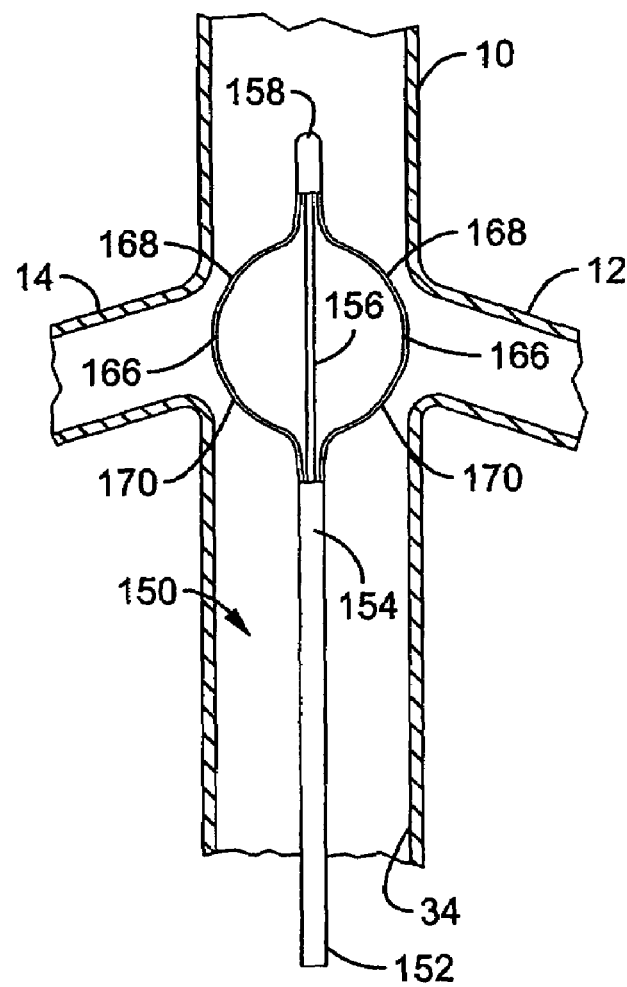
FIG. 16 is an anterior view of the fluid infusion catheter shown in FIG. 15, shown with the struts disposed within an abdominal aorta adjacent to the renal arteries in an expanded configuration.

Referring now to FIG. 15 and FIG. 16, a further embodiment is a drug infusion catheter with positioning struts for positioning the catheter within an abdominal aorta is shown and is generally designated 150. FIG. 15 and FIG. 16 shows that the drug infusion catheter 150 includes an outer tube 152 that defines a proximal end (not shown) and a distal end 154. A central support tube 156 extends from within the outer tube 152 beyond the distal end 154 thereof. A tip 158 is provided at the end of the central support tube 156.

FIG. 15 and FIG. 16 show that the drug infusion catheter 150 includes a first collapsible strut 160 and a second collapsible strut 162 slidably disposed within the outer tube 152. Each collapsible strut 162 includes a proximal end (not shown) and a distal end 164 and the distal end 164 of each collapsible strut 162 is attached to the tip 158. As intended by the present embodiment, when each collapsible strut 160, 162 is extended out of the outer tube 152, they bow outward relative to the central support tube 156—since the distal end 164 of the strut 160, 162 is affixed to the tip 158.

As shown, each collapsible strut 160, 162 includes an infusion port 166. Further, each collapsible strut 160, 162 includes a first marker band 168 above the infusion port 166 and a second marker band 170 below the infusion port 166. Preferably, each marker band is radio-opaque to assist in positioning the drug infusion catheter 150 within the abdominal aorta 10.

FIG. 15 shows the drug infusion catheter 150 in the collapsed configuration, i.e., with the collapsible struts 160, 162 that form positioning struts in the collapsed configuration. In the collapsed configuration, the drug infusion catheter 150 can be inserted into to the right or left iliac artery 22, 24 (FIG. 1) and fed into the abdominal artery 10 until it is in proper position near the renal arteries 12, 14. Once in position near the renal arteries 12, 14, the collapsible struts 160, 162 can be advanced forward relative to the outer tube 152 causing them to release from the central support tube 156. The collapsible struts 160, 162 can be advanced forward until they establish the expanded configuration shown in FIG. 16. In the expanded configuration, the infusion ports 166 are positioned immediately adjacent to the renal arteries 12, 14 and can release a drug solution directly into the renal arteries 12, 14. It can be appreciated that the drug infusion catheter 150 can be placed so that the drug solution is infused immediately above the renal arteries 12, 14 along the wall 34 of the abdominal aorta 10. After a specified dwell time within the abdominal aorta 10, the drug infusion catheter 150 can be returned to the collapsed configuration and withdrawn from the abdominal aorta 10.

Figure 17:
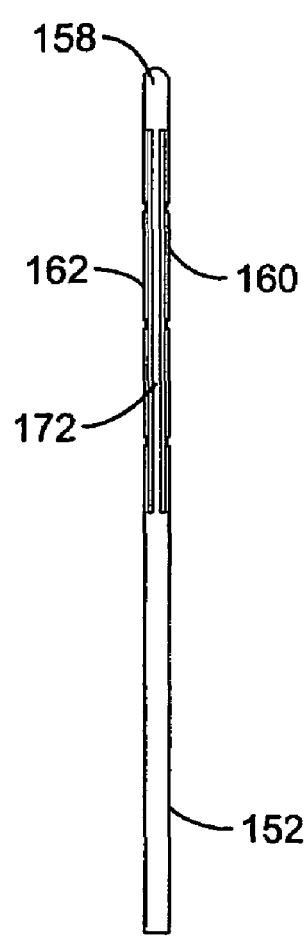
FIG. 17 is a plan view of another fluid infusion catheter with struts shown in a collapsed configuration.
Figure 18:
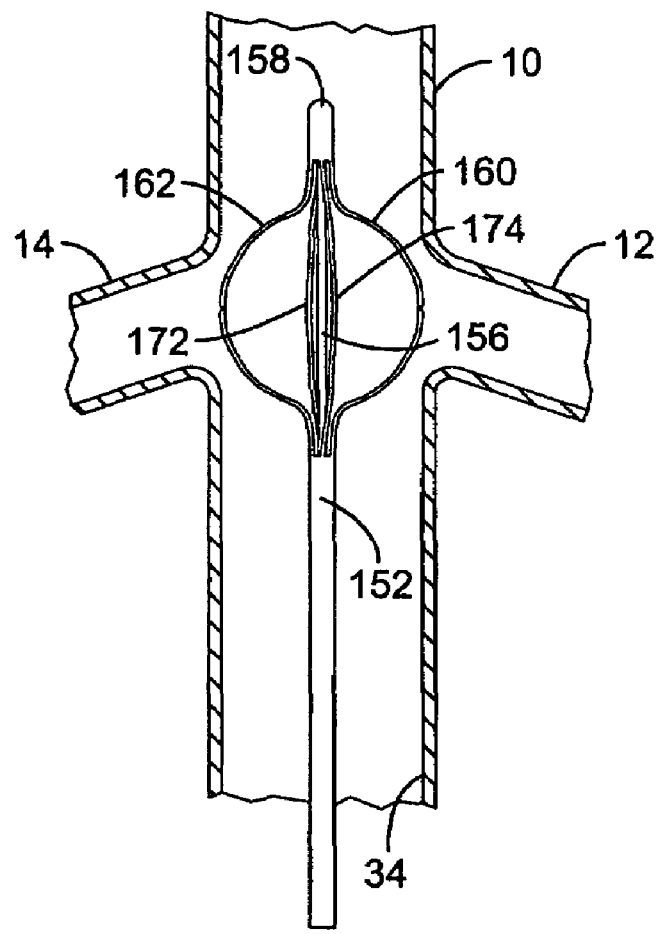
FIG. 18 is an anterior view of the fluid infusion catheter shown in FIG. 17, and shows the positioning struts disposed within an abdominal aorta adjacent to the renal arteries in an expanded configuration.

Referring briefly to FIG. 17 and FIG. 18, another embodiment of a drug infusion catheter with positioning struts is shown. FIG. 17 and FIG. 18 shows that the drug infusion catheter 150 can include a third collapsible strut 172 and a fourth collapsible strut 174. Accordingly, when expanded as described above, the drug infusion catheter 150 with the four collapsible struts 160, 162, 172, 174 resembles a cage.

FIG. 19 and FIG. 20 show another embodiment of a drug infusion catheter with positioning struts for positioning the catheter within an abdominal aorta, generally designated 200. As shown, the drug infusion catheter 200 includes an outer tube 202 having a proximal end (not shown) and a distal end 204. A first collapsible strut 206, a second collapsible strut 208, a third collapsible strut 210, and a fourth collapsible strut 212 are established by the outer tube 202 immediately adjacent to the distal end 204 of the outer tube 202. Moreover, a central support hypotube 214 is slidably disposed within the outer tube 202. A distal end (not shown) of the central support hypotube 214 is affixed within the distal end 204 of the outer tube 202. Accordingly, as intended by the present embodiment, when the central support hypotube 214 is retracted proximally in the outer tube 202, the struts 206, 208, 210, 212 expand and create a cage configuration that can secure the drug infusion catheter 200, e.g., within the abdominal aorta 10 near the renal arteries 12, 14.

FIG. 19 and FIG. 20 show that the first strut 206 and the second strut 208 are each formed with an infusion port 216. Additionally, a first marker band 218 is disposed above the infusion ports 216 along each strut. And, a second marker band 220 is disposed below the infusion ports 216 along each strut. During use, a drug solution can be released from the infusion ports 216 formed in the first and second struts 206, 208. It can be appreciated that the third and fourth struts 210, 212 can also establish infusion ports and can further include marker bands, as described above. It can also be appreciated that drug infusion catheter 200 may be practiced with only a first and a second struts 206, 208 to present a lower profile.

FIG. 19 shows the drug infusion catheter 200 in the collapsed configuration. In the collapsed configuration, the drug infusion catheter 200 can be inserted into to the right or left iliac artery 22, 24 (FIG. 1) and fed into the abdominal artery 10 until it is in proper position near the renal arteries 12, 14. Once in position near the renal arteries 12, 14, the central support hypotube 214 is retracted proximally in outer tube 202 causing the struts 206, 208, 210, 212 to release from the central support tube 202 and bow outward. The central support hypotube 214 can be retracted proximally, as described above, until the struts 206, 208, 210, 212 establish the expanded configuration shown in FIG. 20.

In the expanded configuration, the infusion ports 216 are positioned immediately adjacent to the renal arteries 12, 14 and can release a drug solution directly into the renal arteries 12, 14. It can be appreciated that the drug infusion catheter 200 can be placed so that the drug solution is infused immediately above the renal arteries 12, 14 along the wall 34 of the abdominal aorta 10. After a specified dwell time within the abdominal aorta 10, the drug infusion catheter 200 can be returned to the collapsed configuration and withdrawn from the abdominal aorta 10.

Figure 21:
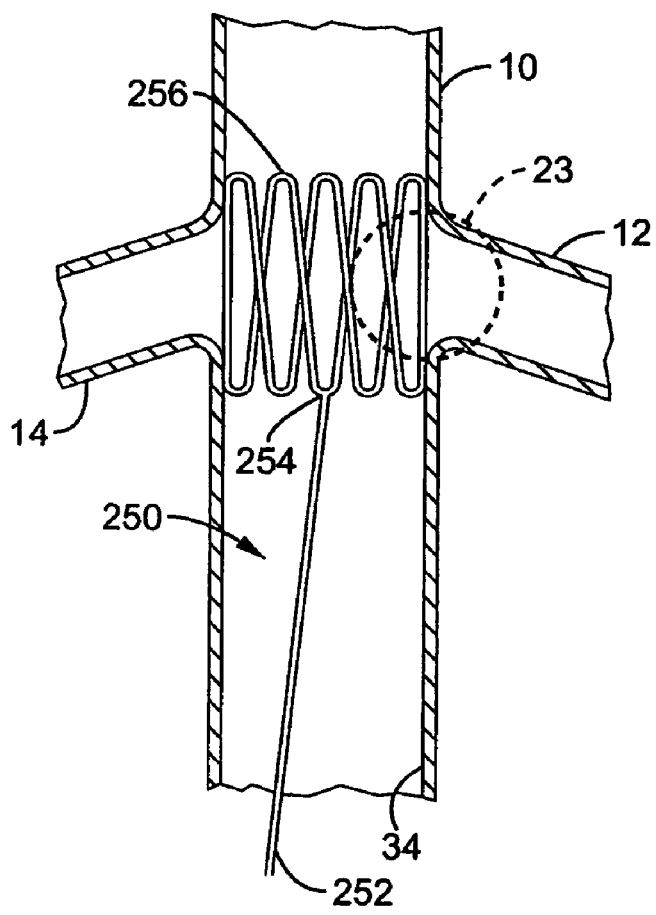
FIG. 21 is an anterior view of another fluid infusion catheter with an anchor disposed within an abdominal aorta adjacent to the renal arteries in an expanded configuration.

Referring to FIG. 21, another embodiment of a drug infusion catheter with an anchor for positioning the catheter within an abdominal aorta is shown and is generally designated 250, FIG. 21 shows the drug infusion catheter 250 installed within an abdominal aorta 10 in the vicinity of the renal arteries 12, 14. As shown in FIG. 21, the drug infusion catheter 250 includes a central catheter tube 252 having a proximal end (not shown) and a distal end 254. A hollow stent 256 is attached to the distal end 254 of the central catheter tube 252 and a drug solution can flow from the central catheter tube 252 into the hollow stent 256. In this aspect of the present embodiment, the hollow stent 256 is formed partially or entirely of hollow hypo tubing, though other variations of elastomeric tubing may be used.

Figure 22:
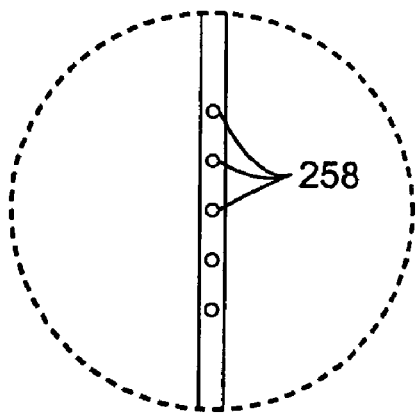
FIG. 22 is a detailed view of certain aspects of the fluid infusion catheter shown in FIG. 21.
Figure 23:
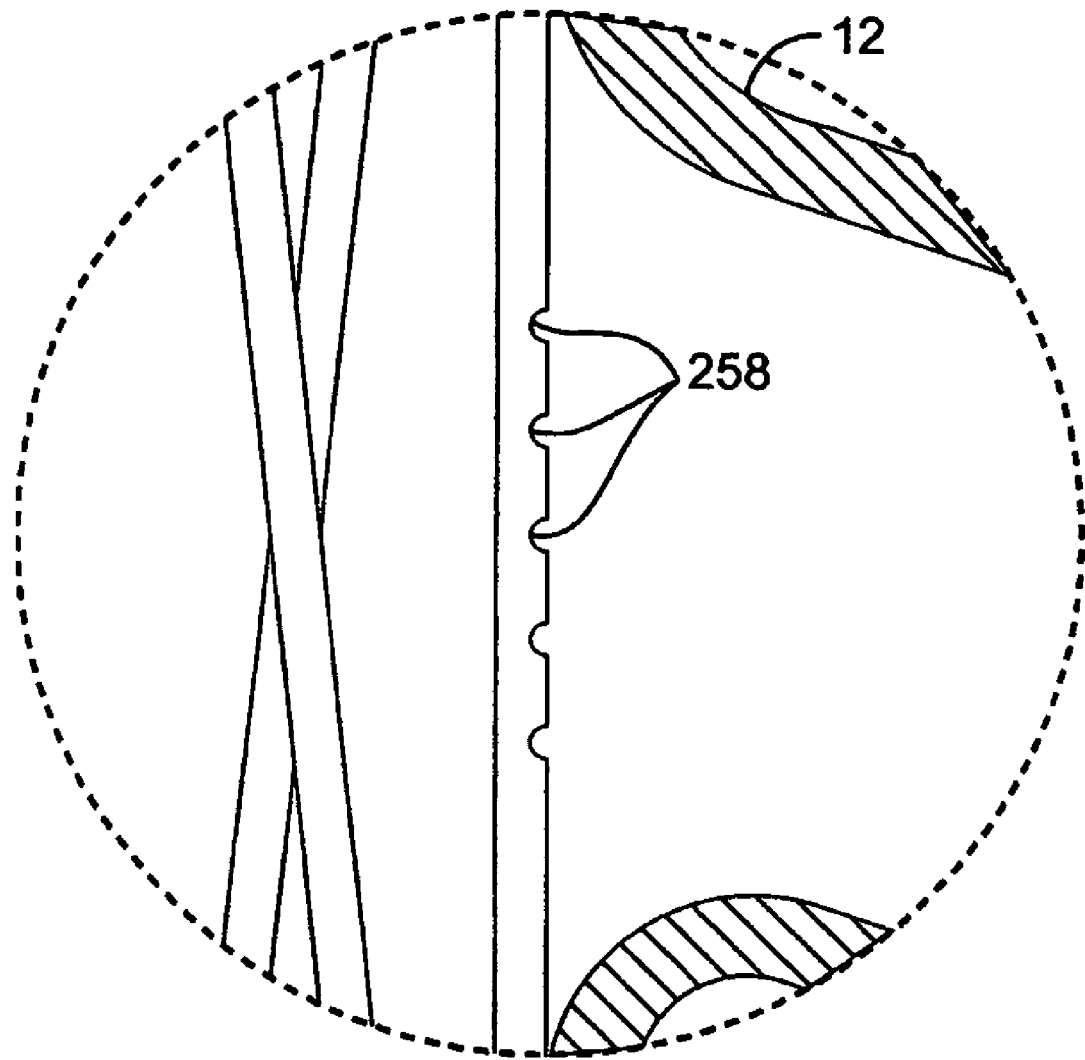
FIG. 23 is a detailed view of the fluid infusion catheter taken at circle 23 in FIG. 21.
Figure 24:
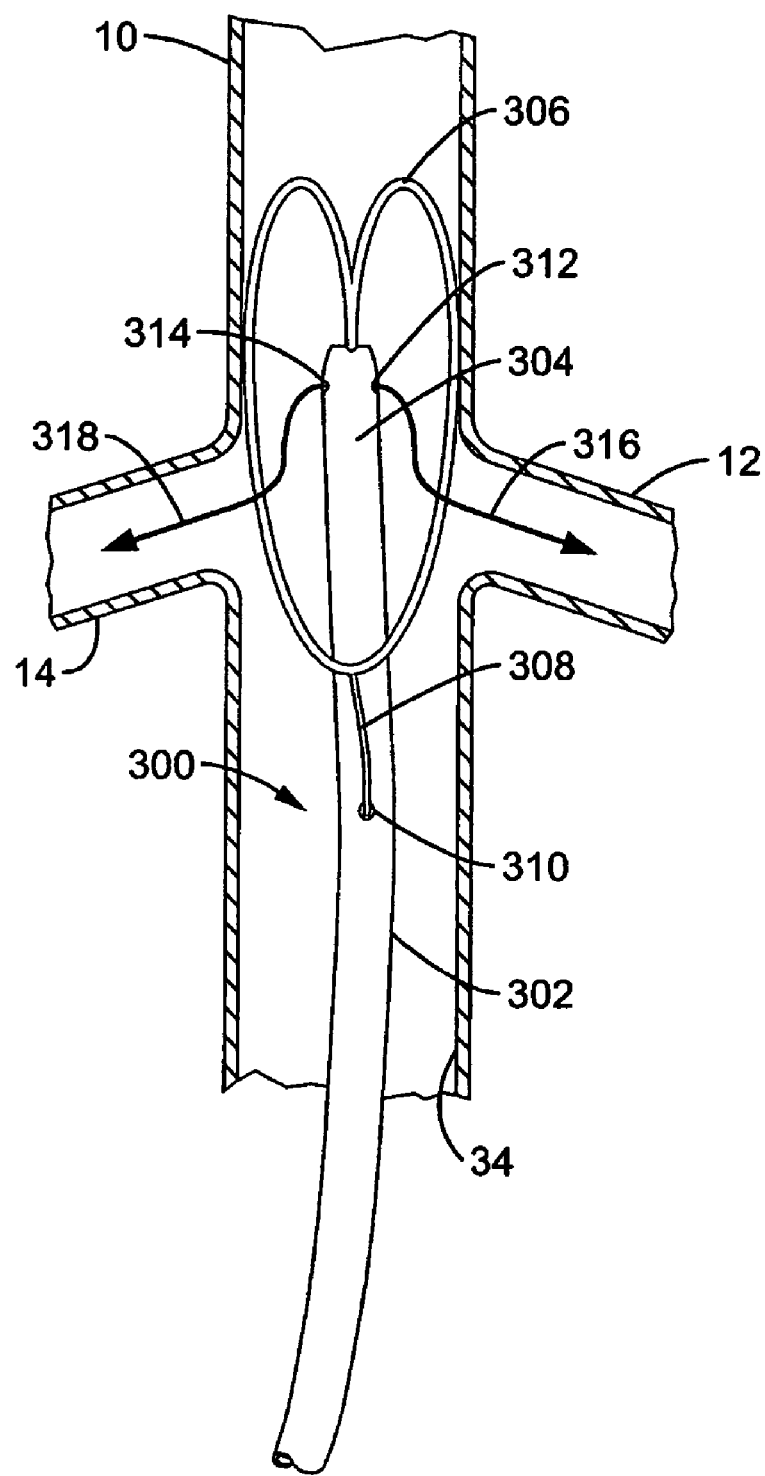
FIG. 24 is an anterior view of another fluid infusion catheter with a positioning loop disposed within an abdominal aorta immediately above the renal arteries in an extended configuration.
Figure 25:
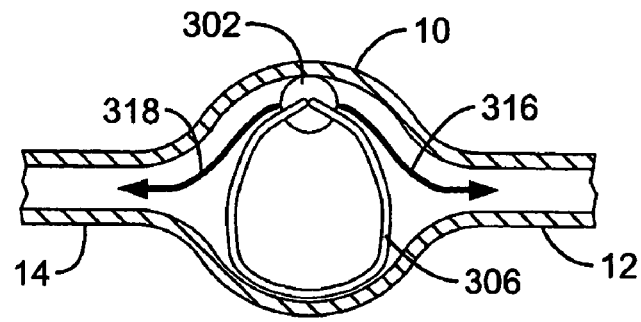
FIG. 25 is a top plan view of the fluid infusion catheter shown in FIG. 24, and shows the positioning loop is disposed within an abdominal aorta immediately above the renal arteries in an extended configuration.
Figure 26:
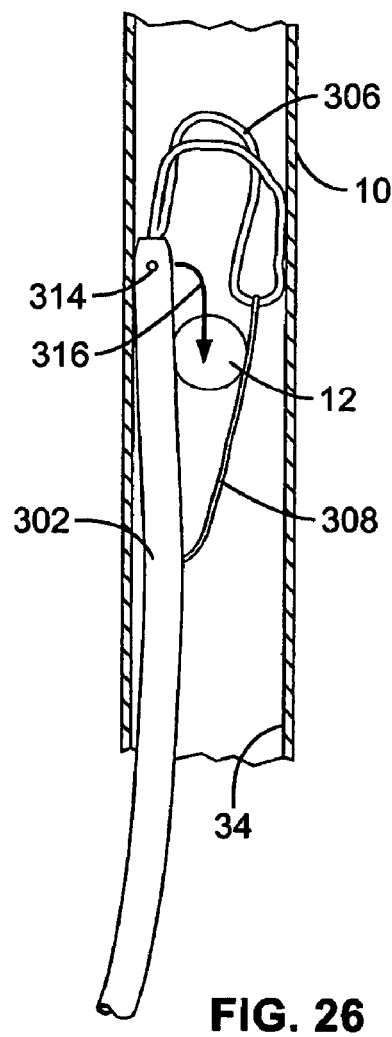
FIG. 26 is a side plan view of the fluid infusion catheter shown in FIGS. 24-25, and shows the positioning loop disposed within an abdominal aorta immediately above the renal arteries in an extended configuration.
Figure 27:
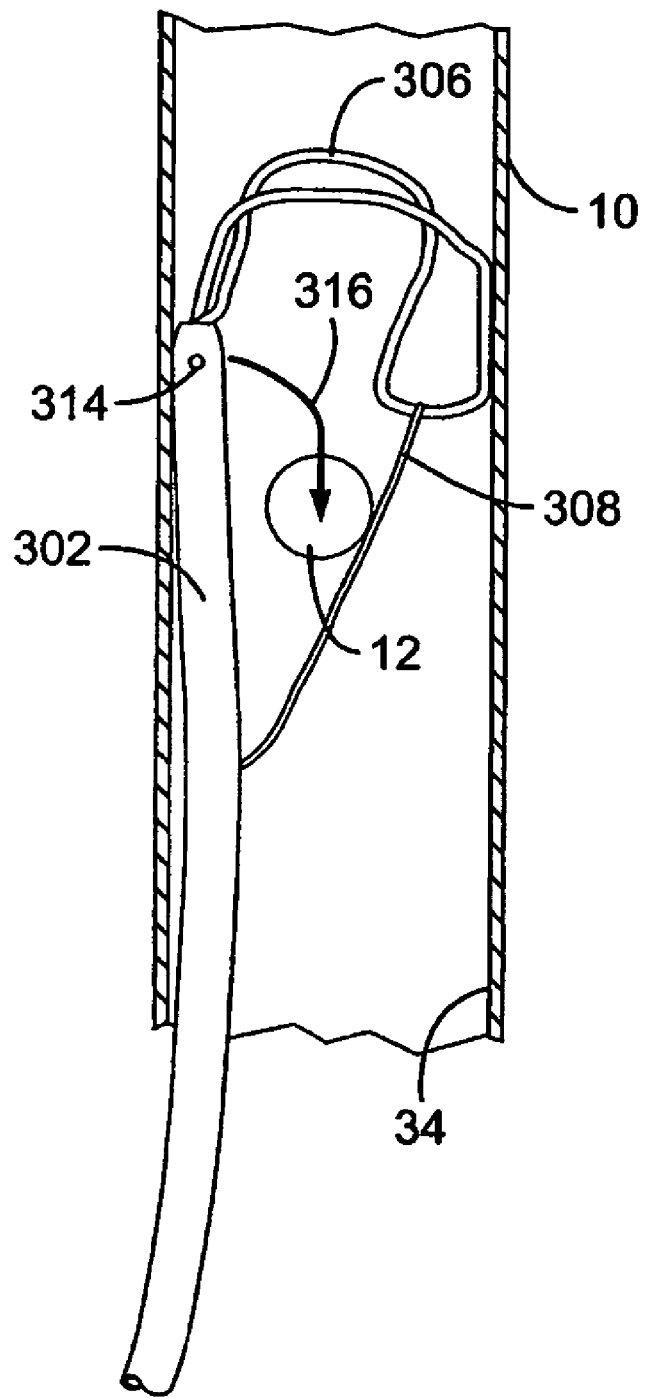
FIG. 27 is a second side plan view of the fluid infusion catheter shown in FIGS. 24-25, and shows the positioning loop disposed within an abdominal aorta immediately above the renal arteries in an extended configuration.

As shown in FIG. 22 and FIG. 23, the stent 256 can be punctured or otherwise formed with plural infusion ports 258 along the outer surface of the stent 256. The drug infusion catheter 250 can be positioned, and expanded, within the abdominal aorta 10, as shown in FIG. 21, such that the stent 256 is anchored in the vicinity of the renal arteries 12, 14. As such, a drug solution can be released from the hollow stent 256 via the infusion ports 258 directly into the renal arteries 12, 14. By expanding the stent 256 against the inner wall 34 of the abdominal aorta 10 in the area of the renal arteries 12, 14 all the infusion ports can be blocked (since they are established on the outside surface of the stent 256) except those that are directly over the renal ostia. Thus, when a drug solution is infused, its flow into the renal arteries 12, 14 is maximized.

It can be appreciated that the stent 256 can form an expandable open-mesh structure that can have an element, or a few elements, that cross the renal ostia without disrupting the blood flow to the renal arteries 12, 14. It is to be understood that the ability to deploy and recapture the stent 256 can be accomplished using a number of methods apparent to those of ordinary skill in the art based on review of this disclosure, e.g., by suitably modifying the methods typically employed for deploying and recapturing temporary vena cava filters or retractable stents.

Referring now to FIG. 24 through FIG. 28, another embodiment of a drug infusion catheter with positioning loops for positioning the catheter within an abdominal aorta is shown and is generally designated 300. FIG. 24 through FIG. 28 show that the drug infusion catheter 300 includes a central catheter tube 302 that defines a proximal end (not shown) and a distal end 304. As shown, a generally vertically oriented positioning loop 306 extends from the distal end 304 of the central catheter tube 302. Preferably, the positioning loop 306 is made from a memory metal, e.g., nickel-titanium (NiTi). It is to be understood that the positioning loop 306 can be held in a pre-determined position via shape setting or it can be in a free-form shape and held in a final diameter via the inner wall 34 of the abdominal aorta 10. As specifically shown in FIG. 26 and FIG. 27, the positioning loop 306 can sufficiently hold the drug infusion catheter 300 in place regardless of the diameter of the abdominal aorta 10 e.g. as shown in the smaller and larger diameter aortas of FIG. 26 and FIG. 27, respectively.

Figure 28:
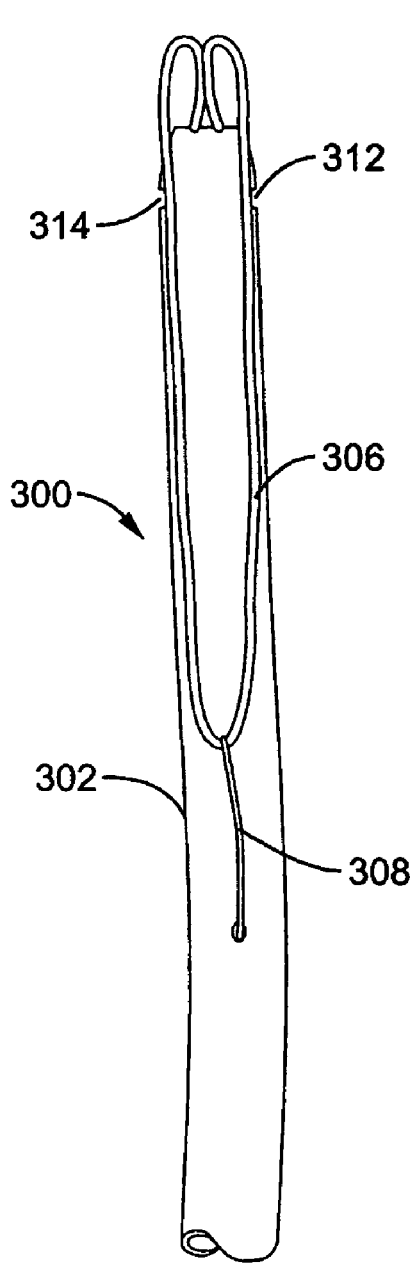
FIG. 28 is an anterior view of another fluid infusion catheter with an adjustable positioning loop in a retracted configuration.

As shown in FIG. 24 through 28, the drug infusion catheter 300 can include a pull wire 308 that extends from a port 310 formed in the central catheter tube 302. The pull wire 308 is attached to the positioning loop 306 and can be used to control the expansion and contraction of the positioning loop 306 without the need for an external sheath. FIG. 28 specifically shows the positioning loop 306 in a fully retracted configuration that can be used when inserting or withdrawing the drug infusion catheter 300.

FIG. 24 through 28 further show that the central catheter tube 302 is formed with a first infusion port 312 and a second infusion port 314. A drug solution can exit the central catheter tube 302 and flow into the renal arteries 12, 14 as indicated by arrow 316 and 318.

It can be appreciated that the drug infusion catheter 300 shown in FIG. 24 through 28 can allow rotational position adjustment and vertical position adjustment without the risk of trauma to the abdominal aorta 10. Further, the positioning loop 306 can be retracted numerous ways to allow atraumatic rotation. And, since there are not any protruding or traumatic edges to catch aortic tissue on, the drug infusion catheter 300 can be moved up and down without retracting the positioning loop 306. In another beneficial embodiment, positioning loop 306 is free form without pull wire 310. It can be appreciated that positioning loop 306 can be made of a shape-memory alloy, such as Nitinol™, and advanced through the distal end 304 of catheter 300 for positioning and retracted for insertion and removal.

The present embodiment recognizes that experimental observations have shown that a drug solution can flow into the renal arteries 12, 14 naturally, provided the drug infusion is undertaken above the renal arteries 12, 14 and above or closely adjacent to the posterior aspect of the inner wall 34 of the abdominal aorta 10. As shown in FIG. 25 through FIG. 28, the positioning loop 306 can easily position the central catheter tube 302 against the posterior of the inner wall 34 of the abdominal aorta 10 and does not require a flow diverter, e.g., a balloon or membrane, to maximize drug infusion to the renal arteries 12, 14. As such, the possibility of thrombus formation due to the disruption of blood flow is minimized.

It can be appreciated that the drug infusion catheter 300 can easily allow various guide catheters and guide wires to pass therethrough and that passage can have minimal effect on the tactile feedback or other performance aspects of the adjunctive catheters that are typically used in a percutaneous coronary intervention (PCI).

Figure 29:
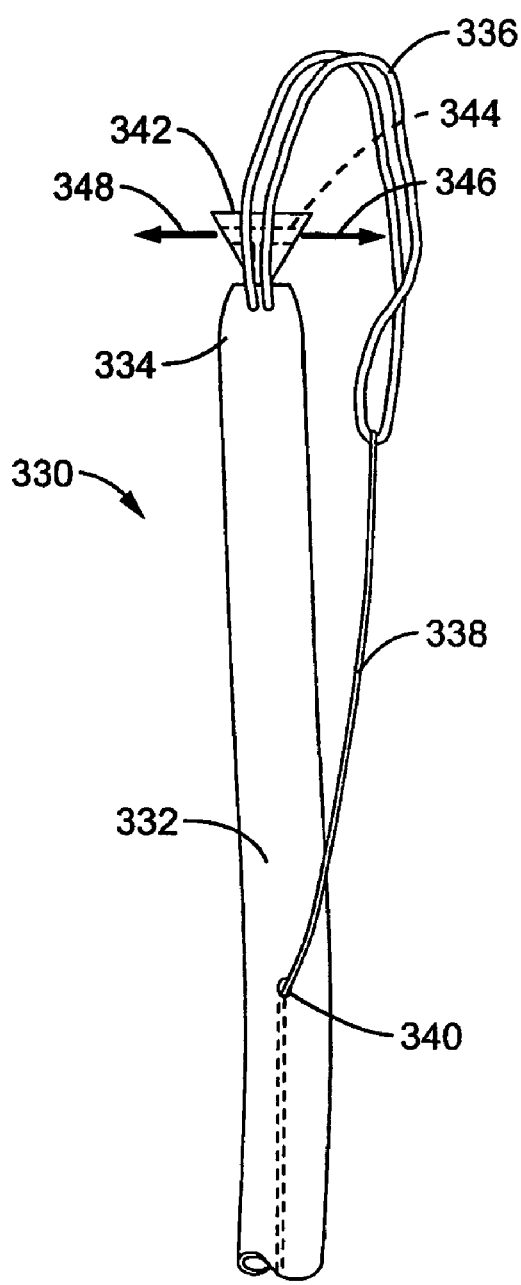
FIG. 29 is an anterior view of another fluid infusion catheter with a positioning loop in a partially extended configuration.

FIG. 29 shows another embodiment of a drug infusion catheter with a positioning loop for positioning the catheter within an abdominal aorta, generally designated 330. As shown, the drug infusion catheter 330 includes a central catheter tube 332 having a proximal end (not shown) and a distal end 334. As shown, a positioning loop 336 extends from the distal end 334 of the central catheter tube 332. Further, the drug infusion catheter 330 can include a pull wire 338 that extends from a port 340 formed in the central catheter tube 332. The pull wire 338 is attached to the positioning loop 306 and can be used to retract the positioning loop 336 during insertion or withdrawal of the drug infusion catheter 330.

As shown in FIG. 29, a flow director 342 is affixed to the distal end 334 of the central catheter tube 332. The flow director 342 is formed with a bifurcated (e.g. a T-shaped) infusion passage 344 that directs the flow of a drug solution from an infusion port (not shown) formed in the distal end 334 of the central catheter tube 332 in two opposing directions—as indicated by arrow 346 and arrow 348.

Figures 30, 31:
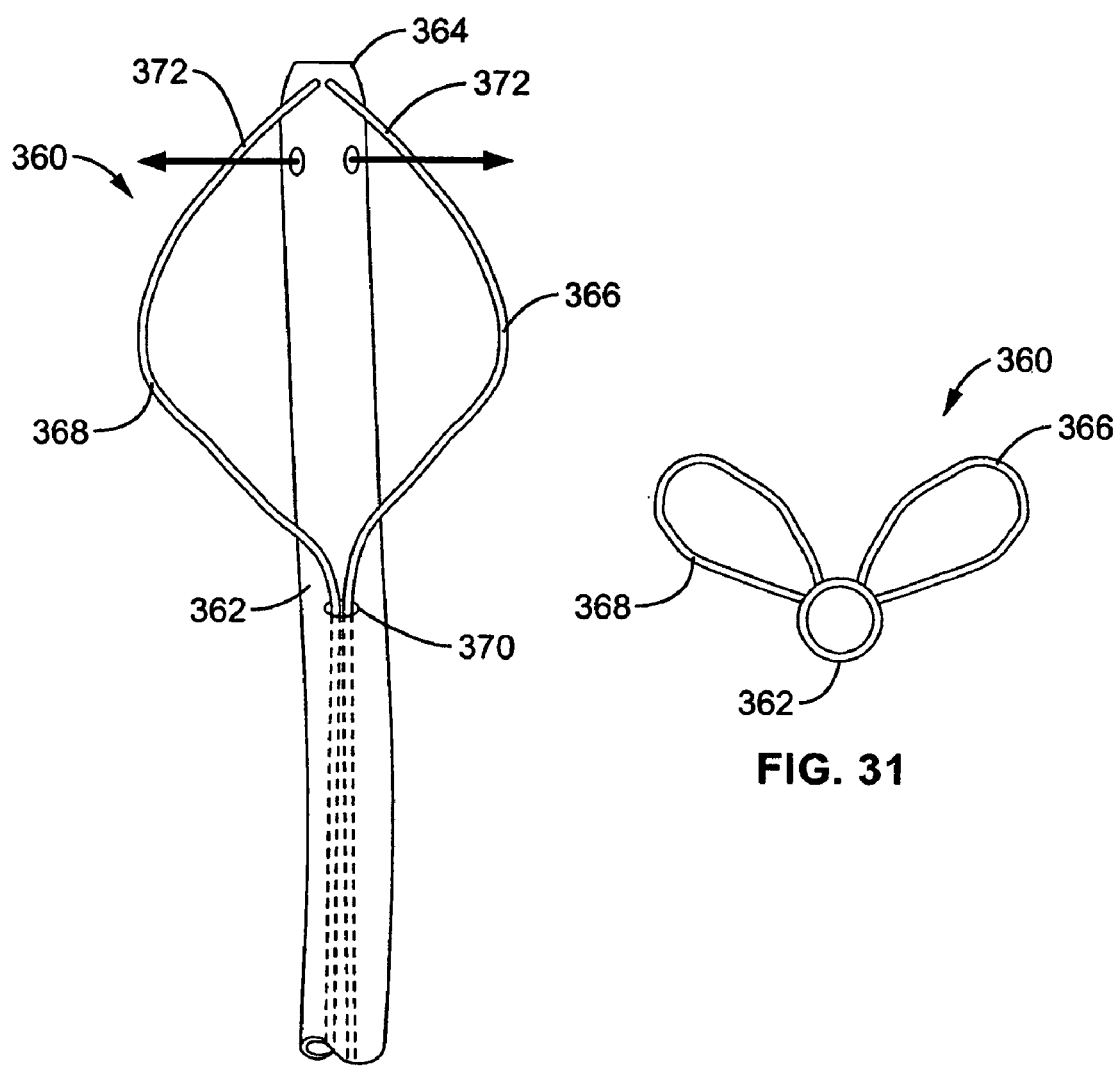
FIG. 30 is a anterior view of another fluid infusion catheter with positioning loops in an extended configuration.
FIG. 31 is a top plan view of the fluid infusion catheter shown in FIG. 30, and shows the positioning loops in an extended configuration.

Referring to FIG. 30 and FIG. 31, another embodiment of a drug infusion catheter with positioning loops for positioning the catheter within an abdominal aorta is shown and is generally designated 360. As shown, the drug infusion catheter 360 includes a central catheter tube 362 that defines a proximal end (not shown) and a distal end 364. As shown, a first positioning wire 366 and a second positioning wire 368 extend from a port 370 formed in the central catheter tube 362. Each positioning wire 366, 368 defines a proximal end (not shown) and a distal end 372. The distal end 372 of each positioning wire 366, 368 is attached to the distal end 364 of the central catheter tube 362. It is to be understood that the positioning wires 366, 368 extend through the entire length of the central catheter tube 370 and can be used to establish an adjustable positioning loop. It can be appreciated that the adjustable positioning loop can be adjusted by extending or retracting the positioning wires 366, 368 through the port 370 in the central catheter tube 363.

Figures 32, 33:
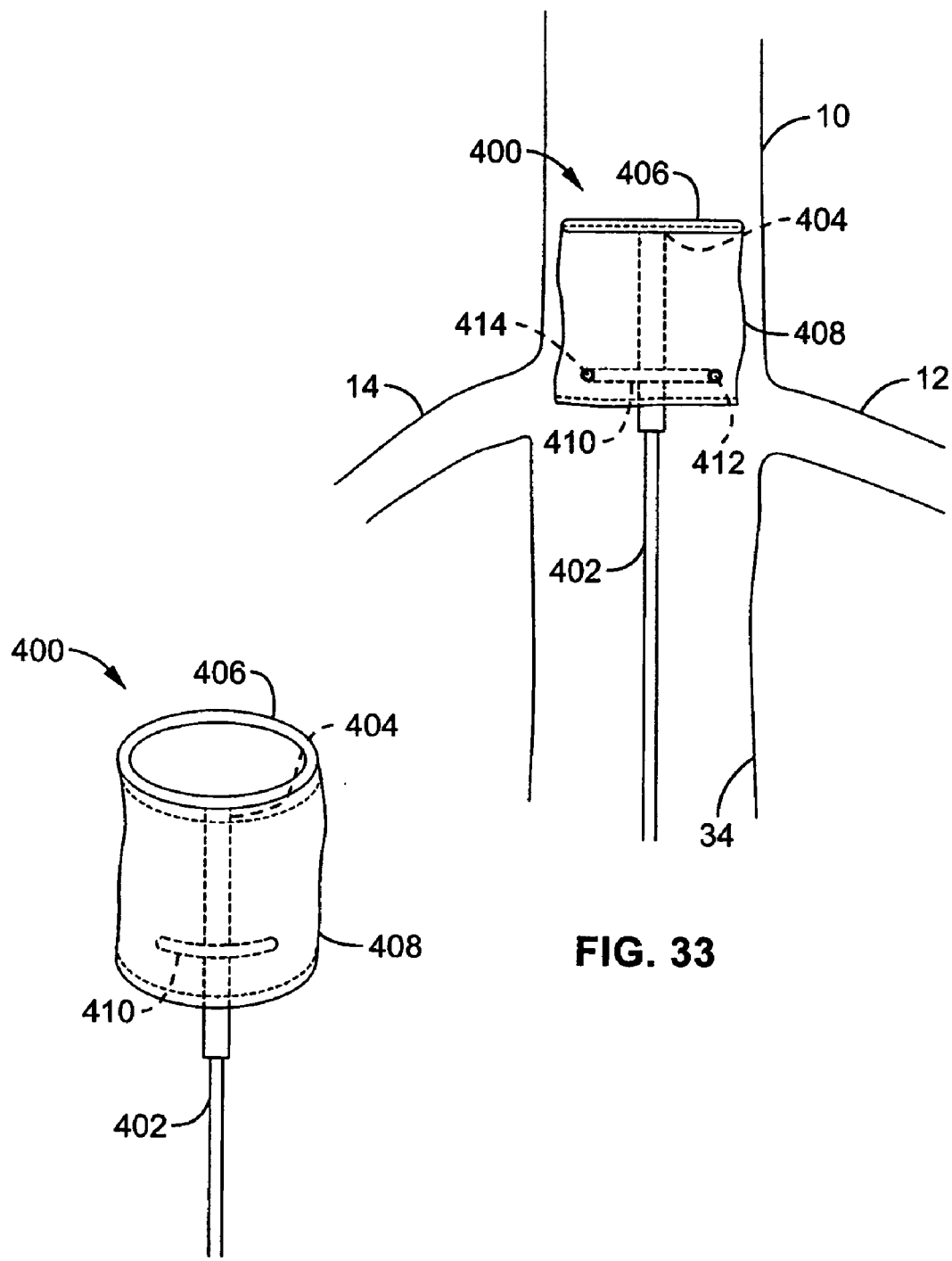
FIG. 32 is a perspective view of another embodiment according to the invention with a fluid infusion catheter cooperating with a flow diverter.
FIG. 33 is an anterior view of the fluid infusion catheter shown in FIG. 32, and shows the flow diverter disposed within an abdominal aorta adjacent to the renal arteries.

Referring now to FIG. 32 and FIG. 33, one embodiment of a drug infusion catheter with a renal flow isolator is shown and is generally designated 400. As shown, the drug infusion catheter 400 includes a central catheter tube 402 that defines a proximal end (not shown) and a distal end 404. A ring 406 is attached to the distal end 404 of the central catheter tube 402. Moreover, a generally cylindrical curtain 408 extends from the ring 406. Preferably, in this aspect of the present invention, the curtain 408 is made from expanded polytetrafluoroethylene (ePTFE) or any material with similar characteristics well known in the art. In one beneficial embodiment, the overall length of renal flow isolator 400 is about 1.5 cm.

FIG. 32 and FIG. 33 further show an infusion tube 410 that extends bi-directionally from the central catheter tube 402. A first infusion port 412 and a second infusion port 414 are established on the outside of curtain 408 by the infusion tube 410. In the exemplary, non-limiting embodiment shown in FIG. 32 and FIG. 33, the single ring 406 allows for sizing to the abdominal aorta 10 to maintain the infusion ports 412, 414 along the inner wall 34 of the abdominal aorta 10. It can be appreciated that the configuration of the drug infusion catheter 400 shown in FIG. 32 and FIG. 33 reduces the amount of stagnant blood around the drug infusion catheter 400 and thereby, minimizes the blood clotting thereon. This configuration also puts the drug along the aortic wall. In one embodiment, central catheter tube 402 has an offset that is a slight S shape (not shown) and positions renal flow diverter 400 off the aorta wall.

Figures 34, 35:
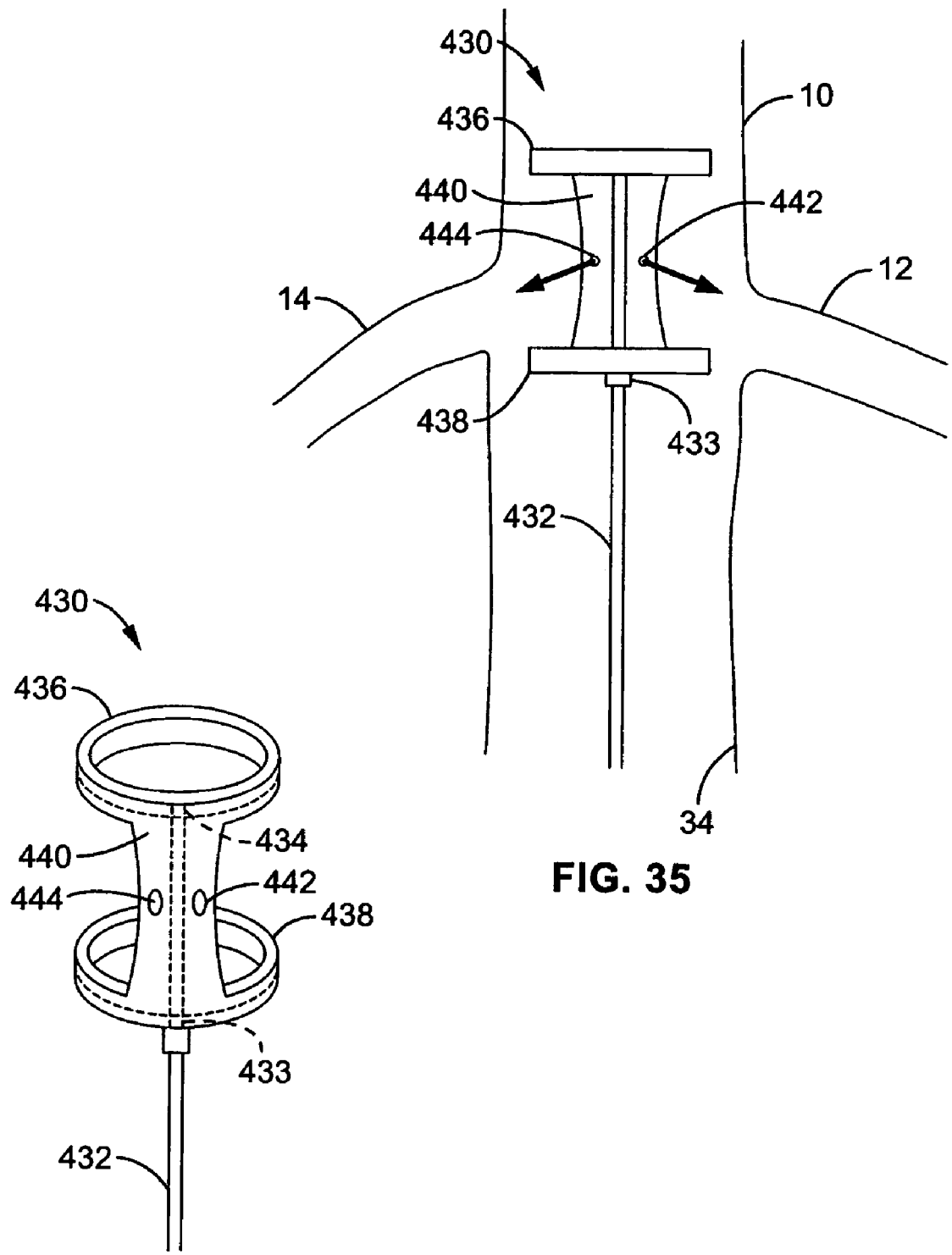
FIG. 34 is a perspective view of another drug infusion catheter with a flow diverter according to a further embodiment.
FIG. 35 is an anterior view of the fluid infusion catheter shown in FIG. 34, and shows the flow diverter disposed within an abdominal aorta adjacent to the renal arteries.

FIG. 34 and FIG. 35 show a further embodiment of a drug infusion catheter with a flow isolator, generally designated 430. As shown, the drug infusion catheter 430 includes a central catheter tube 432 with a mid distal position 433 and a distal end 434. An upper ring 436 is attached to the distal end 434 of the central catheter tube 432. Moreover, a lower ring 438 is attached to the catheter tube 432 at mid distal position 433 and at a distance slightly spaced from the upper ring 436. FIG. 34 and FIG. 35 further show catheter tube 432 connecting the upper ring 436 to the lower ring 438. In this aspect of the present invention, the catheter tube 432 between mid distal position 433 and distal end 434 is covered with a layer of fabric 440, such as ePTFE, extending from upper ring 436 to lower ring 438. It can be appreciated that the orientation of fabric 440 reduces the amount of stagnant blood collecting around the drug infusion catheter 430 and thereby, minimizes the blood clotting thereon. In one beneficial embodiment, the overall length of drug infusion catheter is about 2 cm.

As shown in FIG. 34 and FIG. 35, a first infusion port 442 and a second infusion port 444 are established in a mid section of fabric 440 of the drug infusion catheter 430. It is to be understood that the upper ring 436 and the lower ring 438 ensure that the infusion ports 442, 444 are placed along side of the inner wall 34 of the abdominal aorta 10. The preferred position of the drug infusion catheter 430 within the abdominal aorta 10 is such that the infusion ports 442, 444 are closest to the posterior of the abdominal aorta 10. Moreover, the rings 436 and 438 do not significantly alter blood flow through the abdominal aorta 10 and since they are open, a guiding catheter (not shown), or any other working catheter, can be advanced through the drug infusion catheter 430. In one embodiment, central catheter tube 432 has an offset that is a slight S shape (not shown) and positions drug infusion catheter 430 off the aorta wall.

Figure 36:
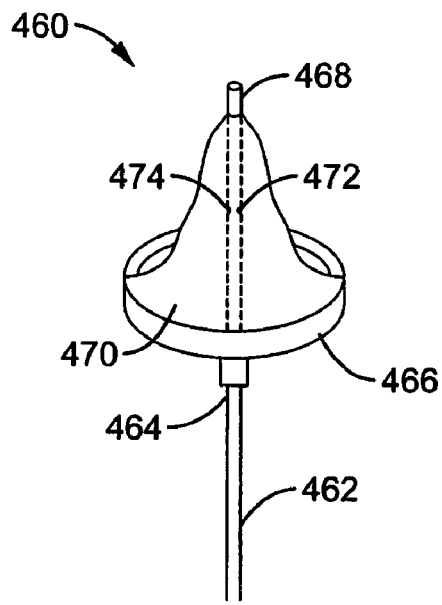
FIG. 36 is a perspective view of another fluid infusion catheter with a flow diverter according to still a further embodiment.
Figure 37:
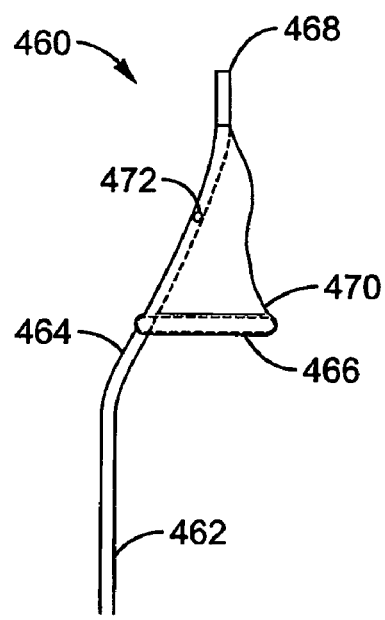
FIG. 37 is a side plan view of another embodiment of the fluid infusion catheter with flow diverter shown in FIG. 36.
Figure 38:
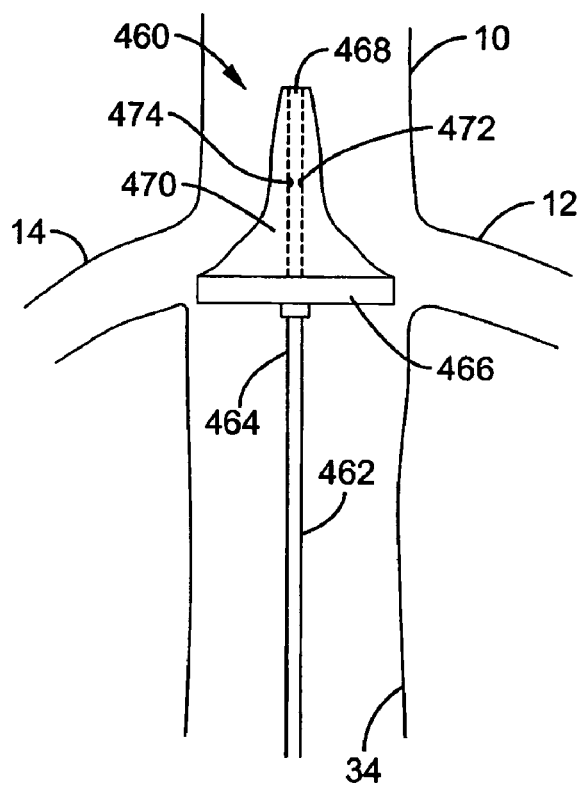
FIG. 38 is an anterior view of the fluid infusion catheter shown in FIGS. 36-37, and shows the flow diverter disposed within an abdominal aorta adjacent to the renal arteries.

Referring to FIG. 36 through FIG. 38, another embodiment of a drug infusion catheter is shown and is generally designated 460. As shown, the drug infusion catheter 460 includes a central catheter tube 462 that defines a proximal end (not shown) and a mid distal position 464. A ring 466 is attached near the mid distal position 464 of the catheter tube 462.

FIG. 36 through FIG. 38 further show central catheter tube 462 with an offset near mid distal position 464 and a sail 470 attached to the distal end 468 that extends partially around the perimeter of the ring 466. It can be appreciated that the sail 470 forms a semi-conical shape between the mast 468 and the ring 466. In this aspect, the sail 470 is made from ePTFE, though other suitable materials may be used or applied. It can be appreciated that the semi-conical shape of the sail 470 and the material from which it is constructed reduces the amount of stagnate blood around the drug infusion catheter 460 and as such, the chance of blood clots forming around the drug infusion catheter 460 is minimized. FIG. 36 and FIG. 38 show a first infusion port 472 and a second infusion port 474 established along the catheter tube 462 between distal end 468 and ring 466.

As intended by the present embodiment, the ring 466 maintains the position of the drug infusion catheter 460 against the inner wall 34 of the abdominal aorta 10. Also, the sail 470 is designed to divert blood flow, and thus, the flow of a drug solution trickling from the infusion ports 472, 474, into the renal arteries 12, 14. The preferred position of the drug infusion catheter 460 within the abdominal aorta 10 is such that the infusion ports 472, 474 are closest to the posterior of the abdominal aorta 10.

Figure 39:
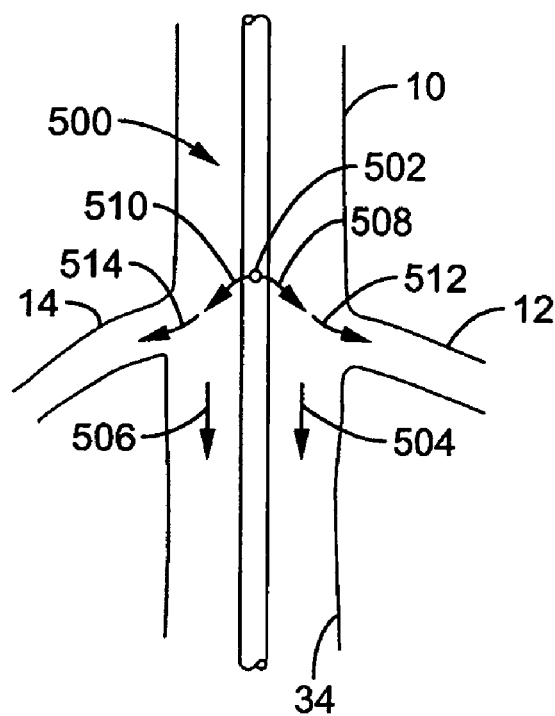
FIG. 39 is an anterior view of a fluid infusion guide catheter disposed within an abdominal aorta adjacent to the renal arteries.

FIG. 39 shows one embodiment a drug infusion guide catheter, designated 500, that can be placed within an abdominal aorta 10 in the general vicinity just above the renal arteries 12, 14. As shown, the drug infusion guide catheter 500 includes an infusion port 502 formed in the outer wall of the drug infusion guide catheter 500. It can be appreciated that a drug solution can be released from the drug infusion guide catheter 500 via the infusion port 502. The renal blood flow (see FIG. 2) to each renal artery 12, 14 is about 15 percent of total aortic blood flow for a total of about 30 percent. With no change in blood flow, about 30 percent of drug solution released from infusion port 502 will reach renal arteries 12,14.

It is to be understood that it is most advantageous to release the drug solution from the drug infusion guide catheter 500 during systole, as indicated by arrow 504 and arrow 506. As shown in FIG. 39, during systole, the drug solution can flow in a generally downward direction from the infusion port 502, as indicated by arrow 508 and arrow 510, and into the right renal artery 12 and the left renal artery 14, as indicated by arrow 512 and arrow 514. It is to be further understood that the drug infusion guide catheter 500 is at least formed with two lumens therein, i.e., a first relatively larger lumen for the exchange of devices and a second relatively smaller lumen for drug infusion. Accordingly, as intended by the present embodiment, the requirement for a secondary device, in addition to the drug infusion guide catheter 500, to infuse drugs and medication to the renal arteries 12, 14 during a PCI is obviated.

Figure 40:
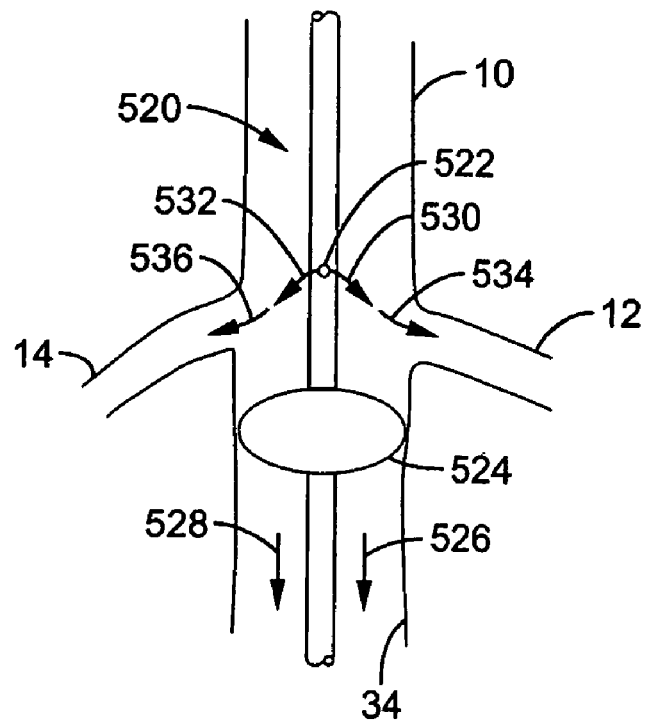
FIG. 40 is an anterior view of another fluid infusion guide catheter disposed within an abdominal aorta adjacent to the renal arteries.

FIG. 40 shows another embodiment of a drug infusion guide catheter, generally designated 520. As shown, the drug infusion guide catheter 520 can be inserted into the abdominal aorta 10, e.g., via the left or right iliac artery 22, 24 (FIG.

1), until it is in the vicinity of the renal arteries 12, 14. FIG. 40 shows that the drug infusion guide catheter 520 includes an infusion port 522 that is formed in the outer wall of the drug infusion guide catheter 520. It can be appreciated that a drug solution can be released from the drug infusion guide catheter 520 via the infusion port 522. As shown in FIG. 40, the drug infusion guide catheter 520 further includes a balloon 524 that can be inflated to divert blood flow into the renal arteries 12, 14.

In this aspect of the present invention, the balloon 524 can be made from silicon, nylon, PEBAX, polyurethane, or any other similar compliant or semi-compliant material well known in the art. Moreover, the balloon 524 can be inflated such that it engages the inner wall 34 of the abdominal aorta 10 or it can be inflated such that it is smaller than the diameter of the inner wall 34 of the abdominal aorta 10 so that it will not entirely block the flow of blood through the abdominal aorta 10. Basically, the size of the balloon 524 can be easily varied by varying the inflation pressure of the balloon 524 thereby affecting the blood flow past renal arteries 12, 14.

It is to be understood that the drug infusion guide catheter 520 shown in FIG. 40 is preferably formed with three lumens therein. For example, the drug infusion guide catheter 520 can include a first relatively large lumen for the exchange of devices, a second relatively small lumen for drug infusion, and a third relatively small lumen for balloon inflation.

As previously stated above, it is beneficial to release a drug solution in the abdominal aorta 10, e.g., from the drug infusion guide catheter 520, during systole, as indicated by arrow 526 and arrow 528. During systole, the drug solution can flow in a generally downward direction from the infusion port 522, as indicated by arrow 530 and arrow 532, and into the right renal artery 12 and the left renal artery 14, as indicated by arrow 534 and arrow 536. It can be appreciated that the balloon 524 maximizes the flow of the drug solution into the renal arteries 12, 14. Per this embodiment, a counter pulsation of the balloon relative to the systolic/diastolic cycle may be used to enhance performance.

Figure 41:
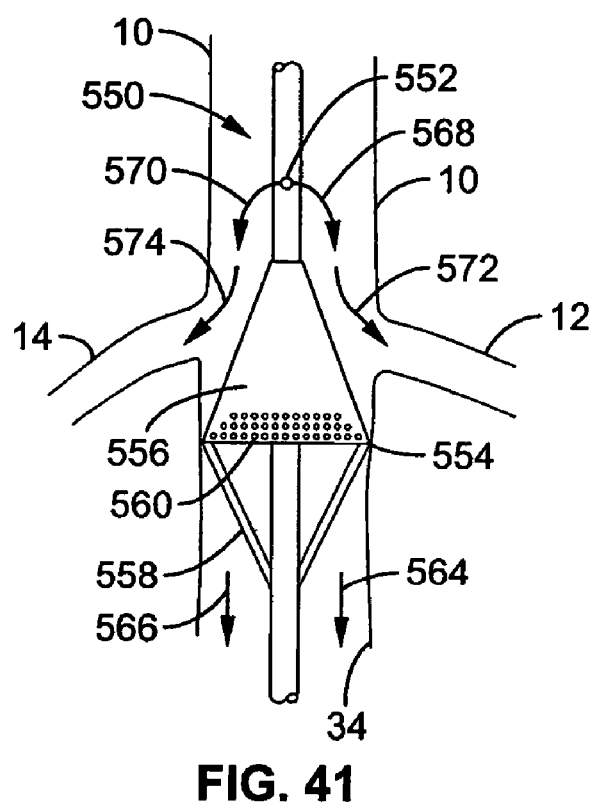
FIG. 41 is an anterior view of another fluid infusion guide catheter disposed within an abdominal aorta adjacent to the renal arteries.
Figure 42:
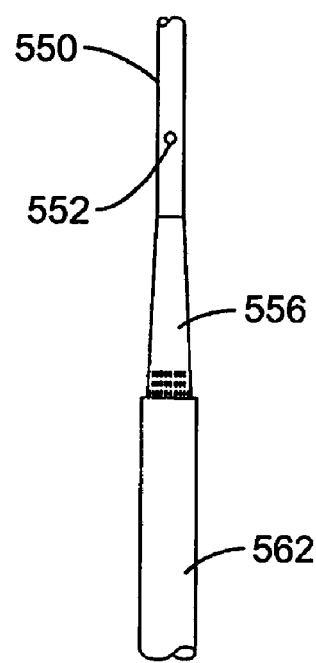
FIG. 42 is a plan view of the fluid infusion guide catheter shown in FIG. 41, except showing in another collapsed mode of use.

Referring now to FIG. 41 and FIG. 42, another embodiment of a drug infusion guide catheter is shown and is generally designated 550. As shown, the drug infusion guide catheter 550 can be advanced into the abdominal aorta 10, e.g., via the left or right iliac artery 22, 24 (FIG. 1), until it is in the vicinity of the renal arteries 12, 14. FIG. 41 shows that the drug infusion guide catheter 550 includes an infusion port 552 that is formed in the outer wall of the drug infusion guide catheter 550. It can be appreciated that a drug solution can be released from the drug infusion guide catheter 550 via the infusion port 552. As shown in FIG. 41, the drug infusion guide catheter 550 further includes a flow diverter 554 that can be expanded to divert blood flow into the renal arteries 12, 14.

FIG. 41 shows that the flow diverter 554 includes a membrane 556 that can be expanded by a frame 558—much like a basket or an umbrella. In this aspect of the present invention, the membrane 556 can be made from nylon, PEBAX, polyurethane, low density PTFE or any other similar material with low porosity to allow for blood diffusion through the membrane 556. Moreover, the membrane 556 can be lazed or otherwise formed with plural holes 560 of varying diameter, e.g., from twenty-five micrometers to five-hundred micrometers (25 µm-500 µm) to allow blood flow through the material film. In another embodiment, membrane 556 can be a wire mesh or stent-like devices. Further, the frame 558 is preferably made from a memory metal, e.g., NiTi, to allow for conformability to the aorta and pre-shaped capabilities. It can be appreciated that the flow diverter 554 can be expanded such that it engages the inner wall 34 of the abdominal aorta 10.

Referring briefly to FIG. 42, it is shown that the flow diverter 554 can be collapsed within an outer sheath 562 disposed around the drug infusion guide catheter 550. Once the drug infusion guide catheter 550 is in place within the abdominal aorta 10, the sheath 562 can be withdrawn causing the flow diverter 554 to be deployed near the renal arteries 12, 14.

It is to be understood that the drug infusion guide catheter 550 shown in FIG. 41 is preferably formed with at least two lumens therein. For example, the drug infusion guide catheter 550 can include a first relatively large lumen for the exchange of devices, and a second relatively small lumen for drug infusion.

As previously stated above, it is most beneficial to release a drug solution in the abdominal aorta 10, e.g., from the drug infusion guide catheter 550, during systole, as indicated by arrow 564 and arrow 566 shown in FIG. 41. During systole, the drug solution can flow in a generally downward direction from the infusion port 552, as indicated by arrow 568 and arrow 570, and into the right renal artery 12 and the left renal artery 14, as indicated by arrow 572 and arrow 574. It can be appreciated that the flow diverter 554, when deployed, maximizes the flow of the drug solution into the renal arteries 12, 14.

Figure 43:
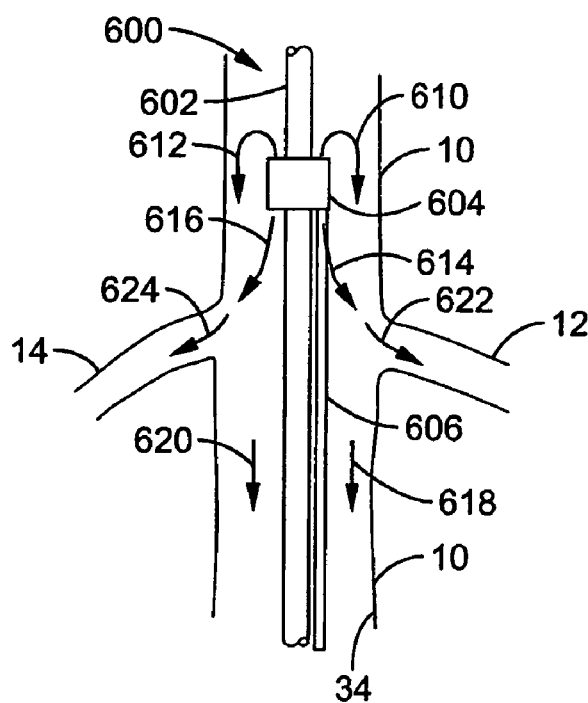
FIG. 43 is an anterior view of a guide catheter with a coaxial drug infuser disposed within an abdominal aorta adjacent to the renal arteries according to another embodiment.
Figure 44:
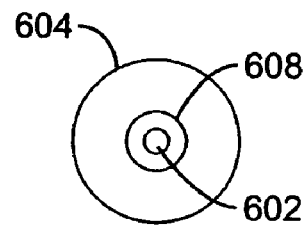
FIG. 44 is a top plan view of the system shown in FIG. 43.

Referring to FIG. 43 and FIG. 44, an embodiment of a guide catheter with a coaxial drug infuser is shown and is generally designated 600. FIG. 43 shows that the guide catheter with a coaxial drug infuser 600 includes a central catheter tube 602 around which a generally ring shaped, drug infuser 604 is slidably disposed. A drug infusion catheter 606 extends from the drug infuser 604 and can be used to supply a drug solution to the drug infuser 604. FIG. 44 shows that an annular space can be established between the drug infuser 604 and the central guide catheter 602. An infusion port (not shown) can be established in drug infuser 604, and is fluidly connected to drug infusion catheter 606.

FIG. 43 shows that a drug solution can exit the drug infuser 604 via the top of the drug infuser 604, as indicated by arrow 610 and arrow 612. The drug solution can also exit the drug infuser 604 at the bottom of the drug infuser 604, as indicated by arrow 614 and arrow 616. In one embodiment, the bottom of drug infuser 604 fits closely around central catheter tube 602 and drug solution flows preferably out the top as shown by arrow 610, 612. In another embodiment, the top of drug infuser 604 fits closely around central catheter tube 602 and drug solution flows preferably out the bottom as shown by arrow 614, 616 During systole, indicated by arrow 618 and arrow 620, the drug solution can flow into the right and left renal arteries 12, 14, as indicated by arrow 622 and arrow 624. When positioned below renal arteries 12, 14 (not shown) drug infuser 604 provides drug solution preferentially to the lower extremities. While a ring shape is shown, other embodiments, e.g. a partial ring, are contemplated for slideable coupling for independent positioning.

Figure 45:
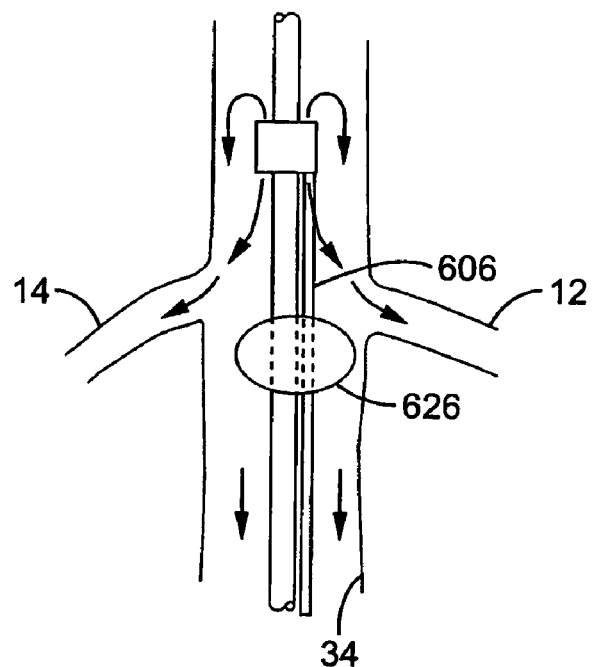
FIG. 45 is an anterior view of another guide catheter with a coaxial drug infuser disposed within an abdominal aorta adjacent to the renal arteries.

Referring now to FIG. 45, another embodiment of a guide catheter with a coaxial drug infuser is shown. As shown, the guide catheter with a coaxial drug infuser is identical to the embodiment shown in FIG. 43 and FIG. 44. However, the guide catheter with a coaxial drug infuser shown in FIG. 45 further includes a balloon 626 fluidly connected to the drug infusion catheter 606. The balloon 626 can be inflated to divert the flow of blood therearound and further increase the flow of the drug solution into the renal arteries 12, 14.

FIG. 46 shows a catheter assembly with a drug infusion introducer sheath, generally designated 640. As shown, the catheter assembly 640 includes a central guide catheter 642 that is inserted through the right iliac artery 22 and advanced until it is within the abdominal aorta 10. FIG. 46 further shows a drug infusion introducer sheath 644 around the central guide catheter 642. The drug infusion introducer sheath 644 defines a proximal end 646 and a distal end 648. As shown, the proximal end 646 of the introducer sheath 644 is attached to a catheter introducer hub 650 that can be used to advance the introducer sheath 644 into aorta 10. Preferably, the drug infusion introducer sheath 644 can be advanced until the distal end 648 of the introducer sheath 644 is at or above the renal arteries 12, 14.

Further, as shown in FIG. 46, an annular infusion port 652 is established between the central guide catheter 642 and the drug infusion introducer sheath 644. A drug solution can flow in the space between the central guide catheter 642 and the drug infusion introducer sheath 644 and exit through the annular infusion port 652 at or above the renal arteries 12, 14. The drug solution can then flow into the right renal artery 12, as indicated by arrow 654 and arrow 656. Moreover, the drug solution can flow into the left renal artery 14 as indicated by arrow 658 and arrow 660. It can be appreciated that the drug solution can be supplied to the drug infusion introducer sheath 644 via a drug infusion tube 662 connected to the catheter introducer hub 650. While an annular infusion port 652 is shown, other shapes for an infusion port may be contemplated.

In a beneficial embodiment, a standard catheter introducer sheath, usually 8-23 cm in length (not shown), is replaced with a longer catheter introducer sheath 644 that can reach the renal arteries. A longer sheath, 40-60 cm in length, depending on patient height and vascular tortuousity, is used in lieu of the standard catheter introducer sheath, and its distal tip is placed at a level slightly above the renals, preferably at or below the level of the superior mesenteric artery (SMA). The drug desired to be infused selectively into the renal arteries is infused through the catheter introducer sheath while the coronary procedure is performed. This is a marked improvement over systemic infusion of a drug solution since the flow to the renal arteries 12, 14 is about 30 percent of total aortic blood flow.

Figure 47:
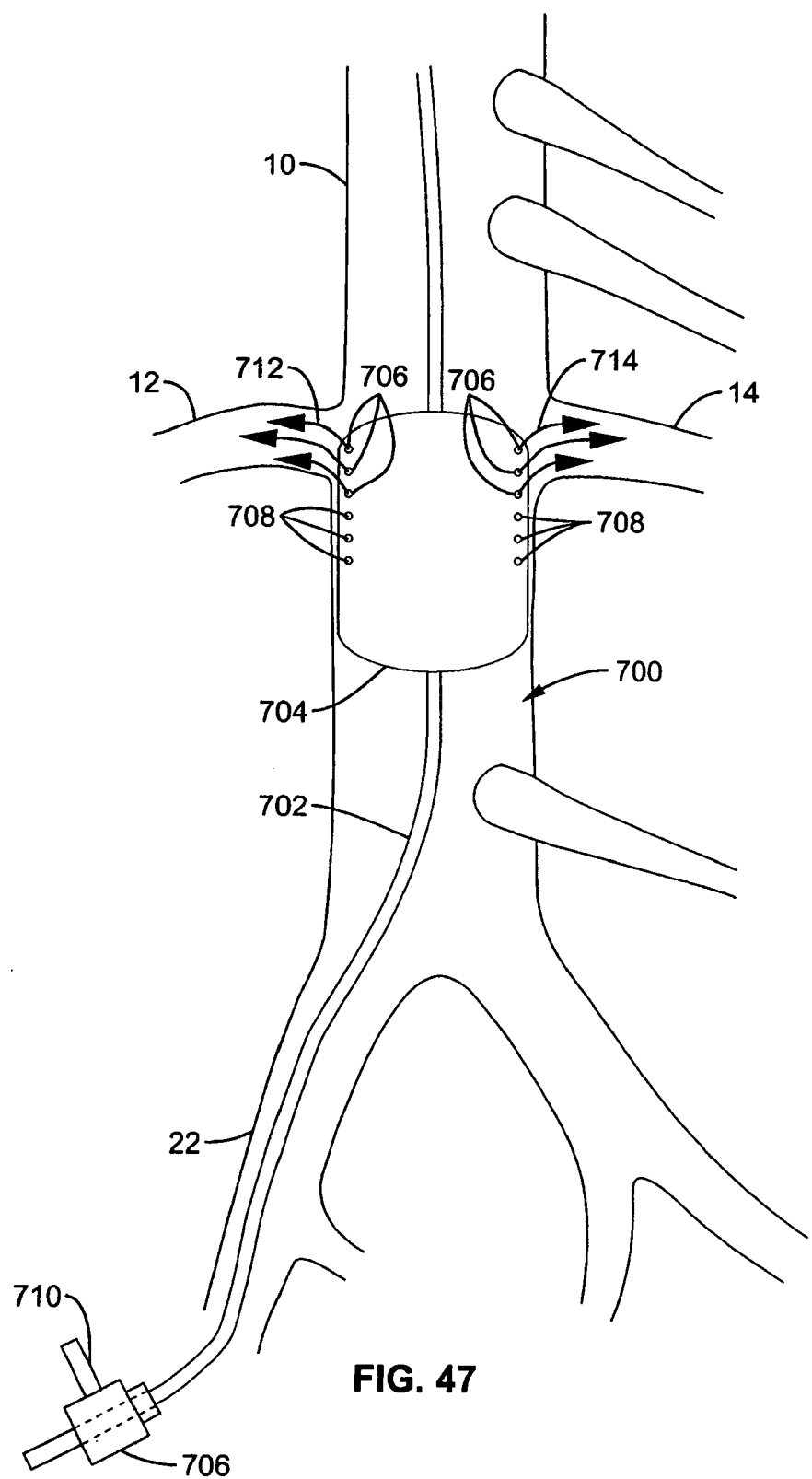
FIG. 47 is a perspective view of another catheter assembly with an infusion balloon disposed within an abdominal aorta adjacent to the renal arteries.

Referring to FIG. 47 a catheter assembly with an infusion or "weeping" balloon is shown and is generally designated 700. As shown, the catheter assembly 700 includes a central catheter tube 702 that is inserted through the right iliac artery 22 and advanced until it is within the abdominal aorta 10. FIG. 47 shows a drug infusion balloon 704 mounted midshaft on the central catheter tube 702. As shown, a catheter introducer hub 706 can be used to advance the central catheter tube 702 into the abdominal aorta 10. Preferably, the central catheter tube 702 can be advanced until the drug infusion balloon 704 is in the vicinity of the renal arteries 12, 14. In another beneficial embodiment, central catheter tube is advanced into the aorta system through an introducer sheath system (not shown). It is understood that central catheter tube 702 may have one or more lumens for drug solution delivery.

FIG. 47 shows that the drug infusion balloon 704 is formed with plural infusion ports 708. The infusion ports 708 are small enough to allow for pressure to be built up inside the drug infusion balloon 704. Additionally, the infusion ports 708 allow for a slow infusion of the inflating fluid, e.g., a drug solution, into the vascular system in which the drug infusion balloon 704 is placed, e.g., within the abdominal aorta 10.

In a beneficial embodiment, the central catheter tube 702 is advanced into the abdominal aorta 10 until the drug infusion balloon 704 is in the peri-renal aorta. The drug infusion balloon 704 is then inflated such that the drug infusion balloon 704 partially covers the renal arteries 12, 14. Some of the infusion ports 708 formed in the drug infusion balloon 704 can be pressed against the inner wall 34 of the abdominal aorta 10 and accordingly, be blocked thereby. Other infusion ports 706 in proximity to the renal arteries 12, 14 can be unblocked. A drug solution can be supplied to the drug infusion balloon 704 via the central catheter tube 702. A drug infusion tube 710 is connected to the catheter introducer hub 706 and supplies the drug solution to the central catheter tube 702. Since the drug solution can flow through the unblocked infusion ports 708, as indicated by arrow 712 and arrow 714, the delivery of the drug solution to the renal arteries 12, 14 is maximized.

It is to be understood that the catheter system 700 described in detail above can further include an intake (not shown) above the drug infusion balloon 704. Thus, blood can flow into the drug infusion balloon 704 and pre-mix with the drug solution within the drug infusion balloon 704 prior to delivery to the renal arteries. Additionally, it can be appreciated that the catheter system 700 described above can be an individual system or it can be incorporated with another interventional device, i.e., mounted on a guiding catheter.

Figure 48:
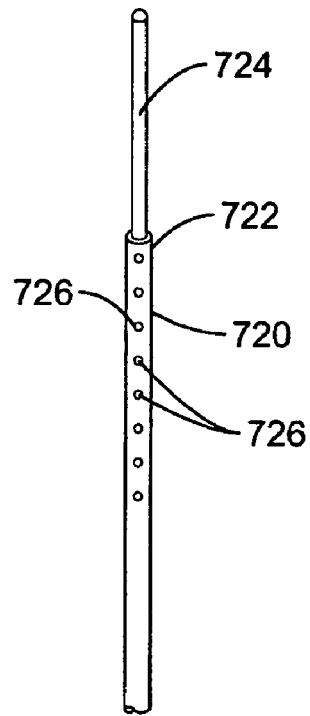
FIG. 48 is a rear perspective view of a self-shaping drug infusion catheter in a first configuration.
Figure 49:
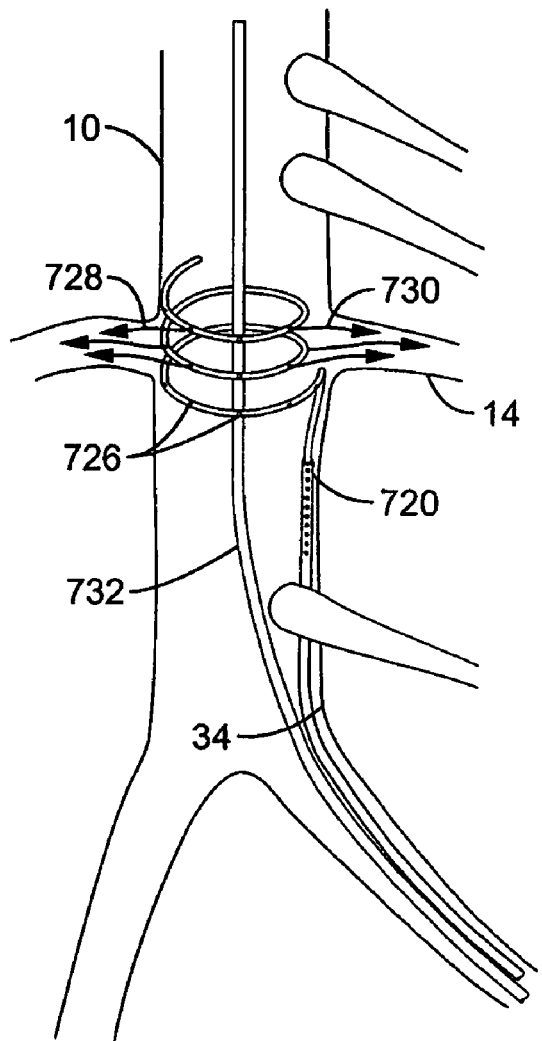
FIG. 49 is an anterior view of a self-shaping drug infusion catheter in a second shaped configuration and disposed within an abdominal aorta adjacent to the renal arteries.
Figure 50:
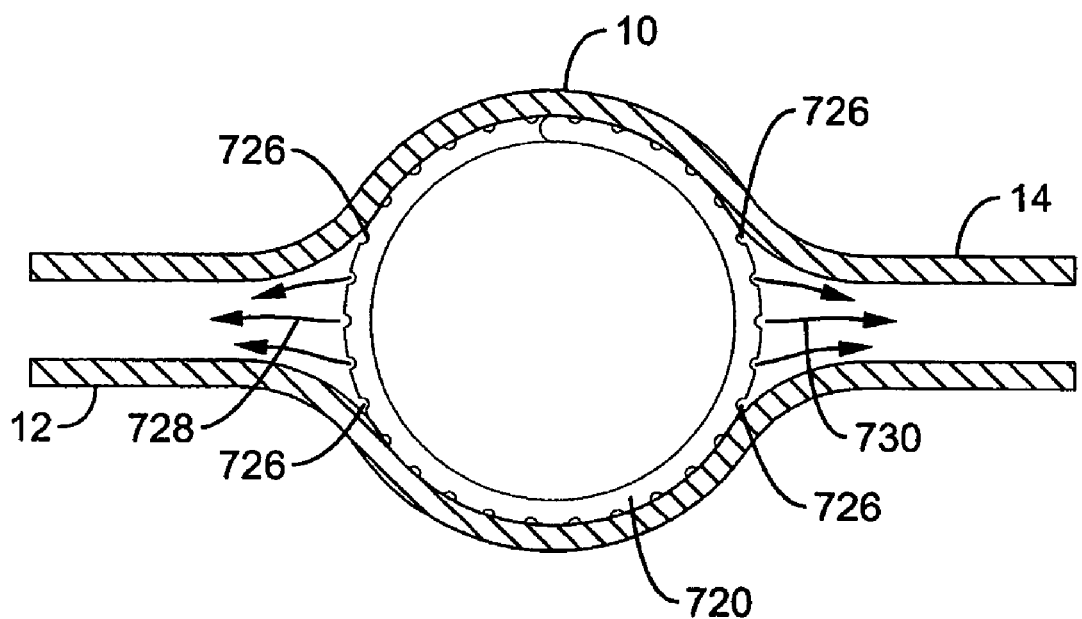
FIG. 50 is a top plan view of a self-shaping drug infusion catheter in a shaped configuration and disposed within an abdominal aorta adjacent to the renal arteries.

Referring now to FIG. 48 through FIG. 50 a self-shaping drug infusion catheter is shown and is generally designated 720. The self-shaping drug infusion catheter 720 includes a proximal end (not shown) and a distal end 722. FIG. 48 shows the self-shaping drug infusion catheter 720 installed over a guide wire 724. In one embodiment, the self-shaping drug infusion catheter 720 is made from a memory metal, e.g., NiTi, and a standard polymer. It is to be understood that the memory metal can be braided or coiled around a polymer tube. In another mode, the memory metal can be present in the polymer tube via a mandrel or a spine which runs the length of the self-shaping drug infusion catheter 720. The memory metal can be shape set to create the preferred free state shape of the self-shaping drug infusion catheter 720, described below.

Accordingly, as intended by the present embodiment, the self-shaping drug infusion catheter 720 can remain straight and highly flexible with the guide wire 724 installed therein. However, when the guide wire 724 is withdrawn, or otherwise retracted, from within the self-shaping drug infusion catheter 720, the self-shaping drug infusion catheter 720 returns to its free state shape. It can be appreciated that the self-shaping drug infusion catheter 720 can also return to its free state shape via a thermal response—if necessary.

In a beneficial embodiment, shown in FIG. 49 and FIG. 50, the free state shape of the self-shaping drug infusion catheter 720 is a generally spiral shape. Moreover, the self-shaping drug infusion catheter 720 is preferably formed with plural infusion ports 726. When the self-shaping drug infusion catheter 720 is in its free state shape, i.e., the spiral shape, the infusion ports 726 are located on the outside of the spiral. In another beneficial embodiment, the spiral shape can extend about 1 inch to about 2 inches in length.

FIG. 49 and FIG. 50 show the self-shaping drug infusion catheter 720 installed in an abdominal aorta 10. It can be appreciated that the self-shaping drug infusion catheter 720 can be inserted in the left iliac artery 24 and advanced therethrough until the distal end 722 of the drug infusion catheter 720 is in the general vicinity of the renal arteries 12, 14. As described above, when the guide wire 724 (FIG. 48) is withdrawn, the self-shaping drug infusion catheter 720 returns to its free shape, i.e., the spiral shape, such that the outer periphery of the self-shaping drug infusion catheter 720 is placed and somewhat pressed against the inner wall 34 of the abdominal aorta 10.

In the juxta-renal position, shown in FIG. 49 and FIG. 50, a majority of the infusion ports 726 established around the outer periphery are blocked by the inner wall 34 of the abdominal aorta 10. Several of the infusion ports 726, located at the renal ostia, are not blocked and can allow the flow of a drug solution into the right renal artery 12 and the left renal artery 14, as indicated by arrow 728 and arrow 730. By way of example and not of limitation, the infusion ring pressed against the aortic wall will not flow drugs under the very low infusion rates and pressures expected, i.e. approaching 1 ml per minute from an IV pole. However the infusion ring will flow drugs where they are free and not in contact with the aorta wall at the renal ostia. FIG. 49 shows that a second working catheter 732 can be introduced through the middle of the self-shaping drug infusion catheter 720 when it is in the free state spiral shape.

Figure 51:
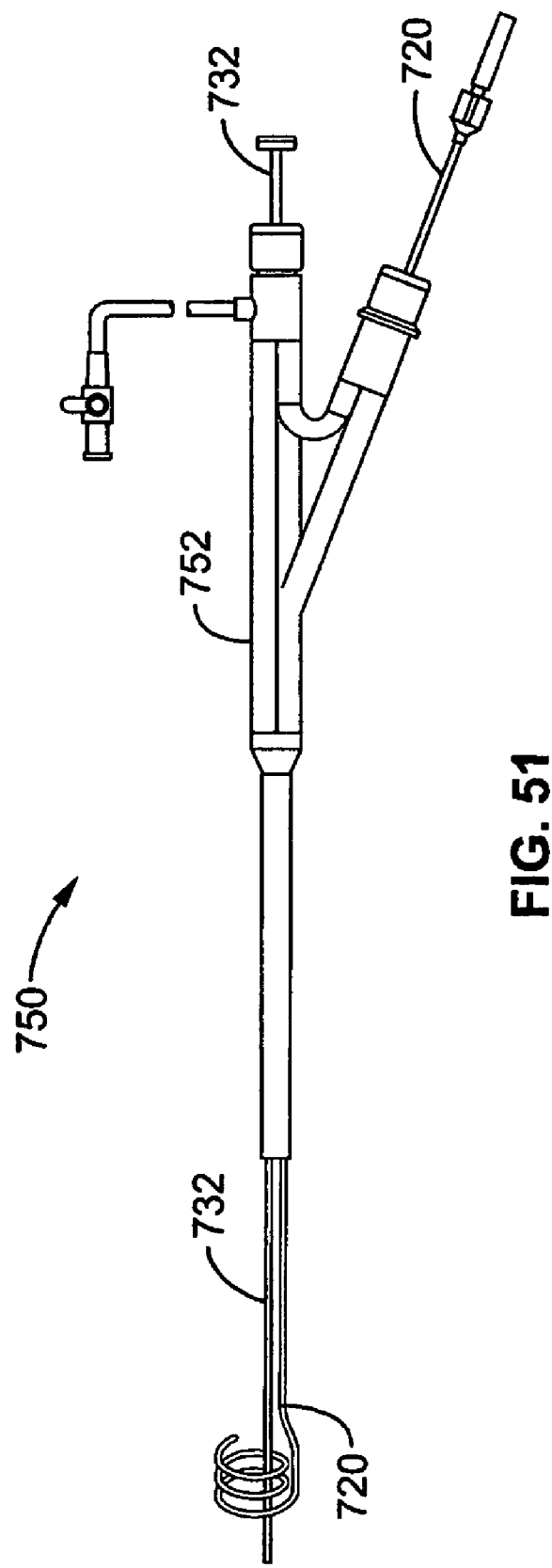
FIG. 51 is a side plan view of a self-shaping drug infusion catheter assembly.

FIG. 51 shows a self-shaping drug infusion catheter assembly generally designated 750 in which the self-shaping drug infusion catheter 720 and the working catheter 732 can be incorporated. As shown in FIG. 51, the self-shaping drug infusion catheter assembly 750 includes a Y hub assembly 752 through which the self-shaping drug infusion catheter 720 and the working catheter 732 can be introduced, and introducer sheath 754. It is to be understood that the overall length of the introducer sheath 754 shown in FIG. 51 can be relatively shorter than typical introducers used for tubular member flow diverters. This is largely due to the fact that the self-shaping drug infusion catheter 732 can be used to access the area of the renal arteries 12, 14, whereas other introducers may use an additional delivery sheath for this purpose. Further, the Y-hub assembly 752 shown in FIG. 51 can allow two catheters, e.g., the self-shaping drug infusion catheter 720 and the working catheter 732, to be placed, e.g., in the femoral artery through a single percutaneous cut-down. Also, the Y-hub assembly 752 provides adequate hemostasis and overall tactile feedback and control of the catheters used in conjunction therewith.

Figure 52:
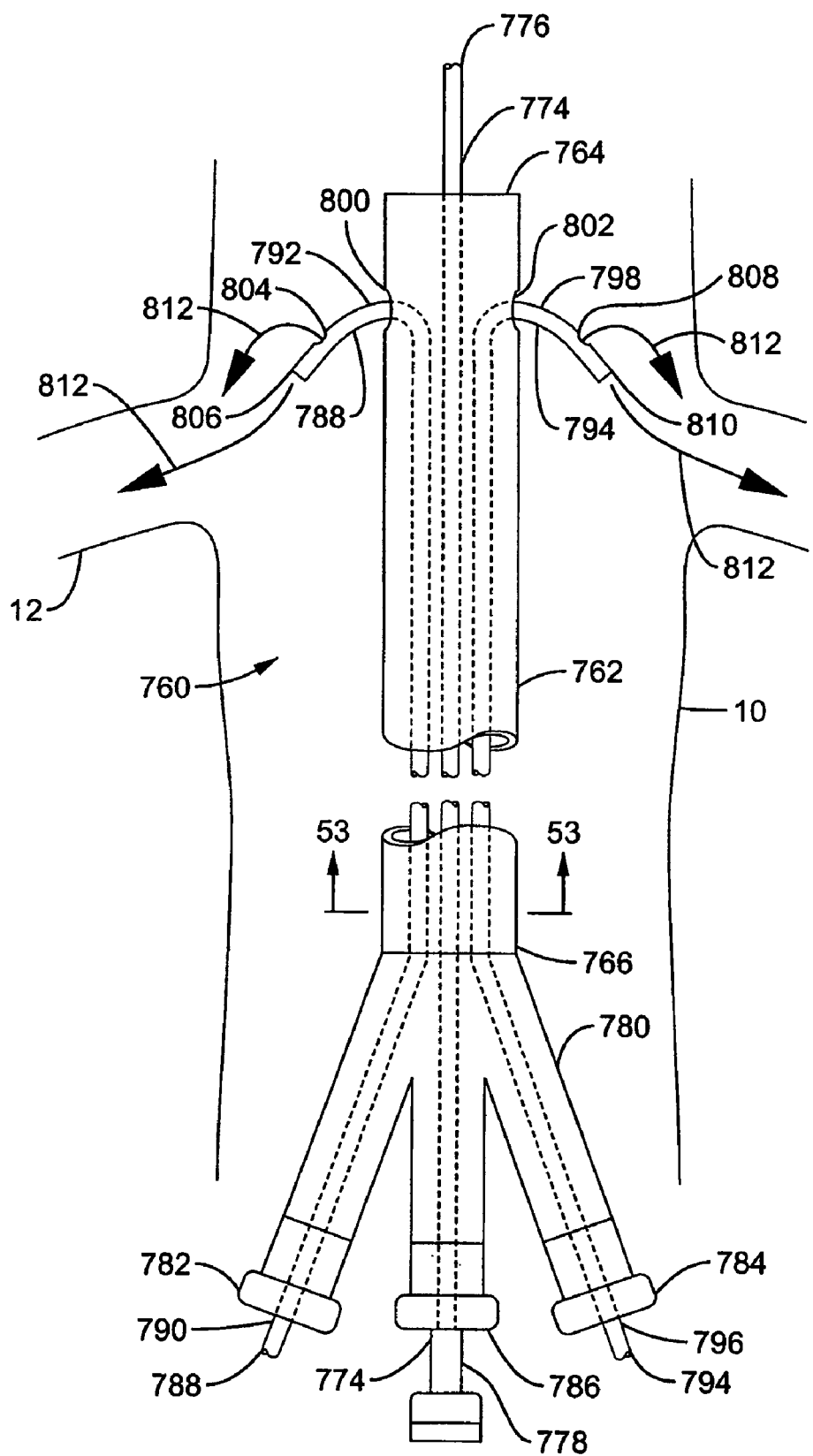
FIG. 52 is a side view of another embodiment of a catheter fluid delivery system with a multilumen sheath.
Figure 53:
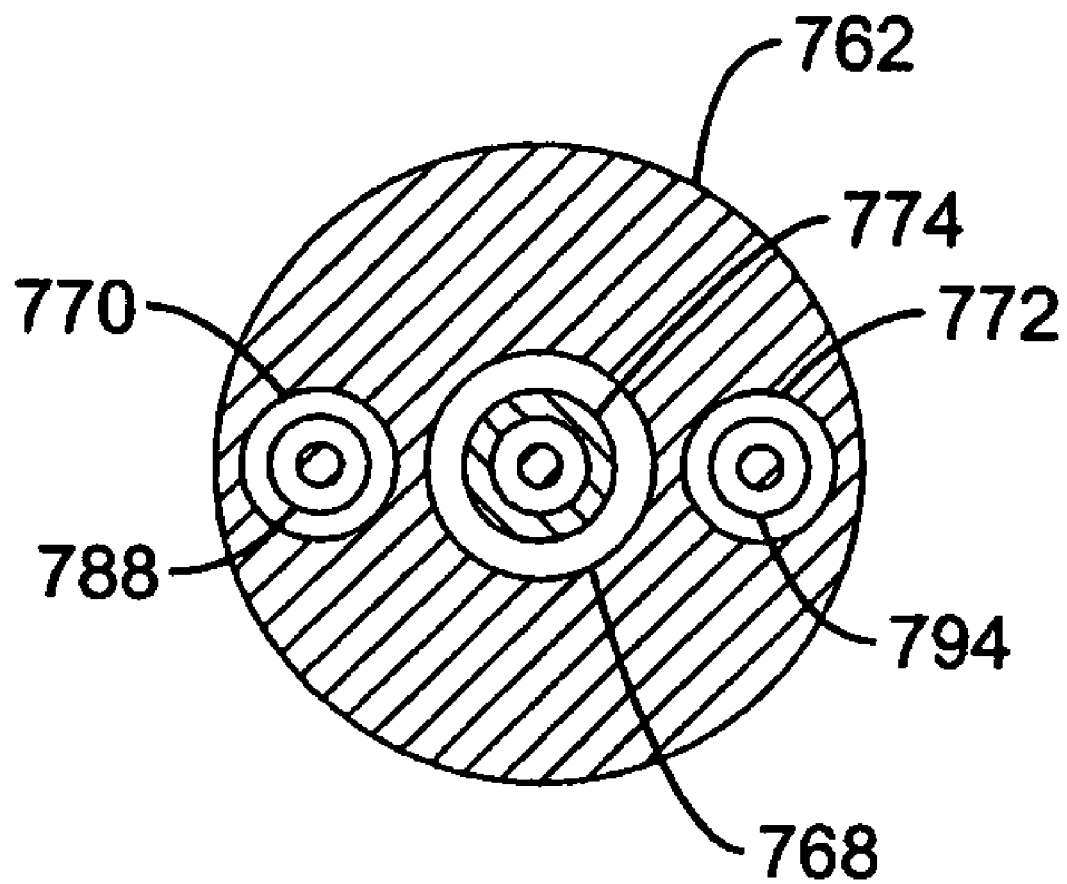
FIG. 53 is a top section view of the catheter fluid delivery system in FIG. 52.

FIG. 52 is a side view, and FIG. 53 a section view of another embodiment of a catheter system 760 with a multilumen sheath 762 having a distal end 764 and a proximal end 766. In FIG. 53, sheath 762 has center lumen 768, left lumen 770 and right lumen 772. A guide catheter 774, having a distal portion 776 and a proximal end 778 is inserted in center lumen 768. In one exemplary mode, guide catheter 774 is about 6 French in diameter.

In FIG. 52, proximal end 766 of sheath 762 is attached to a Y hub assembly 780. The illustration of Y hub assembly 780 is stylized for clarity. Y hub assembly 780 has left branch port 782 right branch port 784 and main port 786. Left fluid delivery tube 788 has proximal portion 790 and distal portion 792 with proximal portion 790 inserted in left branch port 782 and fluidly connected with distal portion 792 through left lumen 770. Right fluid delivery tube 794 has proximal portion 796 and distal portion 798 with proximal portion 790 inserted in right branch port 784 and fluidly connected with distal portion 798 through right lumen 772. Proximal end 778 of guide catheter 774 is inserted in main port 786 of Y hub assembly 780 and is connected to distal portion 776 through center lumen 768. Distal end of sheath 762 has left port 800 in left lumen 770 and right port 802 in right lumen 772. In one embodiment, left port 800 and right port 802 are 180 degrees apart. Distal portion 792 of left fluid delivery tube 788 has a memory shape to extend out of left port 800 when advanced in sheath 762 and has mid port 804 and end port 806. Distal portion 798 of right delivery tube 794 has a memory shape to extend out of right port 802 when advanced in sheath 762 and mid port 808 and end port 810.

In FIG. 52, sheath 762 has been inserted in aorta 10, shown in FIG. 1, and distal end 764 of sheath 762 is positioned upstream of renal arteries 12,14. Left and right fluid delivery tubes 788, 794 are advanced through left port 782 and right port 784 so distal ends 792, 798 extend towards left and right walls of aorta 10 respectively. Fluid agent, denoted by arrows 812, is released from mid ports 804, 808 and from end ports 806, 810 to preferentially flow into renal arteries 12,14. Guide catheter 774 is advanced through main port 786 of Y hub assembly 780 with distal portion 776 extending beyond distal end 764 of sheath 762 for further medical procedures.

FIG. 54 through FIG. 57 illustrates an embodiment of a proximal coupler system 850 used to deploy and position renal fluid delivery devices adjunctive with interventional catheters. FIG. 54 and FIG. 55 illustrate a proximal coupler system 850 in side view, and cut away section view. Y Hub body 852 is configured with an introducer sheath fitting 854 at the distal end 856 of hub body 852 and a main adapter fitting 858 at the proximal end 860 of Y hub body 852. Main branch 862 has tubular main channel 864 aligned on axis 866. Main channel 862 fluidly connects introducer sheath fitting 854 and main adapter fitting 858. By way of example and not of limitation, one embodiment of main channel 864 is adapted to accommodate a 6 Fr guide catheter. Side port fitting 868 is positioned on main branch 862 and is fluidly connected to main channel 864. Secondary branch 870 has tubular branch channel 872 that intersects main channel 864 at predetermined transition angle β. In one beneficial embodiment, transition angle β is approximately 20 degrees. Proximal end 874 of secondary branch 870 has secondary fitting 876. In one beneficial embodiment, a channel restriction 878 is molded into introducer sheath fitting 854. Y hub body 852 may be molded in one piece or assembled from a plurality of pieces.

Figure 56A:
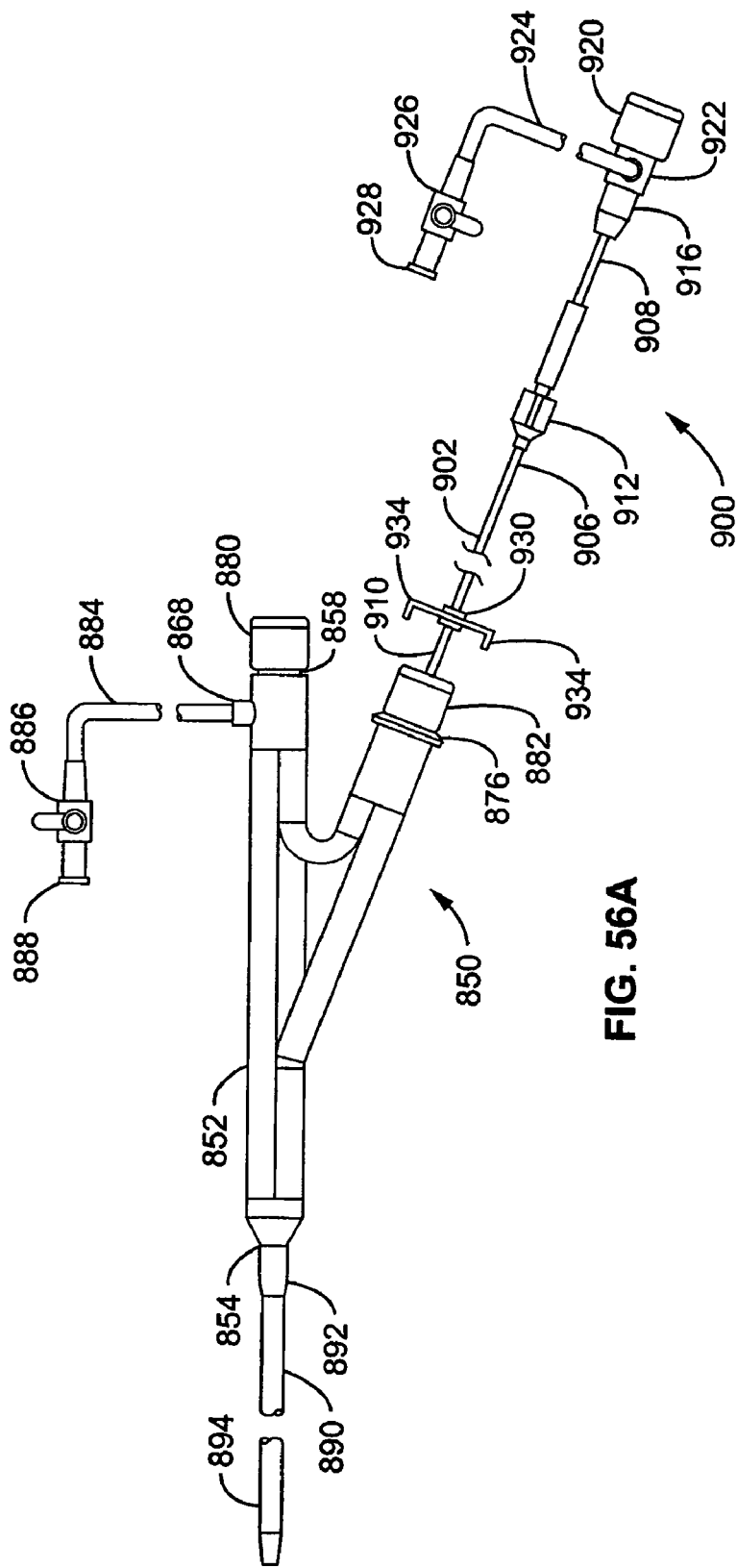
FIG. 56A illustrates a proximal coupler system as shown in FIG. 54 coupled to a local fluid delivery system.
Figure 56B:
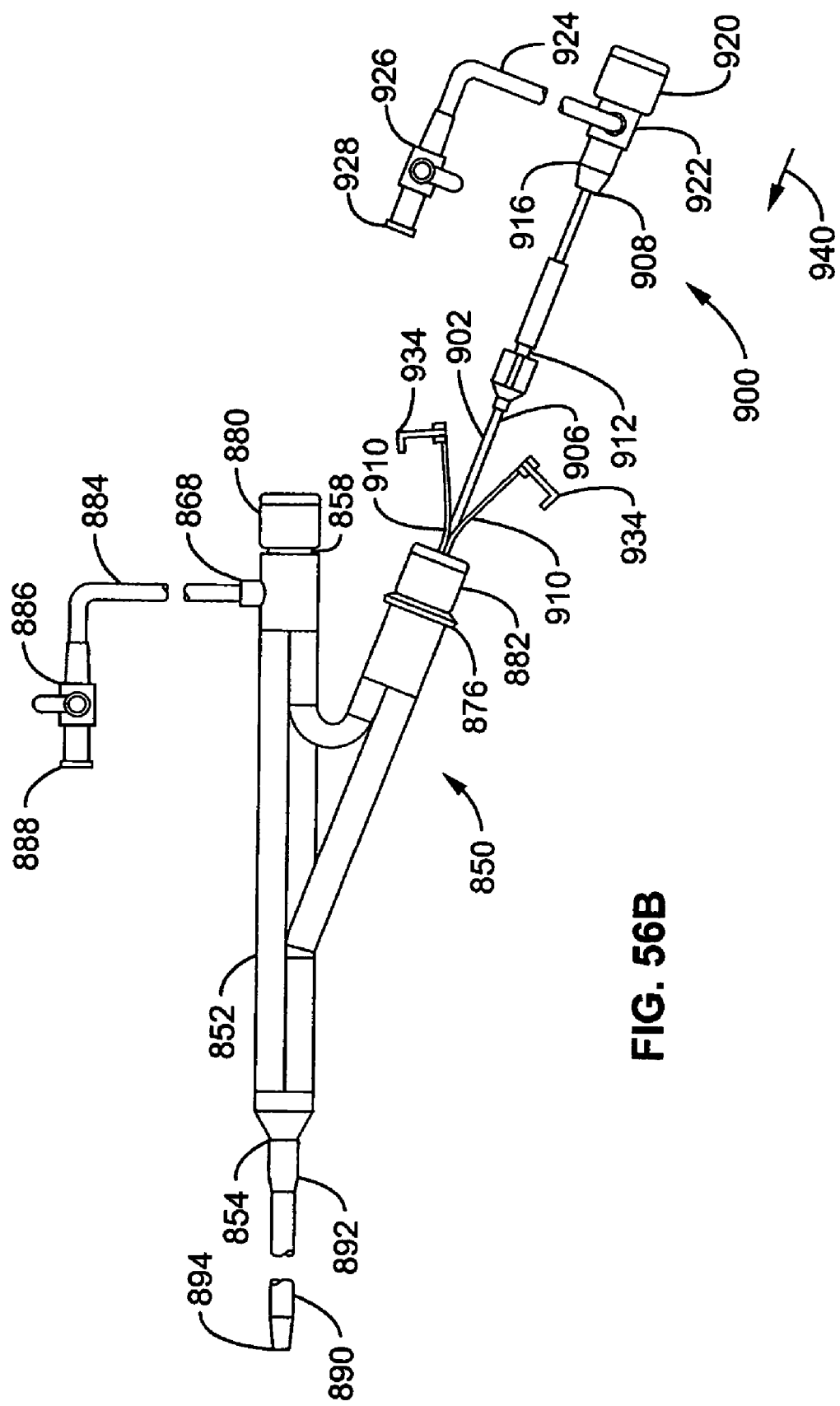
FIG. 56B illustrates a proximal coupler system as shown in FIG. 56A with a fluid delivery system advanced into an introducer sheath.

FIG. 56A and FIG. 56B illustrate a proximal coupler system 850 with a hemostasis valve 880 attached at main port 858 and Touhy Borst valve 882 attached at branch port 876. Fluid tube 884 is coupled to side port 868 and fluidly connects stop valve 886 and fluid port 888. Introducer sheath 890 with proximal end 892 and distal end 894 is coupled to Y hub body 852 at Sheath fitting 854. Proximal coupler system 850 is coupled to a local fluid delivery system 900. A stiff tube 902, has a distal end 904 (shown in FIG. 56B), a mid proximal section 906, and a proximal end 908. In one embodiment, stiff tube 902 is made of a Nickel-Titanium alloy. Stiff tube 902 is encased in delivery sheath 910 distal of mid proximal section 906. By way of example and not of limitation, delivery sheath 910 may be about 6 Fr to about 8 Fr in diameter. A torque handle 912 is coupled to stiff tube 902 at a mid proximal position 906. A material injection port 916 is positioned at the proximal end 908 of stiff tube 902. Material injection port 916 is coupled to an adapter valve 920 for introducing materials such as fluids. Side port fitting 922 is coupled to tube 924 and further coupled to stopcock 926 and fluid fitting 928. In an exemplary embodiment, adaptor 920 is a Luer valve. In another exemplary embodiment, side port fitting 922 is used for injecting a saline solution. Delivery sheath handle 930 is positioned and attached firmly at the proximal end 932 of delivery sheath 910. Delivery sheath handle 930 has two delivery handle tabs 934. In an exemplary embodiment, delivery sheath handle 930 is configured to break symmetrically in two parts when delivery handle tabs 934 are forced apart.

In FIG. 56B, Delivery sheath 910 is inserted through Touhy Borst adapter 882 through secondary branch channel 872 until distal end (not shown) of delivery sheath 910 is against channel restriction 878 (see FIG. 55). At that point, force 940 is applied in a distal direction at torque handle 912 to push stiff tube 902 through delivery tube 910. A fluid agent infusion device 936 on distal end 904 of stiff tube 902 is adapted to advance distally through introduction sheath 890. In FIG. 56B, stiff tube 602 has been advanced through introduction sheath 890 and past the distal end 894 of introduction sheath 890. Optionally, delivery sheath handle 930 is split in two by pressing inwardly on delivery handle tabs 934. Delivery sheath 910 may be split by pulling delivery tabs 934 apart and retracted from Y hub assembly 852 through Touhy Borst adapter 882 to allow a medical intervention device (shown in FIG. 57) to enter hemostasis valve 880 for further advancement through main channel 864 (see FIG. 55) and adjacent to stiff tube 902.

Figure 57:
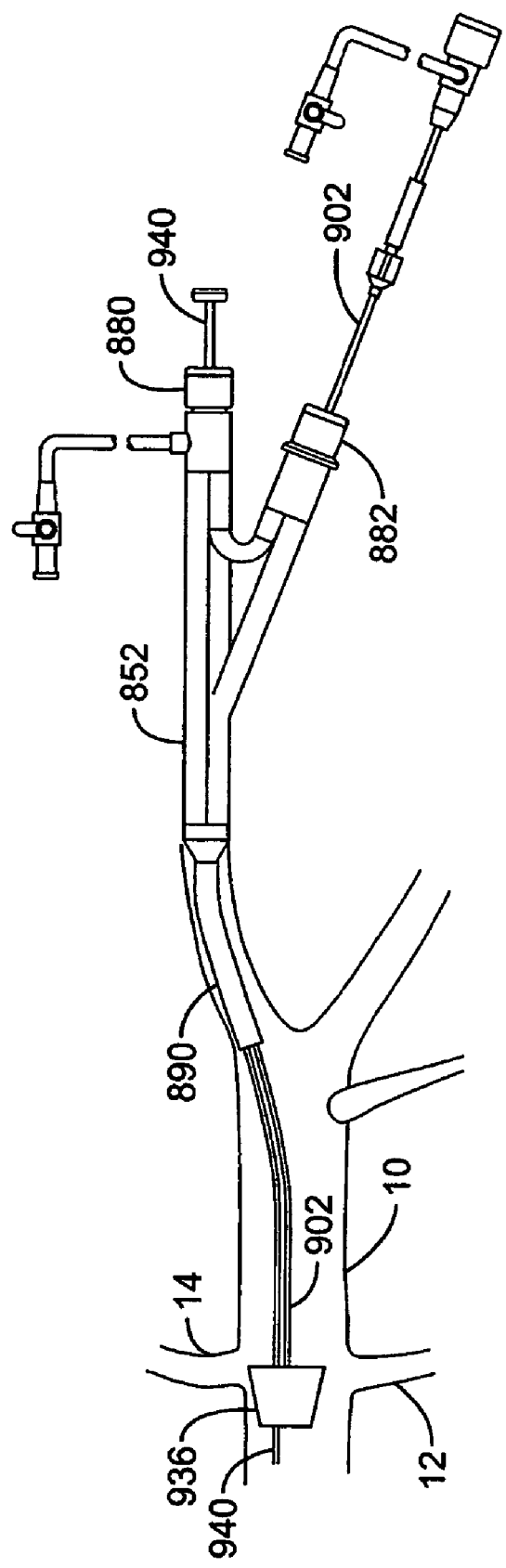
FIG. 57 illustrates a proximal coupler system as shown in FIG. 54 through 56B with a fluid infusion device positioned near the renal arteries and a catheter deployed adjunctively in the aorta.

FIG. 57 is an illustration of the proximal coupler system 850 of FIG. 56B with introducer sheath 890 is inserted in aorta system 10. Delivery sheath 910 has been retracted proximally and one or more fluid agent infusion devices 936 have been advanced and positioned at renal arteries 12,14. Intervention catheter 940 enters hemostasis valve 880 and is advanced through introducer sheath 890 and past fluid agent infusion device 936 for further medical intervention while fluid agent infusion device 936 remains in place at renal arteries 12,14. It is to be understood that proximal coupler systems can be further modified with additional branch ports to advance and position more than two devices through a single introducer sheath.

Figure 58:
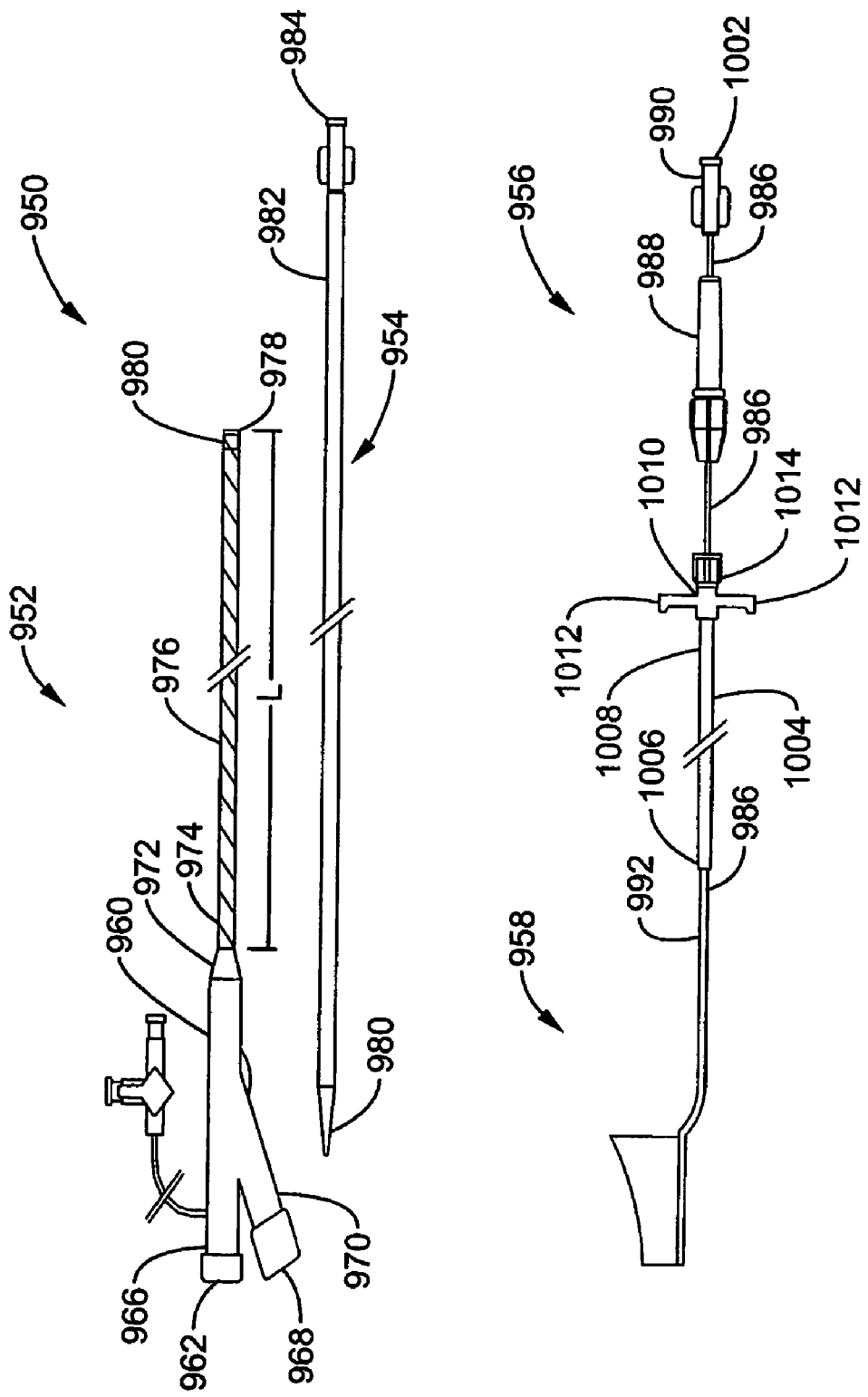
FIG. 58 illustrates a renal therapy system with an introducer sheath system, a vessel dilator, a fluid delivery system and an aortic infusion assembly.

FIG. 58 illustrates a further embodiment of the proximal coupler assembly and fluid delivery assembly shown in FIG. 57. Renal therapy system 950 includes an introducer sheath system 952, a vessel dilator 954 and a fluid delivery system 956 with a aortic infusion assembly 958. Details of channels, saline systems and fittings as shown previously in FIG. 54 through FIG. 57 are omitted for clarity. Introducer sheath system 952 has Y hub body 960 as shown previously in FIG. 54 and FIG. 55 configured various inner structures as shown previously in FIG. 55. Y hub body 960 has hemostasis valve 962 on proximal end 966 and Touhy Borst valve 968 on secondary end 970. Distal end 972 of Y hub body 960 is coupled to proximal end 974 of introducer sheath 976. Introducer sheath 976 has distal tip 978 that has a truncated cone shape and radiopaque marker band 980. In one embodiment, introducer sheath 976 is constructed with an inner liner of PTFE material, an inner coiled wire reinforcement and an outer polymer jacket. Introducer sheath 976 has predetermined length L measured from proximal end 974 to distal tip 978.

Vessel dilator 954, with distal end 980 and proximal end 982 is a polymer, (e.g. extrusion) tubing with a center lumen for a guide wire (not shown). Distal end 980 is adapted with a taper cone shape. Proximal end 982 is coupled to a Luer fitting 984.

Fluid delivery system 956 has stiff tube 986, torque handle 988, and proximal hub 990 as previously described in FIG. 56A and FIG. 56B with aortic infusion assembly 958 coupled at distal end 992. The proximal hub 990 of fluid delivery system 956 has a Luer fitting 1002 for infusing a fluid agent, and is fluidly coupled with the stiff tube 986.

A single lumen, tear-away delivery sheath 1004 has a distal end 1006, a proximal end 1008, and slidingly encases stiff tube 986. Delivery sheath 1004 is positioned between the torque handle 988 and the bifurcated catheter 956. The distal end 1006 has a shape and outer diameter adapted to mate with the channel restriction in the distal end of the main channel of the Y hub body as shown previously in FIG. 55. The proximal end 1008 of the delivery sheath 1004 is coupled to a handle assembly 1010 with two handles 1012 and a tear away cap 1014.

Dilator 954 is inserted through Touhy Borst valve 968 on secondary port 970 until distal end 980 protrudes from distal tip 978 of introducer sheath 976 to form a smooth outer conical shape. Distal tip 978 of introducer sheath 976 is positioned in the aorta system near the renal arteries (not shown). Dilator 954 is removed and fluid delivery device 956 is prepared by sliding delivery sheath 1004 distally until aortic infusion assembly 958 is enclosed in delivery sheath 1004. Distal end 1006 of delivery sheath 1004 is inserted in Touhy Borst valve 968 and advanced to the restriction in the main channel of the Y hub body shown in FIG. 55. Aortic infusion assembly 958 is advanced distally into introducer sheath 976. Tear away delivery sheath 1004 is retracted and removed through Touhy Borst valve 968 as shown previously in FIG. 56B. Aortic infusion assembly 958 is advanced distally out of the distal tip 978 of introducer sheath 976 and positioned to infuse fluid agent in the renal arteries as shown in FIG. 57.

FIG. 59 is a stylized illustration of a double Y proximal coupler 1150 with two local fluid delivery systems 1152, 1154 and an intervention catheter 1156 in an aorta system 10. Details of local fluid delivery systems 1152, 1154 are shown in FIGS. 56A and 56B and are omitted here for clarity. The double Y proximal coupler 1150 is constructed similar to a proximal coupler assembly as shown in FIG. 54 and FIG. 55 but with another branch port added. Secondary branch 1160 accommodates local fluid delivery system 1152 for drug infusion in right renal artery 12. Tertiary branch 1164 accommodates local fluid delivery system 1154 for drug infusion in left renal artery 14. intervention catheter 1156 enters double Y proximal coupler 1150 through hemostasis valve 1168. Introduction sheath 1170 is sized to accommodate local fluid delivery systems 1152, 1154 and catheter 1156 simultaneously. FIG. 59 illustrates secondary branch 1160 and tertiary branch 1164 on the same side of the double proximal coupler, however they may be positioned on opposite sides or in another beneficial configuration. By way of example and not of limitation, the cross section of local fluid delivery system 1152, 1154 may be oval shaped. By way of example and not of limitation, double Y proximal coupler 1150 may be adapted to advance a wide mix of medical devices such as guide wires, diagnostic catheters, flow diverters and infusion assemblies through introducer sheath 1170 and into a vascular system such as aorta system 10.

It is to be understood that each of the embodiments described in detail above provide a device that can be used for selective therapeutic drug infusion as sites remote to a primary treatment site. These devices can be applicable to interventional radiology procedures, including interventional diagnostic and therapeutic procedures involving the coronary arteries. Further, each of the devices described above, can be beneficial for delivering certain drugs, e.g., papaverine; Nifedipine; Verapamil; fenoldopam mesylate; Furosamide; Thiazide; and Dopamine; or analogs, derivatives, combinations, or blends thereof, to the renal arteries of a patient who is simultaneously undergoing a coronary intervention with the intent of increasing the kidney's ability to process of organically-bound iodine, i.e., radiographic contrast, as measured by serum creatinine and glomerular filtration rate (GFR).

The various embodiments herein described for the present invention can be useful in treatments and therapies directed at the kidneys such as the prevention of radiocontrast nephropathy (RCN) from diagnostic treatments using iodinated contrast materials. As a prophylactic treatment method for patients undergoing interventional procedures that have been identified as being at elevated risk for developing RCN, a series of treatment schemes have been developed based upon local therapeutic agent delivery to the kidneys. Among the agents identified for such treatment are normal saline (NS) and the vasodilators papaverine (PAP) and fenoldopam mesylate (FM).

The approved use for fenoldopam is for the in-hospital intravenous treatment of hypertension when rapid, but quickly reversible, blood pressure lowering is needed. Fenoldopam causes dose-dependent renal vasodilation at systemic doses as low as approximately 0.01 mcg/kg/min through approximately 0.5 mcg/kg/min IV and it increases blood flow both to the renal cortex and to the renal medulla. Due to this physiology, fenoldopam may be utilized for protection of the kidneys from ischemic insults such as high-risk surgical procedures and contrast nephropathy. Dosing from approximately 0.01 to approximately 3.2 mcg/kg/min is considered suitable for most applications of the present embodiments, or about 0.005 to about 1.6 mcg/kg/min per renal artery (or per kidney). As before, it is likely beneficial in many instances to pick a starting dose and titrate up or down as required to determine a patient's maximum tolerated systemic dose. Recent data, however, suggest that about 0.2 mcg/kg/min of fenoldopam has greater efficacy than about 0.1 mcg/kg/min in preventing contrast nephropathy and this dose is preferred.

The dose level of normal saline delivered bilaterally to the renal arteries may be set empirically, or beneficially customized such that it is determined by titration. The catheter or infusion pump design may provide practical limitations to the amount of fluid that can be delivered; however, it would be desired to give as much as possible, and is contemplated that levels up to about 2 liters per hour (about 25 cc/kg/hr in an average about 180 lb patient) or about one liter or 12.5 cc/kg per hour per kidney may be beneficial.

Local dosing of papaverine of up to about 4 mg/min through the bilateral catheter, or up to about 2 mg/min has been demonstrated safety in animal studies, and local renal doses to the catheter of about 2 mg/min and about 3 mg/min have been shown to increase renal blood flow rates in human subjects, or about 1 mg/min to about 1.5 mg/min per artery or kidney. It is thus believed that local bilateral renal delivery of papaverine will help to reduce the risk of RCN in patients with pre-existing risk factors such as high baseline serum creatinine, diabetes mellitus, or other demonstration of compromised kidney function.

It is also contemplated according to further embodiments that a very low, systemic dose of papaverine may be given, either alone or in conjunction with other medical management such as for example saline loading, prior to the anticipated contrast insult. Such a dose may be on the order for example of between about 3 to about 14 mg/hr (based on bolus indications of approximately 10-40 mg about every 3 hours—papaverine is not generally dosed by weight). In an alternative embodiment, a dosing of 2-3 mg/min or 120-180 mg/hr. Again, in the context of local bilateral delivery, these are considered halved regarding the dose rates for each artery itself.

Notwithstanding the particular benefit of this dosing range for each of the aforementioned compounds, it is also believed that higher doses delivered locally would be safe. Titration is a further mechanism believed to provide the ability to test for tolerance to higher doses. In addition, it is contemplated that the described therapeutic doses can be delivered alone or in conjunction with systemic treatments such as intraveneous saline.

From the foregoing discussion, it will be appreciated that the various embodiments described herein generally provide for infusion of renal protective drugs into each of two renal arteries perfusing both kidneys in a patient. The devices and methods of these embodiments are useful in prophylaxis or treatment of kidney malfunction or conditions, such as for example ARF. Various drugs may be delivered via the systems and methods described, including for example: vasodilators; vasopressors; diuretics; Calcium-channel blockers; or dopamine DA1 agonists; or combinations or blends thereof. Further, more specific, examples of drugs that are contemplated in the overall systems and methods described include but are not limited to: Papaverine; Nifedipine; Verapamil; Fenoldapam; Furosamide; Thiazide; and Dopamine; or analogs, derivatives, combinations, or blends thereof.

It is to be understood that the invention can be practiced in other embodiments that may be highly beneficial and provide certain advantages. For example radiopaque markers are shown and described above for use with fluoroscopy to manipulate and position the introducer sheath and the intra aortic catheters. The required fluoroscopy equipment and auxiliary equipment devices are typically located in a specialized location limiting the in vivo use of the invention to that location. Other modalities for positioning intra aortic catheters are highly beneficial to overcome limitations of fluoroscopy. For example, non fluoroscopy guided technology is highly beneficial for use in operating rooms, intensive care units, and emergency rooms, where fluoroscopy may not be readily available or its use may cause undue radiation exposure to users and others due to a lack of specific radiation safeguards normally present in angiography suites and the like. The use of non-fluoroscopy positioning allows intra aortic catheter systems and methods to be used to treat other diseases such as ATN and CHF in clinical settings outside of the angiography suite or catheter lab.

In one embodiment, the intra aortic catheter is modified to incorporate marker bands with metals that are visible with ultrasound technology. The ultrasonic sensors are placed outside the body surface to obtain a view. In one variation, a portable, noninvasive ultrasound instrument is placed on the surface of the body and moved around to locate the device and location of both renal ostia. This technology is used to view the aorta, both renal ostia and the intra aortic catheter.

In another beneficial embodiment, ultrasound sensors are placed on the introducer sheath and the intra aortic catheter itself; specifically the tip of the aortic catheter or at a proximal section of the catheter. The intra aorta catheter with the ultrasonic sensors implemented allows the physician to move the sensors up and down the aorta to locate both renal ostia.

A further embodiment incorporates Doppler ultrasonography with the intra aortic catheters. Doppler ultrasonography detects the direction, velocity, and turbulence of blood flow. Since the renal arteries are isolated along the aorta, the resulting velocity and turbulence is used to locate both renal ostia. A further advantage of Doppler ultrasonography is it is non invasive and uses no x rays.

A still further embodiment incorporates optical technology with the intra aorta catheter. An optical sensor is placed at the tip of the introducer sheath. The introducer sheath's optical sensor allows visualization of the area around the tip of the introducer sheath to locate the renal ostia. In a further mode of this embodiment, a transparent balloon is positioned around the distal tip of the introducer sheath. The balloon is inflated to allow optical visual confirmation of renal ostium. The balloon allows for distance between the tip of the introducer sheath and optic sensor while separating aorta blood flow. That distance enhances the ability to visualize the image within the aorta. In a further mode, the balloon is adapted to allow profusion through the balloon wall while maintaining contact with the aorta wall. An advantage of allowing wall contact is the balloon can be inflated near the renal ostium to be visually seen with the optic sensor. In another mode, the optic sensor is placed at the distal tips of the intra aortic catheter. Once the intra aortic catheter is deployed within the aorta, the optic sensor allows visual confirmation of the walls of the aorta. The intra aortic catheter is tracked up and down the aorta until visual confirmation of the renal ostia is found. With the optic image provided by this mode, the physician can then track the positioning of the intra aortic catheter to the renal arteries.

Another embodiment uses sensors that measure pressure, velocity, and/or flow rate to locate renal ostia without the requirement of fluoroscopy equipment. The sensors are positioned at the distal end of the intra aortic catheter. The sensors display real time data about the pressure, velocity, and/or flow rate. With the real-time data provided, the physician locates both renal ostia by observing the sensor data when the intra aortic catheter is around the approximate location of the renal ostia. In a further mode of this embodiment, the intra aortic catheter has multiple sensors positioned at a mid distal and a mid proximal position on the catheter to obtain mid proximal and mid distal sensor data. From this real time data, the physician can observe a significant flow rate differential above and below the renal arteries and locate the approximate location. With the renal arteries being the only significant sized vessels within the region, the sensors would detect significant changes in any of the sensor parameters.

In a still further embodiment, chemical sensors are positioned on the intra aortic catheter to detect any change in blood chemistry that indicates to the physician the location of the renal ostia. Chemical sensors are positioned at multiple locations on the intra aortic catheter to detect chemical change from one sensor location to another.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A local renal infusion system for treating a renal system in a patient from a location within the abdominal aorta associated with first and second flow paths within an outer region of abdominal aortic blood flow generally along the abdominal aorta wall and into first and second renal arteries, respectively, via their corresponding first and second renal ostia along an abdominal aorta wall in the patient, comprising:

a local injection assembly comprising a first infusion tube having a distal end, a proximal end, and a first injection port disposed between the distal end and the proximal end, a second infusion tube having a distal end, a proximal end, and a second injection port disposed between the distal end and the proximal end, and a central catheter tube with first and second injection ports;

wherein the distal end of the first infusion tube and the distal end of the second infusion tube are attached to the central catheter tube, such that when the first infusion tube and the second infusion tube are in an expanded configuration the first infusion tube and the second infusion tube bow outward away from the central catheter tube, and when the first infusion tube and the second infusion tube are in a retracted configuration the first infusion tube and the second infusion tube straighten inward toward the central catheter tube;

wherein the local injection assembly is adapted to be positioned at the location with the first and second injection ports at first and second respective positions, respectively, corresponding with the first and second flow paths;

wherein the local injection assembly is adapted to be fluidly coupled to a source of fluid agent externally of the patient when the local injection assembly is positioned at the location; and wherein the local injection assembly is adapted to inject a volume of fluid agent from the source, through the first and second injection ports at the first and second positions, respectively, and bi-laterally into the first and second renal arteries, also respectively, via the respective corresponding first and second renal ostia without substantially altering abdominal aorta flow along the location.

2. The system of claim 1, wherein the local injection assembly is adapted to inject the volume of fluid agent into the first and second flow paths such that the injected volume flows substantially only into the first and second renal arteries without substantially diverting one region of aortic blood flow into another region of aortic blood flow.

3. The system of claim 1, wherein the local injection assembly is adapted to inject the volume of fluid agent into the first and second flow paths such that the injected volume flows substantially only into the first and second renal arteries without substantially occluding abdominal aortic blood flow.

4. The system of claim 1, wherein the local injection assembly is adapted to inject the volume of fluid agent into the first and second flow paths such that the injected volume flows substantially only into the first and second renal arteries without substantially isolating the first or second flow paths from adjacent flow paths at the location.

5. The system of claim 1, further comprising:
a delivery member with a proximal end portion and a distal end portion with a longitudinal axis;
wherein the local injection assembly comprises first and second injection members with first and second injection ports, respectively;
wherein the local injection assembly is adapted to extend from the distal end portion of the delivery member and is adjustable between a first configuration and a second configuration;
wherein the local injection assembly in the first configuration is adapted to be delivered by the delivery member to the location; and
wherein the local injection assembly at the location is adjustable from the first configuration to the second configuration such that the first and second first injection members are radially extended from the longitudinal axis with the first and second injection ports located at the first and second positions, respectively, at the first and second flow paths.

6. The system of claim 1, wherein:
the local injection assembly further comprises an elongate body with a longitudinal axis and that is adapted to be positioned at the location;
the first and second injection members in the first configuration have first radial positions relative to the longitudinal axis; and
the first and second injection members in the second configuration have second radial positions that are radially extended from the longitudinal axis relative to the first radial position.

7. The system of claim 6, wherein:
the first and second injection members are located on opposite respective sides of the elongate body around a circumference of the elongate body.

8. The system of claim 7, wherein:
each of the first and second injection members extends between proximal and distal respective locations on each of the opposite respective sides of the elongate body; and
in the second configuration the first and second injection members are biased outward from the elongate body between the respective proximal and distal respective locations.

9. The system of claim 8, wherein:
each of the first and second injection members has a length that is longer than a distance between the respective proximal and distal locations;
each respective proximal location comprises a port;
each of the first and second injection members in the first configuration has a proximal section that extends proximally within the respective port at the respective proximal location and into the elongate body; and
the proximal section of each of the first and second injection members in the second configuration is advanced distally through the port to extend from the elongate body.

10. The system of claim 5, further comprising:
first and second markers located along the first and second injection members, respectively, at locations generally corresponding with the first and second injection ports; and
wherein each of the first and second markers is adapted to indicate to an operator externally of the patient the locations of the first and second injection ports to assist their delivery to the first and second positions, respectively.

11. The system of claim 10, wherein the first and second markers comprise radiopaque markers.

* * * * *